(12) United States Patent
Lilienfeld et al.

(10) Patent No.: US 7,985,776 B2
(45) Date of Patent: *Jul. 26, 2011

(54) IONTOPHORETIC DELIVERY OF CURCUMIN AND CURCUMIN ANALOGS FOR THE TREATMENT OF ALZHEIMER'S DISEASE

(75) Inventors: Sean Lilienfeld, Sharon, MA (US); Thomas M. Di Mauro, Southboro, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/147,881

(22) Filed: Jun. 27, 2008

(65) Prior Publication Data
US 2009/0325963 A1  Dec. 31, 2009

(51) Int. Cl.
  *A61K 31/535* (2006.01)
  *A61K 31/12* (2006.01)
  *A61K 31/22* (2006.01)
(52) U.S. Cl. ............... 514/681; 514/238.8; 514/551
(58) Field of Classification Search .......... 514/681; 424/43
See application file for complete search history.

(56) References Cited

U.S. PATENT DOCUMENTS

| | | |
|---|---|---|
| 2,955,898 A | 10/1960 | Bailey |
| 4,105,034 A | 8/1978 | Shalaby |
| 4,130,639 A | 12/1978 | Shalaby |
| 4,140,678 A | 2/1979 | Shalaby |
| 4,141,087 A | 2/1979 | Shalaby |
| 4,205,399 A | 6/1980 | Shalaby |
| 4,208,511 A | 6/1980 | Shalaby |
| 4,482,722 A | 11/1984 | Thorbek |
| 4,529,556 A | 7/1985 | Bruza |
| 5,073,641 A | 12/1991 | Bundgaard |
| 5,334,315 A | 8/1994 | Matkovich |
| 5,401,777 A | 3/1995 | Ammon |
| 5,462,667 A | 10/1995 | Wollinsky |
| 5,464,929 A | 11/1995 | Bezwada |
| 5,595,751 A | 1/1997 | Bezwada |
| 5,597,579 A | 1/1997 | Bezwada |
| 5,607,687 A | 3/1997 | Bezwada |
| 5,618,552 A | 4/1997 | Bezwada |
| 5,620,698 A | 4/1997 | Bezwada |
| 5,622,944 A | 4/1997 | Hale |
| 5,645,850 A | 7/1997 | Bezwada |
| 5,648,088 A | 7/1997 | Bezwada |
| 5,679,864 A | 10/1997 | Krackov |
| 5,698,213 A | 12/1997 | Jamiolkowski |
| 5,700,583 A | 12/1997 | Jamiolkowski |
| 5,859,150 A | 1/1999 | Jamiolkowski |
| 5,876,714 A | 3/1999 | Nishikawa |
| 5,891,924 A | 4/1999 | Aggarwal |
| 5,980,480 A | 11/1999 | Rubenstein |
| 5,980,481 A | 11/1999 | Gorsuch |
| 6,096,740 A | 8/2000 | Mechoulam |
| 6,187,332 B1 | 2/2001 | Gern |
| 6,234,991 B1 | 5/2001 | Gorsuch |
| 6,482,866 B1 | 11/2002 | Dahayanaka |
| 6,489,308 B1 | 12/2002 | Shapiro |
| 6,500,213 B1 | 12/2002 | Braun |
| 6,656,227 B2 | 12/2003 | Levin |
| 6,790,979 B2 * | 9/2004 | Lee et al. .................. 560/53 |
| 6,831,108 B2 | 12/2004 | Dahanayake |
| 6,866,856 B2 | 3/2005 | Lu |
| 6,884,783 B2 | 4/2005 | Jia |
| 6,900,356 B2 | 5/2005 | Gokaraju |
| 7,025,742 B2 | 4/2006 | Rubenstein |
| 7,205,011 B2 * | 4/2007 | Chen et al. .................. 424/756 |
| 7,351,745 B2 | 4/2008 | Dryer |
| 7,416,559 B2 | 8/2008 | Shalaby |
| 7,462,459 B2 | 12/2008 | Zerangue |
| 7,582,068 B2 | 9/2009 | Koullick |
| 2001/0051184 A1 | 12/2001 | Heng |
| 2002/0019382 A1 | 2/2002 | Snyder |
| 2003/0108628 A1 | 6/2003 | Babish |
| 2003/0147979 A1 | 8/2003 | Mae |
| 2003/0153512 A1 | 8/2003 | Hergenhahn |
| 2003/0157155 A1 | 8/2003 | Lipp |
| 2003/0199594 A1 | 10/2003 | Shah |
| 2004/0127470 A1 | 7/2004 | Masferrer |
| 2004/0127556 A1 | 7/2004 | Lu |
| 2004/0220113 A1 | 11/2004 | Shapiro |
| 2004/0220239 A1 | 11/2004 | Shapiro |
| 2004/0220242 A1 | 11/2004 | Shapiro |
| 2004/0220510 A1 | 11/2004 | Koullick |
| 2005/0020945 A1 | 1/2005 | Tosaya |
| 2005/0031651 A1 | 2/2005 | Gervais |
| 2005/0038371 A1 | 2/2005 | Reich |
| 2005/0164957 A1 | 7/2005 | Jia |
| 2005/0169960 A1 | 8/2005 | Hunter |
| 2005/0169961 A1 | 8/2005 | Hunter |
| 2005/0181005 A1 | 8/2005 | Hunter |
| 2005/0181009 A1 | 8/2005 | Hunter |
| 2005/0181036 A1 | 8/2005 | Aggarwal |
| 2005/0187140 A1 | 8/2005 | Hunter |
| 2005/0267221 A1 | 12/2005 | Wellen |
| 2006/0020329 A1 | 1/2006 | Raze |
| 2006/0067998 A1 * | 3/2006 | Kurzrock et al. ............. 424/450 |
| 2006/0116757 A1 | 6/2006 | Lashinski |
| 2006/0134059 A1 | 6/2006 | Dryer |

(Continued)

FOREIGN PATENT DOCUMENTS

CN  1312106  3/2003

(Continued)

OTHER PUBLICATIONS

Yang et al. Curcumin Inhibits Formation of Amyloid B Oligomers and Fibrils, Binds Plaques, and Reduces Amyloid in Vivo. The Journal of Biological Chemistry, 2005, vol. 280 (7), pp. 5892-5901.*

(Continued)

*Primary Examiner* — Sikarl Witherspoon
(74) *Attorney, Agent, or Firm* — Thomas M. DiMauro M. DiMauro

(57) ABSTRACT

A method of delivering a curcuminoid to a patient, which includes iontophoretically delivering a charged curcuminoid across the skin of an Alzheimer's Disease patient.

10 Claims, 25 Drawing Sheets

U.S. PATENT DOCUMENTS

| | | | |
|---|---|---|---|
| 2006/0134155 | A1 | 6/2006 | Dryer |
| 2006/0134231 | A1 | 6/2006 | Hines |
| 2006/0195142 | A1 | 8/2006 | Shalaby |
| 2006/0224234 | A1 | 10/2006 | Jayaraman |
| 2006/0240007 | A1 | 10/2006 | Sanders |
| 2006/0264423 | A1 | 11/2006 | Wood |
| 2006/0264497 | A1 | 11/2006 | Zeligs |
| 2007/0010435 | A1 | 1/2007 | Frangione |
| 2007/0060644 | A1 | 3/2007 | Vander Jagt |
| 2007/0134305 | A1 | 6/2007 | Zilberman |
| 2007/0224671 | A1 | 9/2007 | Shapiro |
| 2007/0243132 | A1 | 10/2007 | Russell Jones |
| 2007/0281045 | A1 | 12/2007 | Tripp |
| 2008/0051691 | A1 | 2/2008 | Dragoon |
| 2008/0075671 | A1 | 3/2008 | DiMauro |
| 2008/0076821 | A1 | 3/2008 | DiMauro |
| 2008/0082036 | A1 | 4/2008 | Trescony |
| 2008/0090897 | A1 | 4/2008 | Steiner |
| 2008/0153912 | A1 | 6/2008 | Dryer |
| 2008/0160109 | A1 | 7/2008 | Dryer |
| 2008/0175895 | A1 | 7/2008 | Kogure |
| 2008/0213404 | A1 | 9/2008 | Johnson |
| 2008/0241352 | A1 | 10/2008 | Shalaby |
| 2008/0247987 | A1 | 10/2008 | Liggins |
| 2008/0275016 | A1 | 11/2008 | Arbiser |
| 2009/0047371 | A1 | 2/2009 | Turini |
| 2009/0087385 | A1* | 4/2009 | Di Mauro ............ 424/43 |
| 2009/0131850 | A1 | 5/2009 | Geiger |
| 2009/0326275 | A1 | 12/2009 | DiMauro |
| 2010/0087527 | A1 | 4/2010 | Dimauro |
| 2010/0292512 | A1 | 11/2010 | Dimauro |

FOREIGN PATENT DOCUMENTS

| | | |
|---|---|---|
| CN | 1970548 | 11/2008 |
| EP | 504263 | 9/1992 |
| JP | 2000236843 | 9/2000 |
| WO | WO 9008128 | 7/1990 |
| WO | WO 9518606 | 7/1995 |
| WO | WO 0140188 | 6/2001 |
| WO | WO 2004014843 | 2/2004 |
| WO | WO 2008051474 | 5/2008 |
| WO | WO 2008131059 | 10/2008 |
| WO | WO 2009073050 | 6/2009 |
| WO | WO 2009073050 | 10/2009 |

OTHER PUBLICATIONS

Valiveti et al. Intranasal absorbtion of Delta-9-tetrahydrocannabinol and WIN55,212-2 mesylate in rats. European Journal of Pharmaceutics and Biopharmaceutics, 2007, vol. 65, pp. 247-252.*

Park et al. Journal of Natural Products, Sep. 2002, vol. 65 (9), pp. 1227 to 1231.*

Praveen Tyle. Iontophoretic Devices for Drug Delivery. Pharmaceutical Research, 1986, vol. 3 (6), 318-326.*

Office Action mailed Jun. 10, 2009 in pending U.S. Appl. No. 11/534,384.

Response filed by applicant on Sep. 10, 2009 in pending U.S. Appl. No. 11/534,384.

Final Office Action mailed Dec. 24, 2009 in pending U.S. Appl. No. 11/534,384.

Office Action mailed Sep. 17, 2009 in pending U.S. Appl. No. 11/736,278.

Response filed by applicant on Sep. 25, 2009 in pending U.S. Appl. No. 11/736,278.

Final Office Action mailed Dec. 3, 2009 in pending U.S. Appl. No. 11/736,278.

Response filed by applicant on Mar. 3, 2010 in pending U.S. Appl. No. 11/736,278.

Office Action mailed Dec. 17, 2009 in Pending U.S. Appl. No. 12/029,904.

Office Action mailed Sep. 2, 2009 in pending U.S. Appl. No. 12/343,750.

Response filed by applicant on Dec. 2, 2009 in pending U.S. Appl. No. 12/343,750.

Pending Non-Published U.S. Appl. No. 12/359,713, filed Jan. 26, 2009 entitled Methylene Blue-Curcumin Analog for the Treatment of Alzheimer's Disease.

International Search Report dated Jul. 14, 2008 PCT/US08/60569.

International Search Report dated Aug. 27, 2009 PCT/US09/48466.

Pending Non-Published U.S. Appl. No. 12/571,303, filed Sep. 30, 2009 entitled Curcumin Derivatives.

Pending Non-Published U.S. Appl. No. 12/696,588, filed Jan. 29, 2010 entitled Shunt Delivery of Curcumin.

Pending Non-Published U.S. Appl. No. 12/697,503, filed Feb. 1, 2010 entitled Methylene Blue-Curcumin Analog for the Treatment of Alzheimer's Disease.

Abla, "Effect of Charge and Molecular Weight on Transdermal Peptide Delivery of Iontophoresis"; *Pharm. Res*; Dec. 2005; pp. 2069-2078; vol. 22(12).

Alas, "Inhibition of Constitutive STAT3 Activity Sensitizes Resistant Non-Hodgkin's Lymphoma and Multiple Myeloma to Chemotherapeutic Drug-Mediated Apoptosis"; *Clin. Cancer Res.*; Jan. 2003; pp. 316-326; vol. 9(1).

Al-Ghananeem, "Targeted Brain Delivery of 17β-Estradiol Via Nasally Administered Water Soluble Prodrugs"; *AAPS PharmSciTech*; 2002; pp. 1-8; vol. 3(1); article 5.

Allcock, "Polyphosphazenes"; *The Encyclopedia of Polymer Science*; 1988; pp. 31-41; vol. 13; Wiley Intersciences, John Wiley & Sons.

Altomare, "Highly Water-soluble Derivatives of the Anesthetic Agent Propofol: in vitro and in vivo Evaluation of Cyclic Amino Acid Esters"; *Eur. J. Pharm. Sci.*; 2003; pp. 17-26; vol. 20.

Anderson, "Strategies in the Design Solution-Stable, Water-Soluble Prodrugsii: Properties of Micellar Prodrugs of Methylprednisolone"; *Journal of Pharmaceutical Sciences*; 2006; pp. 375-381; vol. 74(4); Wiley-Liss, Inc.

Anderson, "α-Amino Acid Phenolic Ester Derivatives: Novel Water-Soluble General Anesthetic Agents Which Allosterically Modulate $GABA_A$ Receptors"; *J. Med Chem.*; 2001; pp. 3582-3591; vol. 44.

Anekonda, "Resveratrol—A Boon for Treating Alzheimer's Disease?"; *Brain Research Reviews*; 2006; pp. 316-326; vol. 52; Elsevier.

Araujo, "Biologic Activities of *Curcuma longa* L."; *Mem Inst Oswaldo Cruz*; 2001; pp. 723-728; vol. 96(5); Rio De Janeiro.

Atamna, "Methylene Blue Delays Cellular Senescence and Enhances Key Mitochondrial Biochemical Pathways"; *FASEB J.*, Mar. 2008; pp. 703-712; vol. 22(3).

Auld, "Probing Weakly Polar Interactions in Cytochrome"; *Protein Science*; 1993; pp. 2187-2197; vol. 2; Cambridge University Press.

Barakat, "Carbamazepine Uptake into Rat Brain Following Intraolfactory Transport"; *J. Pharm. Pharmacol.*; Jan. 2006; pp. 63-72; 58(1).

Basile, "Curcumin Derivatives: Molecular Basis of Their Anti-Cancer Activity"; *Biochem Pharmacol.*; Jul. 3, 2009; pp. 1305-1315.

Bastianetto, "Neuroprotective Abilities of Reservatol and Other Red Wine Constituents Against Nitric Oxide-related Toxicity in Cultured Hippocampal Neurons"; *Br. J. Pharm.*; 2000; pp. 711-720; vol. 131; Macmillan Publishers Ltd.

Basu, "Differential and Special Properties of the Major Human UGT1-encoded Gastrointestinal UDP-glucuronosyltransferases Enhance Potential to Contain Chemical Uptake"; *J. Biol. Chem.*; 2004; pp. 1429-1441; vol. 279.

Basu, "Evidence for Phosphorylation Requirement for Human Bilirubin UDP-glucuronosyltransferase (UGT1A1) Activity"; *Biochem. Biophys. Res. Comm.*; 2003; pp. 98-104; vol. 303.

Basu, "Human UDP-Glucuronosyltransferases Show Atypical Metabolism of Mycophenolic Acid and Inhibition by Curcumin"; *Drug. Metab. Dispos.*; Jul. 2004; pp. 768-773; vol. 32(7).

Basu, "Phosphorylation of a UDP-glucuronosyltransferase Regulates Substrate Specificity"; *PNAS*; May 3, 2005; pp. 6285-6290; vol. 102(18).

Begum, "Curcumin Structure—Function, Bioavailability and Efficacy in Models of Neuroinflammation and Alzheimer's Disease"; *J. Pharmacol Exp The*; Apr. 16, 2008; pp. 196-208; vol. 326 (1).

Belguendouz, "Reservatol Inhibits Metal Ion-dependent and Independent Peroxidation of Porcine Low-density Lipoproteins"; *Biochemical Pharmacology*; 1997; 1347-1355; vol. 53; Elsevier.

Bender, "Etofenamate Levels in Human Serum and Synovial Fluid Following Iontophoresis"; *Arzneimittelforschung*; 2001; pp. 489-492; vol. 51(6).

Bundgaard, "Water soluble, Solution-stable, and Biolabile n-substituted (aminomethyl) Benzoate Ester Prodrugs of Acyclovir"; *Pharm. Res.*; 1991; pp. 1087-1093; vol. 8 (9).

Castuma, "The Influence of Fatty Acid Unsaturation and Physical Properties of Microsomal Membrane Phospholipids on UDP-glucuronyltransferase Activity"; *Biochem. J.*; 1989; 732-731; vol. 258.

Chavanpatil, "Nasal Drug Delivery of Sumatriptan Succinate"; *Pharmazie*; May 2005; pp. 374-379; vol. 60(5).

Chearwae, "Curcuminoids Purified from Turmeric Powder Modulate the Function of Human Multidry Resistance Protein 1 (ABCC1)"; *Cancer Chemother. Pharmacol.*; 2006; pp. 376-388; vol. 57(3).

Chen, "Curcumin and its Analogues as Potent Inhibitors of Low Density Lipoprotein Oxidation: H-atom Abstraction From the Phenolic Groups and Possible Involvement of the 4-hydroxy-3-methoxyphenyl Groups"; *Free Rad. Biol. Med.*; Feb. 2006; pp. 526-535; vol. 40(3).

Chen, "SIRT1 Protects Against Microglia-dependent Amyloid-B toxicity Through Inhibiting NF-KB Signaling"; *J. Biol. Chem.*; 2005; pp. 40364-40374; vol. 280(48).

Cohn, "Polymer Preprints"; *Journal of Biomaterials Research*; 1989; p. 498; Biomaterials Research Labortatory, Casali Institute of Applied Chemistry, Israel.

Cohn, "Biodegradable PEO/PLA Block Copolymers"; *Journal of Biomedical Materials Research*; 1988; pp. 993-1009; vol. 22; John Wiley & Sons, Inc.

Cole, "Prevention of Alzheimer's Disease: Omega-3 fatty Acid and Phenolic Anti-oxidant Interventions"; *Neurobiol. Aging*; 26S; (2005); S133-S136.

Conjeevaram, "Iontopheretic in vitro transdermal delivery of B-blockers in hairless rats and reduced skin irritation by liposomal formulation"; *Pharm Res.*; Sep. 2003; pp. 1496-1501; vol. 20(9).

Cruz-Correa, "Combination Treatment With Curcumin and Quercetin of Adenomas in Familial Adenomatous Polyposis";*Clin. Gastroent. Hepat.*, 2006; pp. 1035-1038; vol. 4.

Curecurmin Bioresonant Phytotherapeutic Nasal Spray Brochure, Bioonic Phytoceuticals, 2006.

Defelice, "Targeting the Neurotoxic Species in Alzheimer's Disease. Inhibitors of Abeta Oligomerization"; *FASEB J.*; Sep. 2004; pp. 1366-1372; vol. 18(12).

Denet, "Transdermal delivery of timolol and atenolol using electroporation and iontophoresis in combination:a mechanist approach"; *Pharm Res.* Dec. 2003; pp. 1946-1951; vol. 20(12).

Do, "Reverse Pharmacognosy: Application of Selnergy, a New Tool for Lead Discovery. The Example of ϵ-Viniferin"; *Current Drug Disc Tech*; 2005; pp. 161-167; vol. 2.

ElJamel, "ALA and Photofrin Fluorescence-Guided Resection and Repetitive PDT in Glioblastoma Multiforme: A Single Centre Phase III Randomised Controlled Trial"; *Lasers Med Sci*; 2008; pp. 361-367; vol. 23.

El-Mohsen, "Distribution of [3H] trans-reservatol in Rat Tissues Following Oral Administration"; *British J. Nutrition*; 2006; pp. 62-70; vol. 96.

Fang, "Transdermal Iontophoresis of Sodium Nonivamide Acetate V. Combined Effect of Physical Enhancement Methods"; *Int J Pharm.*; Mar. 20, 2002; pp. 95-105; vol. 235(1-2).

Fiala, "Innate Immunity and Transcription of MGAT-III and Toll-like Receptors in Alzheimer's Disease Patients are Improved by Bisdemethoxycurcumin"; *Proc Natl Acad Sci USA.*; Jul. 31, 2007; pp. 12849-12854; vol. 104(31).

Flynn; "Percutaneous Drug Penetration Choosing Candidates for Transdermal Development"; *Drug Dev. Res.*; 1988; pp. 169-185; vol. 13.

Fogler, "Distribution and Fate of free and Liposome-Encapsulated [³H]Nor-Muramyl Dipeptide and [³H]Muramyl Tripeptide Phosphatidylethanolamine in Mice"; *The Journal of Immunology*; 1985; pp. 1372-1377; vol. 135(2);The American Association of Immunologists.

Fotuhi, "Protect Your Brain Against Memory Loss and Alzheimer's Disease" *The Memory Cure*; 2003; pp. 75-128; McGraw-Hill, NY, NY.

Frank, "A Review of Antioxidants and Alzheimer's Disease"; *Ann. Clin. Psychiatry*; Oct.-Dec. 2005; pp. 269-286; vol. 17(4).

Frautschy, "Phenolic Anti-inflammatory Antioxidant Reversal of AB-induced Cognitive Deficits and Neuropathology"; *Neurobiol. Aging*; 2001; pp. 993-1005; vol. 22.

Fukuyama, "Neurotrophic Activity of Honokiol on the Cultures of FetalRrat Cortical Neurons"; *Bioorg Med Chem Lett.*; Apr. 22, 2002; pp. 1163-1166; vol. 12(8).

Fullbeck, "Novel Curcumin- and Emodin-Related Compounds Identified by In Silico 2D/3D Conformer Screening Induce Apoptosis in Tumor Cells"; *BMC Cancer*; 2005; pp. 97; vol. 5.

Geahlen, "Piceatannol (3,4,3',5'-Tetrahydroxy-Trans-Stilbene) is a Naturally Occurring Protein-Tyrosine Kinase Inhibitor"; *Biochem. Biophys. Res. Comm.*, 1989; pp. 241-245; vol. 165(1).

Gesher, "Resveratrol From Red Grapes—Pedestrian Polyphenol or Useful Anticancer Agent?"; *Planta Med.*; Oct. 2008; pp. 1651-1655; vol. 74(13).

Ghosh, "Brain Parenchymal Metabolism of 5-Iodo-2'-Deoxyuridine and 5'-Ester Prodrugs"; *Pharm Res.*; 1992; pp. 1048-1052; vol. 9(8).

Gosslau, "A Methosy Derivative of Reservatrol Analogue Selectively Induced Activation of the Mitochondrial Apoptotic Pathway in Transformed Fibroblasts"; *Brit. J. Can. Res.*; 2005; pp. 513-521; vol. 92; Cancer Research UK.

Gosslau, "Trans- and Cis-Stilbene Polyphenols Induced Rapid Perinuclear Mitochondrial Clustering and P53-Independent Apoptosis in Cancer Cells But Not Normal Cells"; *Eur J Pharmacol.*; Jun. 10, 2008; pp. 25-34; 587(1-3).

Greenwald, "Drug Delivery Ssytems Employing 1,4- or 1,6-Elimination: Poly (ethylene glycol) Prodrugs of Amine-Containing Compounds"; *J. Med. Chem*; 1999; pp. 3657-3667; vol. 42(18).

Guerra ,Video—Clinical Trial University Pennsylvania;2007; http://www.mccormickscienceinstitute.com/content.cfm?id=10464.

Gura, "Hope in Alzheimer's Fight Emerges From Unexpected Places"; *Nature Medicine*; 2008; p. 894; vol. 14.

Gynther, "Large Neutral Amino Acid Transporter Enables Brain Drug Delivery via Prodrugs"; *J. Med. Chem.*; 2008; pp. 932-936; vol. 51.

Han, "Neuroprotective Effects of Reservatol Against B-amylod-induced Neurotoxicity in Rat Hippocampal Neurons: Involvement of Protein Kinase C"; *Br. J. Pharmacology*; 2004; pp. 997-1005; vol. 141.

Han, "Specific Plasma Membrane Binding Sites for Polyphenols; Including Reservatol; in the Rat Brain"; *J. Pharmacol. Exp. Ther.*; Jul. 2006.; pp. 238-245 vol. 318(1); (Epub Mar. 30, 2006).

Hari, "One-Pot Synthesis of 2,3-Disubstituted N-Tosylindoles from o-Acyl-N-tosylanilines"; *Synthesis*; 2006; pp. 1249-1252; No. 8; Georg Thieme Verlag Stuttgart.

Heller, "Poly (Otrho Esters)"; *Handbook of Biodegradable Polymers*; edited by Domb; et al; Hardwood Academic Press; 1997; pp. 99-118.

Hinz, "Percutaneous Penetration of Para-Substituted Phenols in Vitro"; *Fundam. Appl. Toxicol.*; 1991; pp. 575-583; vol. 17; The Society of Toxicology.

Hirpara, "Quercetin and Its Derivatives: Synthesis, Pharmacological Uses With Special Emphasis on Anti-Tumor Properties and Prodrug With Enhanced Bio-Availability"; *Anticancer Agents Med. Chem.*, Feb. 2009., pp. 138-161; vol. 9(2); Bentham Science Publishers.

Holland, The Effects of Cannabinoids on P-glycoprotein Transport and Expression in Multidrug Resistant Sells; *Biochem. Pharmacol.*; 2006; pp. 1146-1154.

Hong, Involvement of Multidrug Resistance-associated Proteins in Regulating Cellular Levels of (-)-epigallocatechin-3-gallate and its Methyl Metabolites; *Biochem. Biophys. Res. Comm.*; Oct. 2003.; pp. 222-227; vol. 310(1).

Horvath, "Novel Resveratrol Derivatives Induce Apoptosis and Cause Cell Cycle Arrest in Prostate Cancer Cell Lines"; *Anticancer Res*; 2007; pp. 3459-3464.

Hossain, "Alternative, East and Efficient Preparation of Poly [4-(diacetoxyiodo)styrene] from Poly(4-iodostyrene) Using Sodium Perborate as the Oxidant"; *Synthesis*; 2006; pp. 1253-1256; No. 8; Georg Thieme Verlag Stuttgart.

Howitz, Small Molecule Activators of Sirtuins Extend Saccaromyces Cerevisiae Lifespan; *Nature*; 2003; pp. 191; vol. 425.

Hur, "Rosmarinic Acid Induces P56lck-Dependent Apoptosis in Jurkat and Peripheral T Cells Via Mitochondrial Pathway Independent From Fas/Fas Ligand Interaction"; *J. Immunology*; 2004; pp. 79-87; vol. 172.

Hussain, "Prodrugs for Improved Oral β-Estradiol Bioavailability"; *Pharm. Res.*; 1988; pp. 44-47; vol. 5(1); Plenum Publishing Corporation.

Hussain, Testosterone 17B-N;N-dimethylglycinate Hydrochloride: A Prodrug With a Potential for Nasal Delivery of Testosterone; *J. Pharm. Sci.*; Mar. 2002; pp. 785-789; vol. 91(3); Wiley-Liss; Inc.

Irie, "Structure of β-amyloid Fibrils and its Relevance to Their Neurotoxicity: Implications for the Pathogenesis of Alzheimer's Disease"; *Journal of Bioscience and Bioengineering*; 2005; pp. 437-447; vol. 99 No. 5.

Ishida, Antitumor Agents; Part 214:X: Synthesis and Evaluation of Curcumin Analogues as Cytotoxic Agents; *Bioorganic and Medicinal Chemistry*; 2002; pp. 3481-3487; vol. 10.

Jean, Structural Elements Regulating Amyloidogenesis: A Cholinesterase Model System; *PLOS One*; 2008; vol. 3(3); e1834.

Jensen, "Water-soluble Aminoalkylbenzoate Esters of Phenols as Prodrugs: Synthesis; Enzymatic Hydrolysis and Chemical Stability of Paracetamol Esters"; *Acta Pharma Nord*; 1991; pp. 31-40; vol. 3(1).

Jeon, "β-secretase (BACE1)-inhibiting Stilbenoids From Smilax Rhizome"; *Phytomedicine*; 2007; pp. 403-408; vol. 14.

John, "Anti-Tumor Studies of Metal Chelates of Synthetic Curcuminoids"; *J. Exp. Clinic. Cancer Res.*; 2002; pp. 219-224; vol. 21.

Kandimalla, "Transport of Hydroxyzine and Triprolidine Across Bovine Olfactory Mucosa: Role of Passive Diffusion in the Direct Nose-to-brain Uptake of Small Molecules"; *International Journal of Pharmaceutics*; 2005; pp. 133-144; vol. 302.

Kao, "Enhancement of the Systemic and CNS Specific Delivery of l-dopa by the Nasal Administration of its Water Soluble Podrugs"; *Pharmaceutical Research*; pp. 2000; 978-984; vol. 17(8).

Kao, "Evaluation of [$^{76}$Br]FBAU 3',5'-dibenzoate as a Lipophilic Prodrug for Brain Imaging"; *Nuclear Medicine and Biology*; 2007; pp. 527-535; vol. 29; Elsevier Science Inc.

Kapoor; "Telomerase Targeted Anticancer Bioactive Prodrug by Antisense-based Approach"; *Cancer Letters*; 2007; pp. 245-250; vol. 248.

Kemnitzer, "Degradable Polymers Derived From the Amino Acid L-Tyrosine"; 1997; pp. 251-272; edited by Domb, et. al., Hardwood Academic Press.

Kim, "Butein Sensitizes Human Leukemia Cells to Apoptosis Induced by Tumor Necrosis Factor-Related Apoptosis Inducing Ligand (TRAIL)"; *Arch. Pharm. Res.*; 2008; pp. 1179-1186; vol. 31(9).

Kim, "Curcuminoids From *Curcuma longa* L. (Zingiberaceae) that Protect PC12 Rat Pheochromocytoma and NormalHuman Umbilical Vein Endothelial Cells From βA(1-42) Insult"; *Neuroscience Letters*; 2001; pp. 57-61; vol. 303.

Kim, "Protective Effects of Piceatannol Against Beta-amyloid-induced Neuronal Cell Death"; *Ann. N.Y. Accad. Sci*; 2007; pp. 473-482; vol. 1095; N.Y. Academy of Sciences.

Kim, "Reservatrol Inhibits Inducible Nitric Oxide Synthase and Cycloozygenase-2 Expression in β-amyloid-treated C6 Glioma Cells"; *International Journal of Molecular Medicine*; 2006; pp. 1069-1075; vol. 17.

Kleindienst, "Effect of Dimethyl Sulfoxide on Blood-brain Barrier Integrity Following Middle Cerebral Artery Occlusion in the Rat"; *Acta Neurochir*; 2006; pp. 258-262; vol. 96; Springer-Verlag; Australia.

Klimowicz, "The Phytochemical Piceatannol Induces the Loss of CBL and CBL-Associated Proteins"; *Mol. Cancer Ther.*, Mar. 2009: pp. 602-614; vol. 8(3).

Kubo, "Nonpeptide Angiotensin II Receptor Antagonists. Synthesis and Biological Activity of Potential Prodrugs of Benzimidazole-7-Carboxylix Acids"; *J. Med. Chem.*; 1993; pp. 2343-2349; vol. 36(16).

Kumar, "Biodegradable Microspheres of Curcumin for Treatment of Inflammation"; *Indian J. Phisiol. Pharmacol*; 2002; pp. 209-217; vol. 46(2).

Kumar, "Design and Synthesis of Curcumin-bioconjugates to Improve Delivery"; *Nucleic Acids Symposium Series*; 2000; pp. 75-76; No. 44.

Kumar, "Syntheses of Curcumin Bioconjugates and Study of Their Antibacterial Activities Against beta-Lactamase-Producing Microorganisms"; *Bioconjug Chem.*; 2001; pp. 464-469; vol. 12(4).

Kurkela, "Expression and Characterization of Recombinant Human UDP-glucuronosyltransferases (UGTs)"; *The Journal of Biological Chemistry*; 2003; pp. 3536-3544; vol. 278(6).

Lai, "Antitumor Effect of Methylene Blue In Vivo"; *Zhonghua Zhong Liu Za Zhi.*; Mar. 1989; pp. 98-100; vol. 11(2).

Lamba, "Imine-bridged Planar Poly(p-phenylene) Derivatives for Maximization of Extended π-conjugation—The Common Intermediate Approach"; *J. Am. Chem.*; 1994; pp. 11723-11736; vol. 116.

Laneri, "Ionized Prodrugs of Dehydroepiandrosterone for Transdermal Iontophoretic Delivery"; *Pharmaceutical Research*; 1999; pp. 1818-1824; vol. 16(12).

Larrosa, "The Grape and Wine Polyphenol Piceatannol is a Potent Inducer of Apoptosis in Human SK-Mel-28 Melanoma Cells"; *Eur. J. Nutr.*, Oct. 2004; pp. 275-284; vol. 43(5).

Lee, "Methylene Blue Induces Cytoxicity in Human Brain Tumor Cells"; *Cancer Letters*; 1995; pp. 141-145; vol. 88(2); Elsevier Science Ireland.

Lee, "A Hybrid Molecule That Prohibits Amyloid Fibrils and Alleviates Neuronal Toxicity Induced by Beta-Amyloid (1-42)"; *Biochem. Biophys. Res. Commun.*; Mar. 25, 2005; pp. 816-823; vol. 328(4).

Lendel, "On the Mechanism of Nonspecific Inhibitors of Protein Aggregation: Dissecting the Interactions of α-Synuclein With Congo Red and Lacmoid"; *Biochemistry*; 2009; pp. A-M.

Li, "2,3',4,4',5'-Pentamethoxy-trans-stilbene, a Resveratrol Derivative, is a Potent Inducer of Apoptosis in Colon Cancer Cells Via Targeting Microtubules"; *Biochemical Pharmacology*; 2009; pp. 1224-1232; vol. 78; Elsevier Inc.

Lim, "The Curry Spice Curcumin Reduces Oxidative Damage and Amyloid Pathology in an Alzheimer Transgenic Mouse"; *J. Neurosci*; 2001; pp. 8370-8377; vol. 21(21).

Lim, "The Curry Spice Curcumin Reducted Oxidative Damage and Amyloid Pathology in an Alzheimer Transgenic Mouse"; *The Journal of Neuroscience*; 2001; pp. 8370-8377; vol. 21(21); Society for Neuroscience.

Limtrakul, "Modulation of human multidrug-resistance MDR-1 gene by natural curcuminoids."; *BMC Cancer.*; Apr. 2004; pp. 1-6; vol. 4(13).

Liu, "Intranasal Administration of the Antioxidant Myricetin Reduces Infarct Volume and Improves Neurologic Function Following Focal Cerebral Ischemia in Rats"; *Neurol.*; 2002; p. A389; vol. 58(Suppl.3).

Liu, "Stimulation of Serotonin Synthesis in Rat Brain After Antiepilepsirine; An Entiepileptic Piperine Derivative"; *Biochemical Pharmacology*; 1984; pp. 3883-3886; vol. 33(23).

Loa, "Studies of Structure-Activity Relationship on Plant Polyphenol-Induced Suppression of Human Liver Cancer Cells"; *Cancer. Chemother. Pharmacol.*; May 2009; pp. 1007-1016; vol. 63(6); Epub Sep. 3, 2008.

Lonsky, "Synthesis and Reactions of Hydroxylated Stilbenes and Their Possible Occurrence as Chromophore Precurson Structures in Lignin"; *Monatshefte fur Chemie*; 1976; pp. 685-695; vol. 107.

Lu, "Preparation of Curcumin Prodrugs and Their In Vitro Anti-Tumor Activities"; *J Huazhong Univ Sci Technolog Med Sci.*; 2005; pp. 668-670, 678; vol. 25(6).

Lu, "Resveratrol analog, 3,4,5,4'-tetrahydroxystilbene, differentially induces pro-apoptotic p53/Bax gene expression and inhibits the grown of transformed cells but not their normal counterparts"; *Carcinogenesis*; 2001; pp. 321-328; vol. 22(2); Oxford University.

Lu, "Resveratrol Analog, 3,4,5,4'-Tetrahydroxystilbene, Differentially Induces Pro-Apoptotic P53/Bax Gene Expression and Inhibits the Growth of Transformed Cells But Not Their Normal Counterparts"; *Carcinogenesis*; Feb. 2001; pp. 321-328; vol. 22(2).

Maher, A Comparison of the Neurotrophic Activities of the Flavenoid Fisetin and Some of its Derivatives; *Free Radical Research*; 2006; pp. 1105-1111; vol. 40(10).

Majumdar, "Curcumin Synergies With Resveratrol to Inhibit Colon Cancer"; *Nutrition and Cancer*; Jul. 2009; pp. 544-553; vol. 61(4).

Mancuso, "Natural antioxidants in Alzheimer's disease"; *Expert Opinion on Investigational Drugs*; Dec. 2007; pp. 1921-1931; vol. 16; No. 12.

Mandelkow, "Structural Principles of Tau and the Paired Helical Filaments of Alzheimer's Disease"; *Brain Pathol.*; 2007; pp. 83-90; vol. 17; International Society of Neuropathology.

Mano, "In Vitro Imhibitory Effects of Non-Steroidal Snti-Inflammatory Drugs on 4-Methylumbelliferone Glucuronidation in Recombinant Human UDP-glucuronosyltransferase 1A9—Protein Inhibition by Nifulmic Acid"; *Biopharm. Drug Dispos.*; Jan. 2006; pp. 1-6; vol. 27; John Wiley & Sons; Ltd.

Marambaud, "Reservatrol Promotes Clearance of Alzheimer's Disease Amyloid-β Peptides"; *J. Biol. Chem.*; 2005; pp. 37377-37382; vol. 280(45); The American Society of Biochemistry and Molecular Biology; Inc.

Mark, "Hydrogels"; *Concise Encyclopedia of Polymer Science and Engineering*; 1990; pp. 458-459; Wiley and Sons.

Mazumder, "Curcumin Analogs with Altered Potencies Against HIV-1 Integrase as Probes for Biochemical Mechanisms of Drug Action"; *J. Med. Chem*; 1997; pp. 3057-3063; vol. 40; The American Chemical Society.

Mickstacka, "Effect of Natural Analogues of Trans-Resveratrol on Cytochromes P4501A2 and 2E1 Catalytic Activities"; *Xenobiotica*; 2006; pp. 269-285.

Mishra, "Design; Development and Synthesis of Mixed Bioconjugates of Piperic Acid-Glycine; Curcumin-Glycine/Alanine and Curcumin-Glycine-Piperic Acid and their Antibacterial and Antifungal Properties"; *Bioorganic & Medicinal Chemistry*; 2005; pp. 1477-1486; vol. 13; Elsevier Ltd.

Mishra, "Differential Apoptotic and Redox Regulatory Activities of Curcumin and its Derivatives"; *Free Rad. Biology & Medicine*; 2005; pp. 1353-1360; vol. 38; Elsevier Inc.

Mulholland, "Pre-Clinical and Clinical Study of QC12; a Water-Soluble; Pro-Drug of Quercetin"; *Annals Oncology*; 2001; pp. 245-248; vol. 12; Kluwer Academic Publishers; Netherlands.

Muller, "The Determination of the Amphiphilic Properties of a Prodrug (DDMS) of Phenytoin in Aqueous Media"; *International Journal of Pharmaceutics*; 1992; pp. 175-186; vol. 86(2-3).

Murakami, "Distance Measurement Between Tyr10 and Met35 in Amyloid β by Site-Directed Spin-Labeling ESR Spectroscopy: Implications for the Stronger Neurotoxicity of Aβ42 than Aβ40"; *ChemBioChem*; 2007; pp. 2308-2314; vol. 8; Wiley-VCH Verlag GmbH & Co. KGaA; Weinheim.

Murtha, "Synthesis of the Cholesteryl Ester Prodrugs Cholesteryl Ibuprofen and Cholesteryl Flufenamate and Their Formulation Into Phospholipid Microemulsions"; *Journal of Pharmaceutical Science*; 1994; pp. 1222-1228; vol. 83(9).

Murthy, "Iontophoretic Drug Delivery Across Human Nail"; *J Pharm Sci.*; 2007; pp. 305-311; vol. 96(2)Wilry-Liss; Inc.

Nakaya, "Plastic Scintillators. II. The Synthesis of Some Distyrylbenzene Derivatives as Wavelength Shifters in Plastic Scintillators"; *Bulletin of the Chemical Society of Japan*; 1966; pp. 1547-1551; vol. 39.

Naganuma, "Turmeric and Curcumin Modulate the Conjugation of 1-Naphthol in Caco-2 Cells"; *Biol. Pharm. Bull.*; Jul. 2006; pp. 1476-1479; vol. 29(7); Pharmaceutical Society of Japan.

Narayanan, "Liposome Encapsulation of Curcumin and Resveratrol in Combination Reduces Prostate Cancer Incidence in PTEN Knockout Mice"; *Int'l J. Cancer*; Feb. 6, 2009; pp. 1-8; vol. 125(1).

Narlawar, "Curcumin Derivatives Inhibit or Modulate Beta-Amyloid Precursor Protein Metabolism"; *Neurodegen. Dis.*; 2007; pp. 88-93; vol. 4; S. Karger AG.

Narlawar, "Curcumin-Derived Pyrazoles and Isoxazoles: Swiss Army Knives or Blunt Tools for Alzheimer's Disease?"; *ChemMedChem Papers*; 2007; pp. 1-9.

Nielsen, "Bioreversible Quaternary N-Acyloxymethyl Derivatives of the Tertiary Amines Bupivacaine and Lidocaine-Synthesis; Aqueous Solubulity and Stability in Buffer; Human Plasma and Simulated Intestinal Fluid"; *Eur.J.Pharm.Sci.*; Apr. 2005;pp. 433-440; vol. 24(5); Elsevier B.V.

Nielsen, "Bioreversible Quaternary N-acyloxymethyl Derivatives of the Poorly Soluble Tertiary Amine Lu 28-179—Synthesis, Pharmaceutical Chemical Characterization and Bioavailability Studies in Dogs"; *European Journal of Pharmaceutical Sciences*; 2005; pp. 421-428; vol. 26; Elsevier B.V.

Neuhouser, "Dietary Flavonoids and Cancer Risk: Evidence From Human Population Studies"; *Nutr. Cancer*, 2004; pp. 1-7; vol. 50(1).

Noller, "Photochemie Elektronenreicher 1,3-Distyrylbenzole"; *Chem Ber.*; 1988; pp. 1609-1615; vol. 121.

Nugroho, "Transdermal Iontophoresis of the Dopamine Agonist 5-OH-DPAT in Human Skin In Vitro"; *J. Controlled Release*; 2005; pp. 393-403; vol. 103; Elsevier B.V.

Oetari, "Effects of Curcumin on Cytochrome P450 and Glutathione S-Transferase Activities in Rat Liver"; *Biochem. Pharmacol.*; Jan. 12, 1996; p. 39-45; vol. 51(1); Elsevier Science Inc.

Okamoto; "Effect of Ionic Strength on Solution Stability of PNU-67590A, a Micellar Prodrug of Methylprednisone"; *Pharmaceutical Research*; 1997; vol. 14(9); Plenum Publishing Corporation.

Ono, "Anti-Parkinsonian Agents Have Anti-Amyloidogenic Activity for Alzheimer's β-Amyloid Fibrils In Vitro"; *Neurochem. Int..*; Mar. 2006; pp. 275-285; 48(4); Elsevier.

Pal, "Non-hydrogen Bond Interactions Involving the Methionine Sulfur Atom"; *Journal of Biomolecular Structure & Dynamics*; 2001; pp. 115-128; vol. 19(1).

Pan, "Biotransformation of Curcmin Through Reduction and Glucuronidation in Mice"; *Drug Metabolism and Disposition*; 1999; pp. 486-494; vol. 27(1); The American Society of Pharmacology and Experimental Therapeutics.

Paradkar, "Characterization of Curcumin-PVP Solid Dispersion Obtained by Spray Drying"; *International Journal of Pharmaceutics*; 2004; pp. 281-286; vol. 271; Elsevier.

Parang, "Synthesis, In Vitro Anti-Human Immunodeficiency Virus Structure-Activity Relationships and Biological Stability of '5-O-Myristoyl Analogue Derivatives of 3'-Azido-2',3'-Dideoxythymidine (AZT) As Potential Prodrugs"; *Antivir Chem Chemother*; 1998; pp. 311-323; vol. 9(4).

Park, "Design and Synthesis of Small Chemical Inhibitors Containing Different Scaffolds for Lck SH2 Domain"; *Bioorg Med Chem Lett.*; Oct. 20, 2003; pp. 3455-3459; vol. 13(20).

Park, "Discovery of Natural Products from *Curcuma longa* that Protect Cells from beta-amyloid Insult: A Drug Discovery Effort Against Alzheimer's Disease"; *Journal of Natural Products*; 2002; pp. 1227-1231; vol. 65(9); American Chemical Society and American Society of Pharmacognosy.

Park, "Discovery of Natural Products from *Curcuma longa* that Protect Cells from Beta-Amyloid Insilt: A Drug Discovery Effort Against Alzheimer's Disease"; *Journal of Natural Products*; Sep. 2002; pp. 1227-1231; vol. 65(9).

Pinho, "The role of N-acetylglucosaminyltransferase III and V in the post-transcriptional modifications of *E-cadherin*"; *Hum Mol Genet.*; Jul. 15, 2009; pp. 2599-2608; vol. 18(14); Epub Apr. 29, 2009.

Pop, "Derivatives of Dexanabinol. I. Water-Soluble Salts of Glycinate Esters"; *Pharmaceutical Research*; 1996; pp. 62-69; vol. 13(1); Plenum Publishing Corporation.

Pop, "Derivatives of Dexanabinol. II. Salts of Amino Acid Esters Containing Tertiary and Quaternary Heterocyclic Noitrogen with Increased Water-Solubility"; *Pharmaceutical Research*; 1996; pp. 469-475; vol. 13(3); Plenum Publishing Corporation.

Pop, "In Vitro and In Vivo Study of Water-Soluble Prodrugs of Dexanabinol"; *Journal of Pharmaceutical Sciences*; 1999; pp. 1156-1160; vol. 88(11); American Chemical Society and American Pharmaceutical Association.

Purkayastha, "Curcumin Blocks Brain Tumor Formation"; *Brain Research*; 2009; pp. 130-138; 1266.

Qasem, "Kinetics of Paclitaxel 2'-N-Methylpyridinium Mesylate Decomposition"; *AAPS PharmSciTech*; 2003; vol. 4(2).

Qin, "Neuronal SIRT1 Activation as a Novel Mechanism Underlying the Prevention of Alzheimer Disease Amyloid Neuropathology by Calorie Restriction"; *Journal of Biological Chemistry*; 2006; pp. 21745-21754; vol. 281(31).

Rajakumar, "Synthesis of New Photoresponsive Stilbene Dendrons and Dendrimers"; *Synthesis*; 2006; pp. 1257-1262; No. 8.

Ramsewak, "Cytotoxicity, Antioxidant and Anti-Inflammatory Activities of Curcumins I-III From *Curcuma longa*"; *Phytomedicine*; 2000; pp. 303-308; vol. 7(4).

Reen, "Impairment of UDP-Glucose Deydrogenase and Glucuronidation Activities in Liver and Small Intestine of Rat and Guinea Pig In Vitro by Piperine"; *Biochemical Pharmacology*; 1993; pp. 229-238; vol. 46(2); Pergamon Press Ltd.

Reinke, "Structure-activity Relationships of Amyloid Beta-aggregation Inhibitors Based on Curcumin: Influence of Linker Length and Flexibility"; *Chem Biol Drug Des*; 2007; pp. 206-215; vol. 70; The Authors Journal Compilation; Blackwell Munksgaard.

Riviere, "New Polyphenols Active on β-amyloid Aggregation"; *Bioorganic & Medicinal Chemistry Letters*; 2008; pp. 828-831; 18.

Romiti, "Effects of Curcumin of P-Glycoprotein in Primary Cultures of Rat Hepatocytes"; *Life Sciences*; 1998; pp. 2349-2358; vol. 62(25); Elsevier Science Inc.

Roughley, "Experiments in the Biosynthesis of Curcumin"; *J. Chem. Soc. Perkin Trans*. 1; 1973; pp. 2379-2388.

Ruan, "Improving the Solubility of Ampelopsin by Solid Dispersions and Inclusion Complexes"; *J. Pharm Biomed. Anal*; Jul. 1, 2005; pp. 457-464;vol. 38(3); Elsevier B.V.

Rubin; "Recent Advances in Cyclopropene Chemistry"; *Synthesis*; 2006; pp. 1221-1245; No. 8; Georg Thieme Verlag Stuttgart.

Safavy, "Design and Development of Water-Soluble Curcumin Conjugates as Potential Anticancer Agents"; *J Med Chem*; 2007; pp. 6284-6288.

Savaskan, "Red Wine Ingredient Reservatrol Protects from β-Amyloid Neurotoxicity"; *Gerontology*; Nov. 2003; pp. 380-383; vol. 49; Karger AG; Basel.

Scheld, "Drug Delivery to the Central Nervous System: General Principles and Relevance to Therapy for Infections of the Central Nervous System"; *Rev. Infect. Dis.*; 1989; pp. S1669-S1690; vol. 11(7); The University of Chicago.

Selvam, "Design; Synthesis; Biological Evaluation and Molecular Docking of Curcumin Analogues as Antioxidant; Cyclooxygenase Inhibitory and Anti-inflammatory Agents"; *Bioorg. & Medic. Chem. Letter*; 2005; pp. 1793-1797; 15; Elsevier Ltd.

Seow, "Piceatannol, a Syk-Selective Tyrosine Kinase Inhibitor, Attenuated Antigen Challenge of Guinea Pig Airways In Vitro"; *Eur.J. Pharm.*, 2002; 189.

Shamsi, "Glycine-based Polymeric Surfactants with Varied Polar Head Group:II. Chemical Selectivity in Micellar electrokinetic Chromatography Using Linear Salvation Energy Relationships"; *Electrophoresis*; 2005; pp. 4138-4152; vol. 26; Wiley-VCH Verlag GmbH & Co. KGaA; Weinheim.

Sharma, "Phase I Clinical Trial of Oral Curcumin: Biomarkers of Systemic Activity and Compliance"; *Clin. Cancer Res.*; Oct. 15, 2004; pp. 6847-6854; 10; American Association of Cancer Research.

Shen, "Curcumin Surfactant as Anticancer Prodrugs and Drug Carriers"; *AlChE*; 2009.

Shoba, "Influence of Piperine on the Pharmacokinetics of Curcumin in Animals and Human Volunteers"; *Planta Med.*; May 1998; pp. 353-356; Phanta Medica.

Silva, "Potential Tuberculostatic Agents: Micelle-Forming Copolymer Poly(ethylene glycol)-Poly(aspartic acid) Prodrug with Isoniazid"; *Arch Pharm. Pharm. Med. Chem.*; 2001; pp. 189-192; Wiley-VCH Verlag GmbH.

Simoni, "Stilbene-Based Anticancer Agents: Resveratrol Analogues Active Toward HL60 Leukemic Cells With a Non-Specific Phase Mechanism"; *Bioorg Med Chem Lett.*; Jun. 15, 2006; pp. 3245-3248; vol. 16(12).

Stites; "Protein-Protein Interactions: Interface Structure; Binding Thermodynamics; and Mutational Analysis"; *Chem. Rev.*; 1997; pp. 1233-1250; vol. 97; The American Chemical Society.

Takata, "Novel d-γ-tocopherol derivative as a prodrug for d-γ-tocopherol and a two-step Prodrug for S-γ-CEHC"; *J. Lipid Res.*; 2002; pp. 2196-2204; vol. 43; Lipid Research; Inc.

Takata, "Vitamin K Prodrugs: 1. Synthesis of Amino Acid Esters of Menahydroquinone-4 and Enzymatuc Reconversion to an Active Form"; *Pharm. Res.*; 1995; pp. 18-23; vol. 12(1).

Takatsuka, "Synergistic Absorption Enhancement of Salmon Calcitonin and Reversible Mucosal Injury by Applying a Mucolytic Agent and a Non-ionic Surfactant"; *Int. J. Pharm.*; Jun. 2006; pp. 124-130; vol. 316; Elsevier B.V.

Taniguchi, "Inhabitation of Heparin-induced Tau Filament Formation by Phenothiazines, Polyphenols, and Porphyrins"; *J. Biol. Chem.*; 2005; pp. 7614-7623; vol. 280(9); The American Society for Biochemistry and Molecular Biology; Inc.

Tatko, "Investigation of the Nature of the Methionine-π interaction in β-hairpin Ppeptide Model Systems"; *Protein Science*; 2004; pp. 2515-2522; vol. 13; Protein Science.

Thapliyal, "Inhibition of Cytochrome P450 Isozymes by Curcumins In Vitro and In Vivo"; *Food Chem. Toxicol.*; Jun. 2001; pp. 541-547; vol. 39; Elsevier Science Ltd.

Tong, "Apoptosis-inducing Effects of Curcumin Derivatives in Human Bladder Cancer Cells"; *Anti-Cancer Drugs*; 2006; pp. 279-287; vol. 17.

Tonnesen, "Solubility, Chemical and Photochemical Stability of Curcumin in Surfactant Solutions. Studies of Curcumin and Curcuminoids, XXVIII"; *Pharmazie*; 2002; pp. 820-824; vol. 57(12).

Trapani, "Water-soluble Salts of Aminoacid Esters of the Anaesthetic Agent Propofol"; *Intl. J. Pharm.*; 1998; pp. 195-204; vol. 175; Elsevier Science B.V.

Uchino, "Transport of Amino Acid-Related Compounds Mediatied by L-Type Amino Acid Transporter 1 (LAT1): Insights Into the Mechanisms of Substrate Recognition"; *Molecular Pharmacology*; 2002; pp. 729-737; vol. 6(4); The American Society for Pharmacology.

Van Der Logt, "Induction of Rat Hepatic and Intestinal UDP-Glucuronosyltransferases by Naturally Occurring Dietary Anticarcinogens"; *Carcinogenesis*; 2003; pp. 1651-1656; vol. 24(10); Oxford University Press.

Vandorpe, "Biodegradable Polyphosphazenes for Biomedical Applications"; *Handbook of Biodegradable Polymers*; 1997; pp. 161-182; Hardwood Academic Press.

Vareed, "Pharmacokinetics of Curcumin Conjugate Metabolites in Healthy Human Subjects"; *Cancer Epidemiol Biomarkers Prev.* ;2008; pp. 1411-1417; vol. 17(6); American Association for Cancer Research.

Vitaglione, "Bioavailability of Trans-reservatrol From Red Wine in Humans"; *Mol. Nutr. Food Res.*; 2005; pp. 495-504; vol. 49; Wiley-VCH Verlag GmbH & Co. KGaA; Weinheim.

Volak, "Curcuminoids Inhibit Multiple Human Cytochromes P450; UDP-Glucuronosyltransferase; and Sulfotransferase Enzymes; Whereas Piperine is a Relatively Selective CYP3A4 Inhibitor"; *Drug Metabolism and Disposition* ;2008; pp. 1594-1605; vol. 36(8).

Walsh, "Certain Inhibitors of Synthetic Amyloid Beta-Peptide (Abeta) Fibrillogenesis Block Oligomerization of Natural Abeta and Thereby Rescue Long-Term Potentiation"; *J. Neuroscience*; 2005; pp. 2455-2462; vol. 25(10).

Wang, "Reservatrol Protects Against Global Cerebral Ischemic Injury in Gerbils"; *Brain Research*; 2002; pp. 439-447; vol. 958; Elsevier Science B.V.

Wang, "Trial of Antiepilepsirine (AES) in Children with Epilepsy; *Brain & Development*"; 1999; pp. 36-40; vol. 21; Elsevier Science B.V.

Wenzel, "Metabolism and Bioavailability of Trans-reservatrol"; *Mol. Nutr. Food Res.*; 2005; pp. 472-481; vol. 49; Wiley-VCH Verlag GmbH & Co. KGaA; Weinheim.

Wieder, "Piceatannol, a Hydroxylated Analog of the Chemopreventive Agent Resveratrol, is a Potent Inducer of Apoptosis in the Lymphoma Cell Line BJAB and in Primary, Leukemic Lymphoblasts"; *Leukemia*; Nov. 2001; pp. 1735-1742; vol. 15(11).

Wischik, "Selective Inhibition of Alzheimer's Disease-like Tau Aggregation by Phenothiazines"; *Proc. Natl. Acad. Sci.*; 1996; pp. 11213-11218; vol. 93.

Wong, "Glucuronidation of 3-0 Methylnoradrenaline;Harmalol and some Related Compounds"; *Biochem J*; 1996; pp. 99-104; vol. 110; Great Britain.

Wortelboer, "Interplay Between MRP Inhibition and Metabolism of MRP Inhibitors: The Case of Curcumin"; *Chem. Res. Toxicol.*; 2003; pp. 1642-1651; vol. 16; American Chemical Society.

Yang "Curcumin Inhibits Formation of Amyloid β Oligomers and Fibrils, Binds Plaques, and Reduces Amyloid In Vivo"; *J. Biol. Chem*; Feb. 2005; pp. 5892-5901; vol. 280(7).

Yang, "Design and Synthesis of Compounds That Extend Yeast Replicative Lifespan"; *Aging Cell*; 2007; pp. 35-43; vol. 6.

Yarovenko, "A Convenient Synthesis of N-Substituted 2-Thioxo-1, 3-thiazolidin-4-ones"; *Synthesis*; 2006; pp. 1246-1248; No. 8; Georg Thieme Verlag Stuttgart.

Yodkeeree, "Curcumin, Demethoxycurcumin and Bisdemethoxycurcumin Differentially Inhibit Cancer Cell Invasion Through the Down-Regulation of MMPs and uPA"; *J. Nutr. Bio.*; 2009; pp. 87-95; vol. 20(2).

Zatta, "Deposition of Aluminum in brain tissues of rats exposed to inhalation of aluminum acetylacetonate"; *Neuroreport*; 1993; pp. 1119-1122; vol. 4(9).

Zauhar, "Evidence for a Strong Sulfur-Aromatic Interaction Derived From Crystallographic Data"; *Biopolymers*; 2000; pp. 233-248; vol. 53; John Wiley & Sons; Inc.

Zhou, "Herbal Modulation of P-Glycoprotein"; *Drug Metab. Rev.*; Feb. 2004; pp. 57-104; vol. 36(1); Marcel Dekker; Inc.

Ziora, "Small-sized BACE1 Inhibitors"; *Drugs of the Future*; 2006; pp. 53-63; vol. 31(1).

Roh, "Sinonasal Distribution of Nasal Drops and Spray According to Head Positions"; *Journal of Korean Otolaryngal Head Neck Surgery*; 2004; pp. 736-740; vol. 47(8).

Giroux, "Nasal Drug Deposition-Controlled Particle Dispersion: Applying Vertical Flow to Optimize Nasal Drug Deposition"; *Drug Delivery Technology*; Mar. 2005; pp. 44-49.

Liu, "Curcumin Potently Blocks Kv1.4 Potassium Channels"; *Biochem Biophys. Res. Commun.*; Jun. 2006; pp. 1-9; vol. 344(4).

Kozarsky, "Gene Therapy for Cardiovascular Disease"; *Current Opinion in Pharmacology*; 2001; pp. 197-202; vol. 1.

Liu, "Design, Synthesis and Primary Evaluation on Curcumin Derivative Prodrugs of Antitumor"; *Zhongguo Yaoshi*, 2005; pp. 543-545.

Sahelian, "Prostaglandin"; 2006; 5 pages, http://web.archive/org/web/20060801509512/http:www.raysahelian.com/prostaglandin.html.

Bathram, "Effects of Ligand Topology on the Properties of Dinuclear Ruthenium Complexes of Bis-semiquinone Bridging Ligands"; *Inorganica Chimica Acta*; 1998; pp. 1-5; vol. 267.

Valiveti, "Intranasal Absorbtion of Delta-9-Tetrahydrocannabinol and EIN55,212-2 Mesylate in Rats"; *European Journal of Pharmaceutics and Biopharmaceutics*; 2007; pp. 247-252; vol. 65.

Tyle, "Iontophoretic Devices for Drug Delivery"; *Pharmaceutical Research*; 1986; pp. 318-326; vol. 3, No. 6.

Pedersen, "Thermal Assembly of a Biomimetic Mineral/collagen Composite"; 2003; pp. 4881-4890; vol. 24.

Flonase, Get the Best Results with proper usage,Oct, 27, 2003, http://www.flonase.come/use/howto.html, last accessed Sep. 13, 2010, pp. 1-4.

Office Action mailed Mar. 22, 2010 in pending U.S. Appl. No. 11/736,278.

Response filed by applicant on Jun. 22, 2010 in pending U.S. Appl. No. 11/736,278.

Final Office Action mailed Jul. 14, 2010 in pending U.S. Appl. No. 11/736,278.

Response filed by applicant on Oct. 14, 2010 in pending U.S. Appl. No. 11/736,278.

Final Office Action mailed Dec. 9, 2010 in pending U.S. Appl. No. 11/736,278.

Response filed by applicant on Mar. 9, 2011 in pending U.S. Appl. No. 11/736,278.

Supplemental Response filed by applicant on Apr. 13, 2011 in pending U.S. Appl. No. 11/736,278.

Response filed by applicant on Mar. 17, 2010 in pending U.S. Appl. No. 12/029,904.

Final Office Action mailed Jun. 1, 2010 in Pending U.S. Appl. No. 12/029,904.

Response filed by applicant on Sep. 1, 2010 in pending U.S. Appl. No. 12/029,904.

Office Action mailed Sep. 27, 2010 in Pending U.S. Appl. No. 12/029,904.

Response filed by applicant on Apr. 14, 2011 in pending U.S. Appl. No. 12/029,904.

Amendment after allowance filed by applicant Apr. 22, 2010 in pending U.S. Appl. No. 12/343,750.

Preliminary Amendment filed by the applicant on Dec. 15, 2010 for U.S. Appl. No. 12/571,303.

Response filed by applicant on Mar. 24, 2010 in pending U.S. Appl. No. 11/534,384.

Office Action mailed Apr. 7, 2010 in pending U.S. Patent Application Serial No. 11/534,384.

Response filed by applicant on Jul. 10, 2010 in pending U.S. Appl. No. 11/534,384.

Final Office Action mailed Aug. 9, 2010 in pending U.S. Appl. No. 11/534,384.

Response filed by applicant on Nov. 9, 2010 in pending U.S. Appl. No. 11/534,384.

Non-final Office Action mailed Dec. 1, 2010 in pending U.S. Appl. No. 11/534,384.

Response filed by applicant on Mar. 1, 2011 in pending U.S. Appl. No. 11/534,384.

Pending Non-Published Patent Application No. 12/956306 filed entitled Methylene Blue—Curcumin Analog for the Treatment of Alzheimer's Disease Nov. 30, 2010.

International Search Report and Written Opinion dated Feb. 3, 2010 for PCT/US09/67275.

International Search Report dated Apr. 20, 2010 for PCT/US10/21968.

Kaewnopparat, "Increased Solubility, Dissolution and Physicochemical Studies of Curcumin-Polyvinylpyrrolidone K-30 Solid Dispersions", World Academy of Science, Engineering and Technology, 2009, pp. 229-234, vol. 55.

Kissinger, "Crystal Structure of Human ABAD/HSD10 with a Bound Inhibitor: Implications for Design of Alzheimer's Disease Therapeutics"; J. Mol. Biol.; 2004; pp. 943-952; vol. 342; Elsevier.

Kurien, "Improving the Solubility and Pharmacological Efficacy of Curcumin by Heat Treatment", Assay Drug Dev. Technol., 2007, pp. 567-76, vol. 5(4).

Leung, "Encapsulation of Curcumin in Cationic Micelles Suppresses Alkaline Hydrolysis", Langmuir, 2008, pp. 5672-5675, vol. 24.

Salmaso, "New Cyclodextrin Biconjugates for Active Tumour Targeting", Journal of Drug Targeting, 2007, pp. 379-390, vol. 15, Issue 6.

Sui, "Inhibition of the HIV-1 and HIV-2 Proteases by Curcumin and Curcumin Boron Complexes"; Bioroganic & Medicinal Chemistry; 1993; pp. 415-422; vol. 1; No. 6; Pergamor Press Ltd.; Great Britain.

\* cited by examiner (15)

(21)

(16)

(22)

(17)

(23)

(18)

(19)

(20)

(24)

(29)

(25)

(30)

(26)

(27)

(28)

(31)

(32)

(33)

(34)

Curcumin

Curcumin-resveratrol I

Resveratrol

Curcumin-resveratrol II

Curcumin resveratrol I

Curcumin-resveratrol II

Curcumin

Resveratrol

Curcumin-resveratrol

Resveratrol-circumin

Curcumin

Resveratrol

Curcumin-resveratrol III

Curcumin-oxy resveratrol II

Curcumin

Oxy resveratrol

Curcumin-piceatannol

Curcumin

BDMC

Resveratrol

→ BDMC-resveratrol

Curcumin

Piceatannol

Curcumin-Piceatannol

Curcumin 3,3',4'
Fisetin

Curcumin-fisetin

Bisdemethoxy-Curcumin (BDMC)

Honokiol

BDMC - Honokiol

Bisdemethoxy-
Curcumin
(BDMC)

$$\xrightarrow{\text{dimethoxyethane}}$$

$$\xrightarrow{\text{TiCl}_4, \text{NaBH}_4}$$

BDMC - Honokiol

→ dimethoxyethane

→ $TiCl_4$, $NaBH_4$ $$\xrightarrow{\text{dimethoxyethane}}$$
$$\xrightarrow{\text{TiCl}_4, \text{NaBH}_4}$$

IONTOPHORETIC DELIVERY OF CURCUMIN AND CURCUMIN ANALOGS FOR THE TREATMENT OF ALZHEIMER'S DISEASE

BACKGROUND OF THE INVENTION

In Alzheimer's Disease (AD), the abnormal cleavage of beta amyloid protein precursor from the intracellular membrane often produces a protein Aβ 1-42 which is incompletely removed by normal clearance processes. It has been reported that soluble beta amyloid oligomers are highly neurotoxic. Moreover, over time, this soluble protein assemblage is deposited as a beta amyloid protein Aβ plaque within brain tissue, leading to the local destruction of neurons. The Aβ plaque deposition is also believed to provoke an inflammatory response by microglia and macrophages, which recognize the plaque as a foreign body. These cells are believed to respond to the plaque deposition by releasing pro-inflammatory cytokines and reactive oxygen species (ROS). Although the inflammatory response may be provoked in an effort to clear the brain tissue of the detrimental plaque, it is now believed that this inflammation also injures local neuronal tissue, thereby exacerbating AD. Soluble oligomers of beta amyloid or "ADDLs" are a neurotoxic species implicated in AD pathogenesis. Yang, *J. Biol. Chem.*, 280, 7, Feb. 18, 2005, 5892-5901.

In the book "The Memory Cure" (2003, McGraw-Hill, NY, N.Y.), Dr. Majid Fotuhi writes: "Pharmaceutical companies in search of magic drugs to treat Alzheimer's Disease need to pay close attention to curcumin."

It has been reported that 0.1-1.0 μM curcumin inhibits the in vitro formation of amyloid beta oligomers, and blocks the in vitro toxicity of $A\beta_{1-42}$ oligomers in differentiated neuroblastoma cells. Yang, *J. Biol. Chem.*, 280, 7, Feb. 18, 2005, 5892-5901. Curcumin also reduced the amount of soluble beta amyloid by 43% when provided in the diet of Alzheimer's Transgenic mice in a low dose of 160 ppm. Lim, *J. Neurosci.*, 2001, Nov. 1, 21(21) 8370-7.

It appears that curcumin also beneficially reduces deposits of beta amyloid. In middle aged female Sprague-Dawley rats, 500 ppm dietary curcumin reduced amyloid beta deposits induced by beta amyloid infusion by about 80%. Frautschy, *Neurobiol. Aging*, 22, 2001, 993-1005. Curcumin also reduced beta amyloid plaque burden by about 30-40% when provided in the diet of Alzheimer's Transgenic mice in a low dose of 160 ppm. Lim, *J. Neurosci.*, 2001, Nov. 1, 21(21) 8370-7. This is advantageous because it is believed that the oxidative and inflammatory damage caused by AD is linked to microglial response to amyloid beta deposits.

In addition to its beneficial action against soluble beta amyloid, curcumin has considerable anti-oxidative properties and also inhibits the expression of pro-inflammatory cytokines. Frank, *Ann. Clin. Psychiatry*, 2005, Oct.-Dec. 17, 4, 269-86, and Cole, *Neurobiol. Aging*, 26S(2005) S133-S136.

Because curcumin is able to effectively act against many targets of AD, it has been hypothesized that the 4.4 fold lower incidence of AD in the Indian population between the ages of 70 and 79 is due to the high dietary consumption of curcumin. Lim, *J. Neuroscience*, Nov. 1, 2001, 21(21) 8370-77. In those aged 80 years and older, age-adjusted Alzheimer's prevalence in India is roughly one-quarter the rates in the United States (4% versus 15.7%). Frautschy, *Neurobiol. Aging*, 22, 2001, 993-1005. Curcumin has been identified in review articles as one of the most promising candidates for long term AD study. Frank, *Ann. Clin. Psychiatry*, 2005, Oct.-Dec. 17, 4, 269-86, and Cole, *Neurobiol. Aging*, 26S(2005) S133-S136. Curcumin is currently the subject of an FDA approved IND clinical trial at the UCLA Alzheimer Center in the treatment of mild to moderate AD patients. Cole, *Neurobiol. Aging*, 26S(2005) S133-S136.

Because the above-mentioned in vivo effects of curcumin upon AD symptoms were achieved by providing curcumin in the diet, it appears that curcumin is effectively able to cross the blood brain barrier. As curcumin is highly lipophilic, it is expected to easily cross the blood brain barrier. Frautschy, *Neurobiol. Aging*, 22, 2001, 993-1005. Indeed, it has been reported that in vivo studies show that curcumin injected peripherally into aged Tg mice crossed the blood brain barrier and bound amyloid plaques. Yang, *J. Biol. Chem.*, 280, 7, Feb. 18, 2005, 5892-5901.

SUMMARY OF THE INVENTION

Despite the beneficial effects of curcumin, the present inventors have noted that there are many bioavailability problems associated with the oral delivery of curcumin.

First, because curcumin does not easily penetrate the human digestive tract and is subject to intestine-based metabolism and rejection, less than 1% of oral curcumin enters the plasma. Second, the small amount of curcumin that enters the bloodstream is rapidly metabolized by the liver and kidney. Therefore, although curcumin is highly lipophilic (and so easily crosses the blood brain barrier), only very small amounts of orally administered curcumin are registered in the serum and in the brain tissue. One study found that ingesting up to 3.6 g of curcumin per day produced a plasma curcumin level in the range of only about 10 nM. Sharma, Clin. Cancer Res., 2004, Oct. 15, 10(20) 6847-54. A second study found that ingesting up to 6-8 g of curcumin per day produced a peak serum level in the range of about 0.51-1.77 μM. Third, it has been reported that high oral doses of curcumin in the range of 4,000-8,000 mg/day cause problems such as headache, rash and diarrhea, likely produced by metabolites of curcumin. Accordingly, it appears that the above cited plasma curcumin concentrations (10 nM-1.77 μM) represent the practical upper limit of oral dosing of curcumin. Yang, supra, concludes that higher >(5 μM) concentrations of curcumin are not likely to occur in the brain with oral dosing. In fact, Wang reports that injection of 30 mg/kg of curcumin results in a peak curcumin concentration in brain tissue of only about 0.15 ng/mg, which is about 0.40 uM.

Moreover, patient safety concerns have recently been raised due to the ability of oral curcumin to disable the drug-metabolizing enzyme systems in the gut and liver of the patient: "Based on these data and expected tissue concentrations of inhibitors, we predict that an orally administered curcuminoid/piperine combination is most likely to inhibit CYP3A, CYP2C9, UGT, and SULT metabolism within the intestinal mucosa." Volak, *Drug Metab Dispos.* 2008 May 14. Another investigator has concluded that "(t)aken together, the potential beneficial effects of natural antioxidants cannot justify the actual risk of severe side effects as well as the milder possibility of a 'no effect'." Mancuso, "Natural antioxidants in Alzheimer's disease". *Expert Opinion on Investigational Drugs*. December 2007, Vol. 16, No. 12, Pages 1921-1931.

It appears that, in the brain tissue concentration range about 1 uM, some but not all of the beneficial therapeutic qualities of curcumin are realized. For example, it has been reported that 0.1-1.0 μM curcumin inhibits the in vitro formation of amyloid beta oligomers, and blocks the in vitro toxicity of $A\beta_{1-42}$ oligomers in differentiated neuroblastoma cells. Yang, *J. Biol. Chem.*, 280, 7, Feb. 18, 2005, 5892-5901. However, there also appear to be a number of AD-related therapeutic qualities of curcumin that are only realized at higher curcumin concentrations. For example, Yang reports that whereas 0.25-4 uM concentrations of curcumin only minimally prevent the formation of toxic beta amyloid oligomer formation in vitro, 16-64 uM concentrations of curcumin completely prevent the formation of toxic beta amyloid oligomer formation. Yang also notes that curcumin has the potential to inhibit copper binding of beta amyloid, but concludes that it is not clear whether curcumin's avidity for copper and potential concentration in the brain will be enough to directly alter CNS beta amyloid metal binding.

The present invention relates to the intranasal administration of a formulation comprising an effective amount of curcumin. In particular, the present invention relates to the intranasal administration of a formulation comprising an effective amount of curcumin to the olfactory mucosa across the cribriform plate and into the brain in order to treat a neurodegenerative disease, such as AD.

The objective of the present invention is to improve curcumin brain bioavailability by administering curcumin via the nasal route in order to deliver curcumin through the olfactory mucosa and to the brain, and to reduce the dose required for its beneficial effect. As curcumin is highly lipophilic, it will easily pass through the olfactory mucosa located high in the nasal cavity, and enter olfactory neurons and thereby the brain. This mode of delivery will also pass less curcumin into the circulation, and so will result in lower plasma concentrations of metabolites of curcumin, and therefore fewer side effects. Intranasal delivery will improve drug bioavailability to the brain by passive diffusion through the olfactory mucosa, thereby avoiding extensive hepatic first-pass metabolism which significantly lowers the plasma and brain concentrations of curcumin administered orally. Therefore, small doses of curcumin can be administered which will result in fewer side effects, and the drug will be more tolerable and more effective. Lipophilic drugs such as curcumin generally achieve higher brain levels after intranasal administration than after oral or intravenous administration. Therefore, the nasal route of administration of curcumin may help to enhance the effectiveness of curcumin in the brain (the site of action). Additionally, as curcumin is heavily metabolized by the liver, administration by the nasal route may help to reduce drug interactions with other drugs that are also extensively metabolized by the liver. Lastly, because intranasally administered curcumin will passively diffuse through the olfactory mucosa and into the olfactory bulb, which is connected to the hippocampus and amygdala through the limbic system, it is believed that intranasal administration of curcumin will preferentially deposit in the hippocampus and amygdala portions of the brain. These regions are believed to be origination sites of Alzheimer's Disease.

Therefore, in accordance with the present invention, there is provided a method for administering curcumin to a brain of a mammal, comprising:
   a) applying a pharmaceutical composition comprising curcumin to an upper third of a nasal cavity of the mammal, wherein the curcumin is absorbed through an olfactory mucosa and transported to the brain of the mammal.

DESCRIPTION OF THE FIGURES

FIG. 2 discloses the structures of curcumin, resveratrol, and two curcumin-resveratrol hybrids. Note how each of the hybrids retains the interphenolic spacing of each of curcumin and reveratrol.

FIG. 3 discloses a method of making the curcumin-resveratrol I hybrid.

FIG. 4 discloses a method of making the curcumin-resveratrol II hybrid.

FIG. 5 discloses a method of making a curcumin-resveratrol hybrid having three hydroxyl groups in each of the central phenolic group and lateral phenolic groups.

FIG. 6 discloses curcumin, resveratrol and a hybrid thereof, wherein all of the phenolics of the natural compounds are represented in the hybrid, providing trihydroxyl lateral phenolic groups and a dihydroxyl central phenolic group.

FIG. 7 discloses a method of making the curcumin-resveratrol hybrid of FIG. 6.

FIG. 8 is similar to the hybrid of FIG. 6, but wherein the methoxy groups of the base curcumin molecule are retained.

FIG. 9 discloses curcumin, oxyresveratrol and a hybrid thereof, wherein all of the hydroxyls/phenolics of the natural compounds are represented in the hybrid, providing trihydroxyl lateral phenolic groups and a trihydroxyl central phenolic group.

FIG. 10 discloses curcumin, piceatannol and a hybrid thereof, wherein all of the hydroxyls/phenolics of the natural compounds are represented in the hybrid, providing trihydroxyl lateral phenolic groups and a trihydroxyl central phenolic group.

FIG. 11 discloses a method of making a curcumin-resveratrol hybrid, wherein all of the hydroxyls/phenolics of the natural compounds are represented in the hybrid, providing trihydroxyl lateral phenolic groups and a dihydroxyl central phenolic group.

FIG. 12 discloses curcumin, BDMC, resveratrol and curcumin hybrids thereof, wherein all of the phenolics of the natural compounds are represented in the hybrid, providing hydroxyl demethoxy lateral phenolic groups and a hydroxy or dihydroxyl central phenolic group.

FIG. 13 provides a method of making the compound of FIG. 12 that has hydroxyl demethoxy lateral phenolic groups and a hydroxy central phenolic group.

FIG. 14 provides a method of making the compound of FIG. 12 that has hydroxyl demethoxy lateral phenolic groups and a dihydroxy central phenolic group.

FIG. 15 discloses curcumin, piceatannol and a hybrid thereof, wherein most of the hydroxyls of the natural compounds are represented in the hybrid, providing dihydroxyls in the end phenolic groups and a single hydroxyl in the central phenolic group in the positions common with the two natural compounds.

FIG. 16 provides a method of making the compound of FIG. 15.

DETAILED DESCRIPTION OF THE INVENTION

Figure 1A:
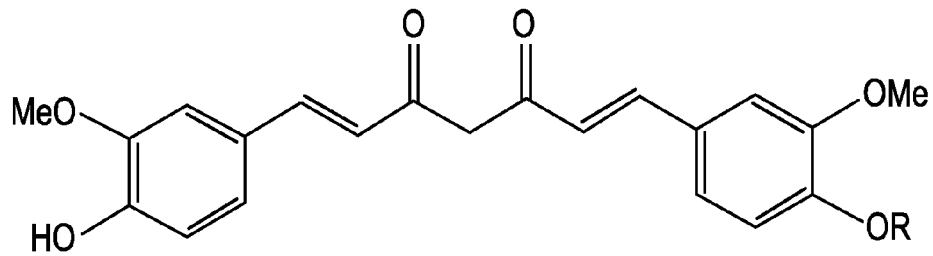
FIGS. 1a through 1c disclose novel curcumin prodrugs of the present invention (1)-(30).
Figure 1A:
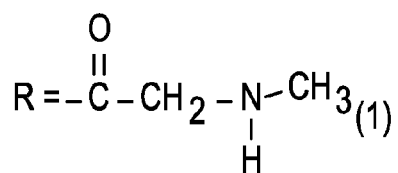
Figure 1A:
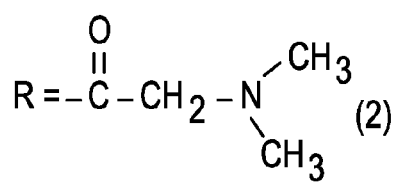
Figure 1A:
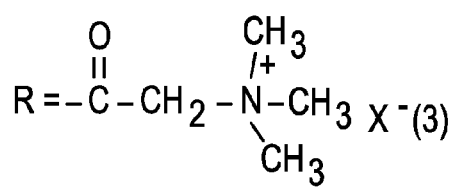
Figure 1A:
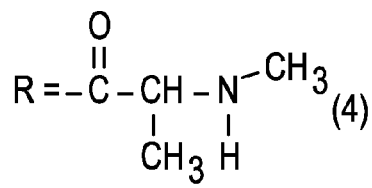
Figure 1A:
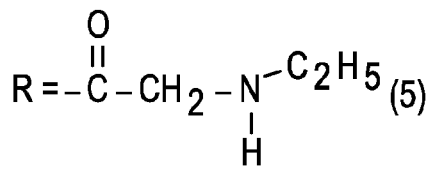
Figure 1A:
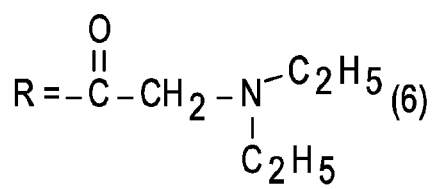
Figure 1A:
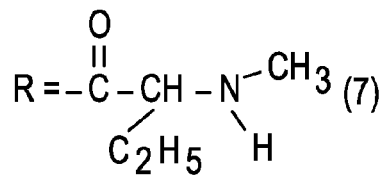
Figure 1A:
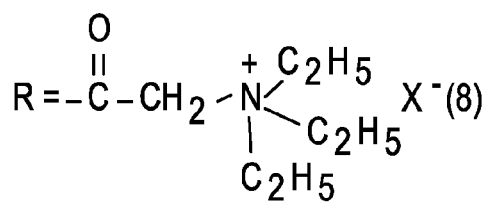
Figure 1A:
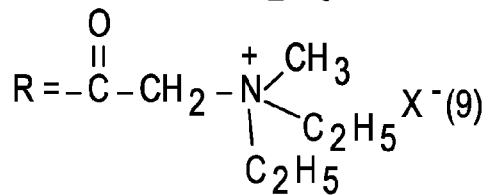
Figure 1A:
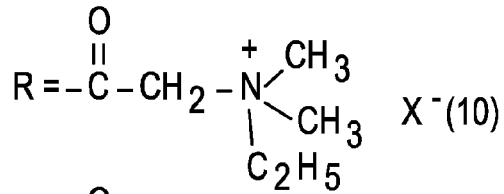
Figure 1A:
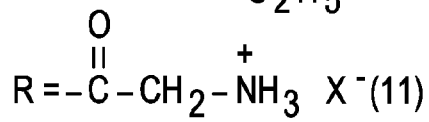
Figure 1A:
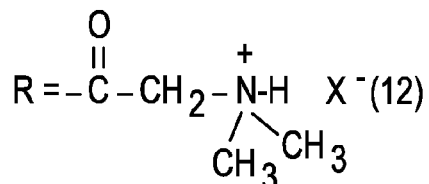
Figure 1A:
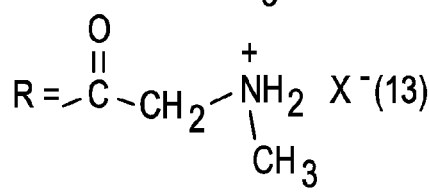
Figure 1A:
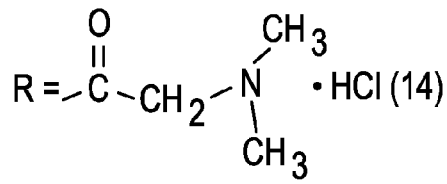

As used herein curcumin is also known as diferuloylmethane or (E,E)-1,7-bis (4-hydroxy-3-methoxyphenyl)-1, 6-heptadiene-3,5,-dione. Curcumin may be derived from a natural source, the perennial herb *Curcuma longa* L., which is a member of the Zingiberaceae family. The spice turmeric is extracted from the rhizomes of *Curcuma longa* L. and has long been associated with traditional-medicine treatments used in Hindu and Chinese medicine. Turmeric was administered orally or topically in these traditional treatment methods.

In some embodiments, curcumin is intranasally administered so that it produces a brain tissue concentration of at least 0.1 μM, more preferably at least 1 μM, more preferably at least 5 μM, more preferably at least 20 μM.

Without wishing to be tied to a theory, it is believed that a daily intranasal dose of at least about 0.2 mg/kg would be sufficient to produce the above-cited brain tissue concentrations. More preferably, the dose is at least 1 mg/kg, more preferably at least 10 mg/kg.

It is believed that applying a pharmaceutical composition comprising curcumin at the above cited levels to an upper third of a nasal cavity of the mammal, wherein the curcumin is absorbed through an olfactory mucosa and transported to the brain of the mammal, will result in attainment of these higher levels of curcumin in brain tissue.

It is known that the more lipophlilic a molecule, the greater its propensity to cross the olfactory mucosa and the blood brain barrier. In this respect, it has been reported that the octanol:water partition coefficient of curcumin ($\log_{10}$ PC) is 3.29. Therefore, curcumin is very lipophilic, and so should easily cross the olfactory mucosa and the blood brain barrier by passive diffusion.

It is further known that the blood brain barrier contains the p-glycoprotein (P-gp) transporter which effluxes a number of important molecules such as drugs. Accordingly, the behaviour of these pumps towards curcumin is pertinent to the question of whether curcumin will cross the olfactory mucosa and the blood brain barrier. Since it has been reported that curcumin lowers the expression of P-gp (Holland, *Biochem. Pharmacol.* 2006, Apr. 14, 71(8) 1146-54), it is believed that curcumin antagonizes these P-gp pumps. In addition to its ability to lower the expression of P-gp, it has been suggested that curcumin is able to modulate the function of hepatic P-gp. In both freshly-plated hepatocytes, containing low levels of Pgp, and 72 hour-cultured hepatocytes, containing high levels of Pgp, the Rhodamine-123 (R-123) efflux, which represents a specific functional test for Pgp-mediated transport, was inhibited by curcumin in a dose-dependent manner. (Romiti N, Tongiani R, Cervelli F, Chieli E. Effects of curcumin on P-glycoprotein in primary cultures of rat hepatocytes. *Life Sci.* 1998; 62: 2349-58.).

Because the octanol:water partition coefficient of curcumin ($\log_{10}$ PC) is 3.29 and curcumin has been shown to antagonize P-gp, it is believed that curcumin will easily cross the blood brain barrier. In this respect, it is helpful to compare these qualities of curcumin to those of hydroxyzine. It has been reported by Kandimalla, *Int'l. J. Pharmaceutics*, 302 (2005) 133-144, that hydroxyzine HCl has a molecular weight of 447.8, an octanol:water partition coefficient of log Doct/pH 7.4 of only 2.37-2.87, and has the ability to inhibit P-gp. According to Kandimalla, "the lipophilicity of (hydroxyzine), coupled with (its) ability to inhibit P-gp, enable(s) (it) to freely permeate across the olfactory mucosa." Because curcumin has an even lower molecular weight than hydroxyzine, has a significantly higher lipophilicity, and is able to lower both the function and expression of p-gp, it is reasonably concluded that curcumin should be able to pass through the olfactory mucosa and the blood brain barrier even easier than hydroxyzine.

Since curcumin (MW=368) and carbamazepine (MW=236) have similar molecular weights and are each highly lipophilic, the effects of intranasal carbamazepine upon carbamazepine brain concentration are highly instructive. Barakat, *J. Pharm. Pharmacol.*, 2006, January 58(1) 63-72 reports that peak brain tissue concentrations of carbamazepine attained by intranasal dosing (12 ug/g) were about four times higher than those attained by oral dosing:

| Route | Carbamazepine Dose (mg/kg) | Carbamazepine Peak Brain Tissue (ug/g) | ~uM |
|---|---|---|---|
| Intranasal | 0.2 | 12 | 48 |
| Intravenous | 8.0 | 4 | 16 |
| Oral | 16 | 3 | 12 |

Therefore, if curcumin enters the brain in molar amounts similar to carbamazepine (as is reasonably expected), then the resulting concentrations may be sufficient to both completely prevent toxic oligomer formation and effect Aβ metal binding. If even higher dosages of curcumin are used above 0.2 mg/kg, then the resultant brain tissue concentration would be expected to be even higher.

The dose of curcumin can be combined with a mucoadhesive to enhance its contact with the olfactory mucosa. In some embodiments, the mucoadhesive is selected from the group consisting of a hydrophilic polymer, a hydrogel and a thermoplastic polymer. Preferred hydrophilic polymers include cellulose-based polymers (such as methylcellulose, hydroxyethyl cellulose, hydroxy propyl methyl cellulose, sodium carboxy methyl cellulose), a carbomer chitosan and plant gum.

In some embodiments, the mucoadhesive is a water-soluble high molecular weight cellulose polymer. High molecular weight cellulose polymer refers to a cellulose polymer having an average molecular weight of at least about 25,000, preferably at least about 65,000, and more preferably at least about 85,000. The exact molecular weight cellulose polymer used will generally depend upon the desired release profile. For example, polymers having an average molecular weight of about 25,000 are useful in a controlled-release composition having a time release period of up to about 8 hours, while polymers having an average molecular weight of about 85,000 are useful in a controlled-release composition having a time released period of up to about 18 hours. Even higher molecular weight cellulose polymers are contemplated for use in compositions having longer release periods. For example, polymers having an average molecular weight of 180,000 or higher are useful in a controlled-release composition having a time release period of 20 hours or longer.

The controlled-release carrier layer preferably consists of a water-soluble cellulose polymer, preferably a high molecular weight cellulose polymer, selected from the group consisting of hydroxypropyl methyl cellulose (HPMC), hydroxyethyl cellulose (HEC), hydroxypropyl cellulose (HPC), carboxy methyl cellulose (CMC), and mixtures thereof. Of these, the most preferred water-soluble cellulose polymer is HPMC. Preferably the HPMC is a high molecular weight HPMC, with the specific molecular weight selected to provide the desired release profile.

The HPMC is preferably a high molecular weight HPMC, having an average molecular weight of at least about 25,000, more preferably at least about 65,000 and most preferably at least about 85,000. The HPMC preferably consists of fine particulates having a particle size such that not less than 80% of the HPMC particles pass through an 80 mesh screen. The HPMC can be included in an amount of from about 4 to about 24 wt %, preferably from about 6 to about 16 wt % and more preferably from about 8 to about 12 wt %, based upon total weight of the composition.

Hydrogels can also be used to deliver the curcumin to the olfactory mucosa. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the curcumin at the application site, thereby eliminating undesired migration from the site. The hydrogels are also biocompatible, e.g., not toxic, to cells suspended in the hydrogel. A "hydrogel-inducer composition" is a suspension of a hydrogel containing desired curcumin. The hydrogel-inducer composition forms a uniform distribution of inducer with a well-defined and precisely controllable density. Moreover, the hydrogel can support very large densities of inducers. In addition, the hydrogel allows diffusion of nutrients and waste products to, and away from, the inducer, which promotes tissue growth.

Hydrogels suitable for use in the present invention include water-containing gels, i.e., polymers characterized by hydrophilicity and insolubility in water. See, for instance, "Hydrogels", pages 458-459 in Concise Encyclopedia of Polymer Science and Engineering, Eds. Mark et al., Wiley and Sons, 1990, the disclosure of which is incorporated herein by reference.

In a preferred embodiment, the hydrogel is a fine, powdery synthetic hydrogel. Suitable hydrogels exhibit an optimal combination of such properties as compatibility with the matrix polymer of choice, and biocompatability. The hydrogel can include any of the following: polysaccharides, proteins, polyphosphazenes, poly(oxyethylene)-poly(oxypropylene) block polymers, poly(oxyethylene)-poly(oxypropylene) block polymers of ethylene diamine, poly (acrylic acids), poly(methacrylic acids), copolymers of acrylic acid and methacrylic acid, poly(vinyl acetate), and sulfonated polymers. Other preferred hydrogels include poly (acrylic acid co acrylamide) copolymer, carrageenan, sodium alginate, guar gum and modified guar gum.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Preferred thermoplastic polymers include PVA, polyamide, polycarbonate, polyalkylene glycol, polyvinyl ether, polyvinyl ether, and polyvinyl halides, polymethacrylic acid, polymethylmethacrylic acid, methyl cellulose, hydroxypropyl cellulose, hydroxypropyl methylcellulose, and sodium carboxymethylcellulose, ethylene glycol copolymers.

Other polymers that may be suitable for use as a mucoadhesive include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\chi$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, $\chi,\chi$-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the Handbook of Biodegradable Polymers, edited by Domb, et. al., Hardwood Academic Press, pp. 251-272 (1997). Copoly (ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer-based polymers made from L-lactide, D,L-lactide, lactic acid, glycolide, glycolic acid, para-dioxanone, trimethylene carbonate and $\epsilon$-caprolactone such as are described by Allcock in The Encyclopedia of Polymer Science, Vol. 13, pages 31-41, Wiley Intersciences, John Wiley & Sons, 1988 and by Vandorpe, et al in the Handbook of Biodegradable Polymers, edited by Domb, et al, Hardwood Academic Press, pp. 161-182 (1997). Polyanhydrides include those derived from diacids of the form HOOC—$C_6H_4$—O—

(CH$_2$)$_m$—O—C$_6$H$_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

In some embodiments, the mucoadhseive is selected from the group consisting of poly(lactic acid) ("PLA") and poly (glycolic acid)("PGA"), and copolymers thereof.

In some embodiments, the mucoadhesive formulation includes a penetration enhancer such as sodium glycocholate, sodium taurocholate, L-lysophosphotidyl choline, DMSO and a protease inhibitor.

In some embodiments, the curcumin is tagged with a molecule that binds specifically with the olfactory mucosa, such as an odorant.

In some embodiments, the pharmaceutical composition comprising curcumin includes a pharmaceutically-acceptable carrier, a lipophilic micelle, a liposome, or a combination thereof. Preferably, the lipophilic micelle or liposome comprises a ganglioside, a phosphatidylcholine, a phosphatidylserine, or a combination thereof.

In some embodiments, the pharmaceutical composition comprises a substance having an affinity for a receptor site on a neuron.

According to particular methods of intranasal delivery, it can be desirable to prolong the residence time of the pharmaceutical composition in the nasal cavity (e.g., in the olfactory region and/or in the sinus region), for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl), which are agents that enhance residence time in the nasal cavity. As a further approach, increasing the viscosity of the dosage formulation can also provide a means of prolonging contact of agent with olfactory epithelium. The pharmaceutical composition can be formulated as a nasal emulsion, ointment or gel, which offer advantages for local application because of their viscosity.

The pharmaceutical composition can also optionally include an absorption enhancer, such as an agent that inhibits enzyme activity, reduces mucous viscosity or elasticity, decreases mucociliary clearance effects, opens tight junctions, and/or solubilizes the active compound. Chemical enhancers are known in the art and include chelating agents (e.g., EDTA), fatty acids, bile acid salts, surfactants, and/or preservatives. Enhancers for penetration can be particularly useful when formulating compounds that exhibit poor membrane permeability, lack of lipophilicity, and/or are degraded by aminopeptidases. The concentration of the absorption enhancer in the pharmaceutical composition will vary depending upon the agent selected and the formulation.

To extend shelf life, preservatives can optionally be added to the pharmaceutical composition. Suitable preservatives include but are not limited to benzyl alcohol, parabens, thimerosal, chlorobutanol and benzalkonium chloride, and combinations of the foregoing. The concentration of the preservative will vary depending upon the preservative used, the compound being formulated, the formulation, and the like. In some representative embodiments, the preservative is present in an amount of 2% by weight or less.

The pharmaceutical composition can optionally contain an odorant, e.g., as described in EP 0 504 263 B1 to provide a sensation of odor, to aid in inhalation of the composition so as to promote delivery to the olfactory epithelium and/or to trigger transport by the olfactory neurons.

In some embodiments, the curcumin is delivered in a pharmaceutical composition selected from the group consisting of a liquid, a powder, a spray, a nose drop, a gel, an ointment, or a combination thereof.

In some embodiments, the curcumin is delivered in a pharmaceutical composition comprising piperine.

In some embodiments, the method of the present invention includes applying the pharmaceutical composition to an olfactory area in the upper third of the nasal cavity, such as the olfactory mucosa. In some embodiments, the method of the present invention includes applying the pharmaceutical composition to a roof of a nasal cavity. In some embodiments, the method of the present invention includes applying the pharmaceutical composition by employing a tube, a catheter, a syringe, a packtail, a pledget, a submucosal infusion, an intranasal spray container, or a combination thereof.

For delivery, there is provided a standard nose drops squeezable spray container with a long thin semi-flexible tube attached to the distal end. The outer diameter of the tube is less than a millimeter, preferably less than 0.5 mm, more preferably less than 0.25 mm. The exit hole of the tube is preferably located on the peripheral wall near the distal end of the tube so that spray exiting it can be directed upwards. There is a marker on the container that indicates when the exit hole is oriented upwards towards the cribriform plate.

Therefore, in accordance with the present invention, there is provided an intranasal spray device comprising:
  a) a hollow container having a first opening,
  b) a flexible tube having a throughbore, a distal end portion having a second opening, a proximal end having a third opening,
  c) a formulation comprising an effective amount of curcumin contained within the container,
wherein the third opening of the proximal end of the tube is in fluid connection with the first opening of the hollow container In other embodiments, the intranasal spray device comprises:
  a) a hollow container having a first opening,
  b) a flexible tube having a throughbore, a side surface having a second opening, a proximal end having a third opening, and a distal end having an end surface,
  c) a formulation comprising an effective amount of curcumin contained within the container,
wherein the third opening of the proximal end of the tube is in fluid connection with the first opening of the hollow container.

The user directs the tube towards the medial wall of the nostril and points upwards so as to direct it medially to and over the middle nasal concha. The length of the tube is predetermined so that when the user has the shoulder of the container flush against the nostril, the hole is adjacent the cribriform plate.

If there is concern about the safety of inserting a tube through a nasal passage, then the tube can also be balloon-like, so that it expands to full length upon being pressurized.

Delivery Through Anterior Nares

It has been reported that less than about 10% of inspired air travels through the olfactory slit. Accordingly, a great deal of the curcumin delivered to the nasal cavity does not region the olfactory mucosa. Therefore, it is an object of the present invention to increase the amount of curcumin delivered to the olfactory mucosa.

It has been reported in the literature that when the airflow in the nasal cavity can be characterized as laminar, streamlines from the anterior 10% of the nares reach the olfactory slit.

Accordingly, in some embodiments of the present invention, at least 25% of the formulation comprising curcumin is delivered into the anterior 10% of the nares. Preferably, at least 50% of the formulation comprising curcumin is delivered into the anterior 10% of the nares. More preferably, at least 75% of the formulation comprising curcumin is delivered into the anterior 10% of the nares.

In some embodiments, focused delivery of the formulation into the anterior portion of the nares is assisted by providing a guidance tube located substantially in the anterior 10% of the nares.

In some embodiments, there is provided a device for assisting delivery of a formulation to the anterior portion of the nares, comprising:
 a) an annulus adapted to fit in the opening of the nares and
 b) a guidance tube extending from the annulus and connected to the annulus in the region of the anterior 10% of the nares.

As the streamlines just inside the opening of the nares travel at an angle of about 90 degrees, the guidance tube is preferably situated at that angle in order to deliver the formulation into those streamlines. Preferably, the annulus is oval-shaped to correspond to the shape of the nares.

In use, the user simultaneously slowly inhales while actuating the spray container containing the formulation. The formulation is delivered to the anterior portion of the guidance tube as an aerosol in a laminar flow. The formulation travels through the guidance tube and exits is posterior end as an aerosol in a laminar flow. Thus, the formulation should enter the nasal cavity in conformance with the laminar streamlines of the inspired air produced by the inhalation. Once in these streamlines, the formulation travels preferentially to the olfactory slit and thus to the olfactory mucosa.

Helium

In some embodiments, the curcumin is delivered to the olfactory mucosa through helium-laden microbubbles that can rise in the air. This takes advantage of the fact that the olfactory mucosa is located in the highest portion of the nasal cavity. Theoretically, helium-filled microbubble of proper dimensions that are conventionally delivered into the nasal cavity should travel upwards to the highest spot in the nasal cavity—the olfactory mucosa. Once they are in place, the microbubbles can be exploded with a simple hand held, non-invasive ultrasound device, thereby releasing their contents. This invention would greatly increase the amount of curcumin that ends up in the olfactory mucosa.

Therefore, in accordance with the present invention, there is provided a method for transporting a neurotherapeutic drug to a brain of a mammal, comprising:
 a) applying a plurality of microbubbles comprising the neurotherapeutic drug (preferably, curcumin), wherein the microbubbles are lighter than air (and preferably contain helium gas), to a nasal cavity of the mammal, whereby the microbubbles rise to an upper third of a nasal cavity of the mammal, whereupon the neurotherapeutic drug is absorbed through an olfactory mucosa and transported to the brain of the mammal.

In other embodiments, the curcumin is delivered to the olfactory mucosa as an aerosol in a bolus of helium gas that can rise in the air. This also takes advantage of the fact that the olfactory mucosa is located in the highest portion of the nasal cavity. Theoretically, a helium bolus and the aerosols therein that are conventionally delivered into the nasal cavity should travel en masse to the highest spot in the nasal cavity—the olfactory mucosa. Once they are in place, the aerosols can deposit upon the nasal walls containing the olfactory mucosa. This invention would greatly increase the amount of curcumin that ends up in the olfactory mucosa.

Therefore, in accordance with the present invention, there is provided a method for transporting a neurotherapeutic drug to a brain of a mammal, comprising:
 a) providing a formulation comprising aerosol droplets of a neurotherapeutic drug (preferably, curcumin) in a bolus of helium gas, and
 b) applying the formulation to a nasal cavity of the mammal, whereby the formulation rises to an upper third of a nasal cavity of the mammal, whereupon the neurotherapeutic drug is absorbed through a nasal mucosa and transported to the brain of the mammal.

U.S. Patent Publication No. 2003/0199594 ("Shah") discloses a propellant composition for use with an aerosol wherein the composition comprises between 70% and 100% helium, wherein the composition may be used in intranasal spray devices such as metered dose inhalers. Shah discloses that the composition may further include a solvent (such as an alcohol such as ethanol) and a dispersing agent (such as oleic acid).

Therefore, in accordance with the present invention, there is provided an intranasal spray device having a formulation comprising:
 a) an effective amount of curcumin, and
 b) a propellant comprising helium (preferably, at least about 70% helium by weight), and
 c) (optionally) a solvent (such as water or an alcohol such as ethanol), and
 d) (optionally) a dispersing agent (such as oleic acid)

Curcumin Prodrugs

Although high lipophilicity in a therapeutic compound enables it to easily cross the blood brain barrier and penetrate brain tissue, that high lipophilicity also usually means that the compound is not very soluble in water. For example, US 2003/0153512 reports that lipophilic curcumin has a solubility in water of only about 0.004 mg/ml. Because intranasal formulations are generally provided in small doses of between 50 µl and 200 µl (typically, 100 µl), there may be an issue in providing a sufficient amount of the lipophilic compound in a single dose in order to generate a therapeutic response.

Therefore, one aspect of the present invention involves providing the therapeutic compound in the form of a water-soluble prodrug. The high water solubility of the prodrug allows large amounts of it to be provided in a single dose, enter the nasal mucosa and passively diffuse across the nasal mucosa. Once the prodrug has reached the boundary of brain tissue, the prodrug is metabolized (typically through a chemical or enzymatic hydrolysis reaction with brain esterases) to the parent lipophilic molecule, whereby it can diffuse into the brain tissue bulk and provide a therapeutic benefit.

Therefore, in accordance with the present invention, there is provided a method for administering curcumin to a brain of a mammal, comprising:
a) applying a pharmaceutical composition comprising a water soluble curcumin prodrug to an upper third of a nasal cavity of the mammal, wherein the curcumin prodrug is absorbed through a nasal mucosa and transported to the brain of the mammal.

In some embodiments, the parent lipophilic compound is a phenol that is rendered water-soluble by creating an ester having an added polar moiety or a permanent charge. Preferably, the ester has a polar moiety. Preferably, the polar moiety contains a tertiary or quaternary nitrogen.

Therefore, in some embodiments, the ester contains an aminoalkanecarboxylic acid as the polar moiety. These compounds are characterized by an ester moiety having an alkane group between the nitrogen compound and the carboxyl group. Preferably, the moiety has terminal alkyl groups. More preferably, the aminoalkanecarboxylic acid contains a glycinate moiety, more preferably a methylated glycinate moiety, such as N, N, dimethylglycinate. Therefore, in accordance with the present invention, there is provided a curcumin ester prodrug comprising an aminoalkylcarboxylic acid moeity. Preferably, the aminoalkylcarboxylic acid moiety comprises an aminoalkanecarboxylic acid moiety. In some embodiments, the aminoalkanecarboxylic acid contains a glycinate moiety. Methods of making such compounds are found in Pop, *Pharm. Res., Vol.* 13(1) 1996, 62-69.

Figure 1B:
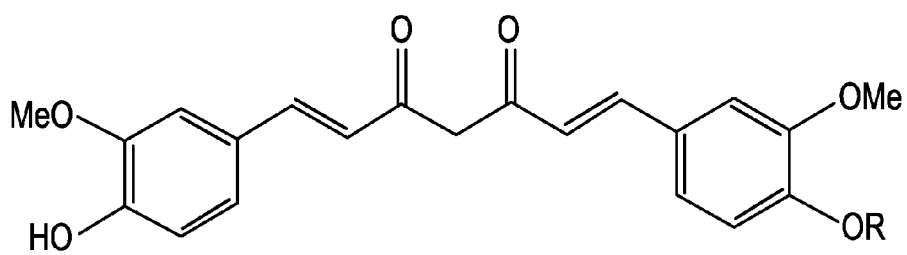
Figure 1B:
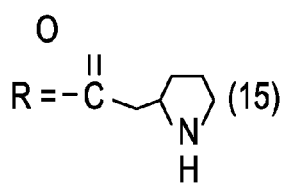
Figure 1B:
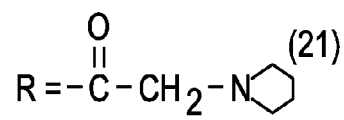
Figure 1B:
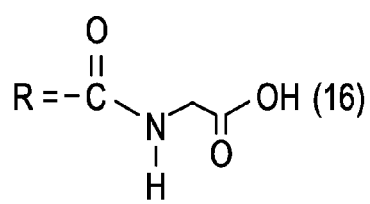
Figure 1B:
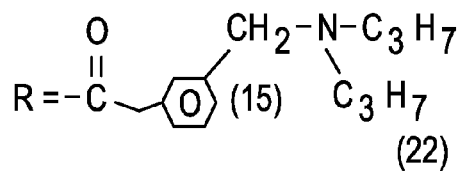
Figure 1B:
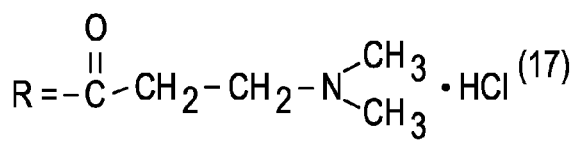
Figure 1B:
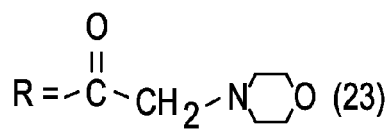
Figure 1B:
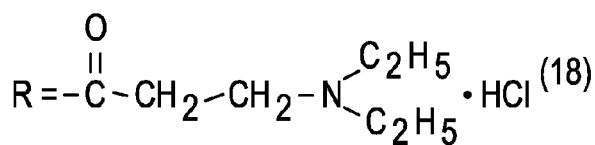
Figure 1B:
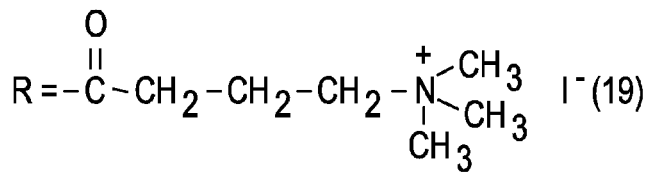
Figure 1B:
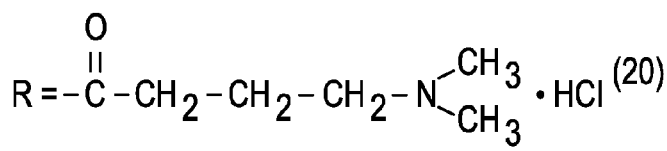
Figure 1C:
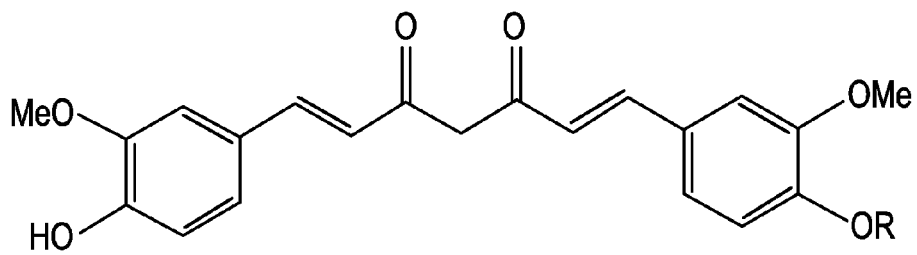
Figure 1C:
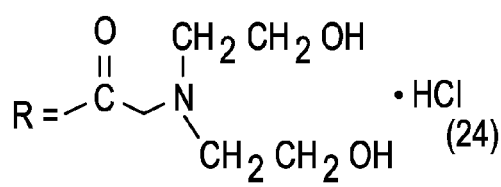
Figure 1C:
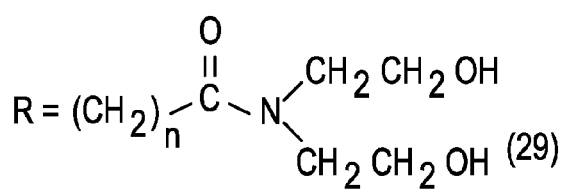
Figure 1C:
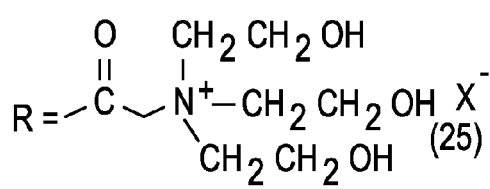
Figure 1C:
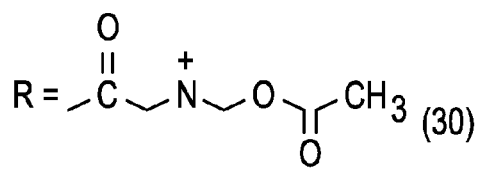
Figure 1C:
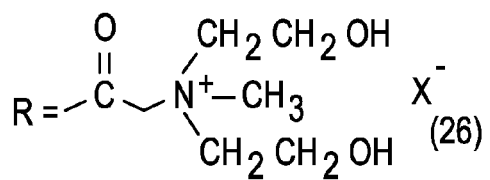
Figure 1C:
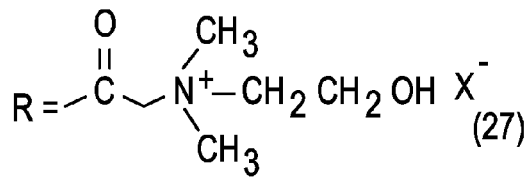
Figure 1C:
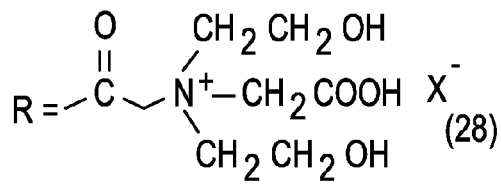

Now referring to FIGS. 1a-1c, there are provided novel curcumin prodrugs of the present invention, labeled (1) to (30).

Therefore, in some embodiments, the aminoalkanecarboxylic acid moiety comprises a single terminal methyl group (1), two terminal methyl groups (2), (17),(20), or three terminal methyl groups (3)(19).

In some embodiments, the aminoalkanecarboxylic acid moiety comprises a single terminal ethyl group (5), two terminal ethyl groups (6)(18), or three terminal ethyl groups (8).

In some embodiments, the aminoalkanecarboxylic acid moiety comprises a terminal ethyl group and a terminal methyl group; a terminal ethyl group and two terminal methyl groups (10); or two terminal ethyl groups and a terminal methyl group (9).

In some embodiments, the aminoalkanecarboxylic acid moiety comprises a terminal propyl group.

In some embodiments, the prodrug is in the form of a salt, as in compounds (3), (8)-(14), (17)-(20). Preferably, the salt comprises an anion selected from the group consisting of chloride (14)(17)(18)(20), iodide (19) and bromide.

In some embodiments, the prodrug is characterized by an ester moiety in which an ethane (17-18) or propane (19-20) group lies between the carboxyl group and the nitrogen group, and preferably has a terminal alkyl group.

In some embodiments, the prodrug is characterized by an ester moiety in which the alkane that lies between the carboxyl group and the nitrogen group is substituted. In some embodiments, this is a terminal ethyl group (7) lying between the carboxyl group and the nitrogen group. Preferably, the moiety has a second terminal alkyl group.

In some embodiments, the curcumin prodrug comprises a carbamoyl moiety, preferably a (carboxymethyl)carbamoyl moiety (16). The (carboxymethyl)carbamoyl moiety of (16) can be made in substantial accordance with Mulholland, *Annals Oncology,* 12, 245-8(2001).

In some embodiments, the aminoalkanecarboxylic acid moiety comprises a nitrogen heterocycle (21,23). In some embodiments, the heterocycle contain oxygen (23). Moeity (23) may be may in accordance with the procedure disclosed in Pop, *Pharm. Res.,* 13, 3, 469-475 (1996) and Trapani, *Intl. J. Pharm.,* 175(1998) 195-204. Moeity (21) may be may in accordance with the procedure disclosed in Trapani, *Intl. J. Pharm.,* 175(1998) 195-204. Pop, *Pharm. Res.,* 13,3, 469-475 (1996) discloses that dexanabinol having a nitrogen heterocycle moiety like (21,23) has a solubility of about 5-7 mg/ml.

In some embodiments, the aminoalkanecarboxylic acid moiety comprises a L-proline group(15). Moeity (15) may be may in accordance with the procedure disclosed in Altomare, *Eur. J. Pharm. Sci.,* 20, 2003, 17-26 and Trapani, *Intl. J. Pharm.,* 175(1998) 195-204. Altomare reports that the L-proline ester of propofol provides the prodrug with a solubility of about 1.1 mmol/ml.

In some embodiments, the aminoalkanecarboxylic acid moiety comprises a benzoate group(22). Moeity (22) may be made in accordance with the procedure disclosed in Bundgaard, *Pharm. Res.,* 8, 9, 1087-1093, (1991). Bungaard discloses that providing a benzoate moeity (22) between the carboxyl and amino groups of a glycinate moiety raises the solubility of Acyclovir from 1.4 mg/ml to 3 mg/ml at a pH of about 7, and to about 300 mg/ml at a pH of about 5.

Other curcumin glycine esters are disclosed in Mishra, *Bioorganic & Medicinal Chemistry,* 13 (2005) 1477-86; Kumar, Nucleic Acids Symposium Series No. 44, 2000, pp. 75-76; Kapoor, *Cancer Lett.,* 2007, Apr. 18, 248(2) 245-50; Tong, Anti-Cancer Drugs 17(3) 279-187 March 2006; and Mishra, Free Rad. Biology & Medicine, 38, (2005) 1353-1360

Desirable Prodrug Qualities

The curcumin prodrugs of the present invention should have three qualities: high solubility in water, high stability in water and rapid conversion to curcumin in the brain.

Solubility

The literature has demonstrated that glycinate-containing moieties provide much greater water solubility to phenolic compounds, typically increasing the solubility of the parent compound to the 25-50 mg/ml range. Examples of the solubility increase provided to low solubility phenolics by their esterification by glycinates are as follows:

TABLE I

| Parent Phenol | Parent Solubility (mg/ml) | Ester solubility (mg/ml) | Reference |
|---|---|---|---|
| dexanabinol | 2-7 | ~50 | (a) |
| d-χ-tocopherol | — | ~25 | (b) |
| 17β-estradiol | 0.008 | 0.8-20 | (c) |
| testosterone | 0.01 | >100 | (d) |
| menahydroquinone | — | ~25 | (e) |
| phenol (+L-dopa) | — | 5 | (f) |

(a) Pop, J. Pharm Sci, 88, 11, 1999, 1156
(b) Takata, J. Lipid Res., 2002, 43, 2196
(c) Al-Ghananeem, AAPS PharmSciTech, 2002, 3, 1, article 5
(d) Hussain, J. Pharm Sci., 91: 785-789, 2002.
(e) Takata, Pharm. Res., 21, 1, 1995, 18-23 (solubility reported as 50 mM)
(f) Kao, Pharm. Res., 17, 8, 2000, 978-984

It further appears that pH has a great influence upon the solubility of nitrogen-containing esters of phenols. The influence of pH upon the solubility of nitrogen-containing esters of phenols as reported in the literature is presented below:

TABLE II

| Parent | ester solubility at neutral pH (mg/ml) | ester solubility at acidic pH (mg/ml) | Reference |
|---|---|---|---|
| Propofol | 0.064 | 4.67 | (a) |
| | 0.735 | 6.920 | (a) |
| | 0.213 | 0.35 | (a) |
| Acyclovir | 3 | 300 | (b) |

(a) Trapani, Intl. J. Pharm., 175(1998) 195-204.
(b) Bundgaard, Pharm. Res., 8, 9, 1087-1093, (1991).

The literature shows that, in most cases, providing the ester in an acidic pH (about 4-5) increases its solubility in water by about 10 fold.

There also appears to be a special class of glycinate-like moieties that increase the water solubility of the phenolic compound even further. In particular, there are a number of glycinate-like moieties possessing additional oxygens that increase the water solubility of the phenolic compound to concentrations in the 100-1000 mg/ml range. Examples of such compounds are provided below:

Examination of these compounds reveals that each is characterized by terminal substitution of the amine by oxygen-containing moeities. They are particularly characterized by:
 a) a (carboxymethyl)carbamoyl moiety (Mullholland, Ann. Oncology, 12, 245-248 (2001)),
 b) an N-acyloxymethyl moiety (Neilsen, Eur. J. Pharm. Sci., 2005, Apr. 24, 5, 433-40), or
 c) a (oxyalkyl)acetamide moiety (U.S. Pat. No. 5,073,641),
 d) glycine benzoates (WO90/08128)

Without wishing to be tied to a theory, it is believed that that these moieties may act as surfactants which, in the appropriate concentration, produce micelles. Indeed, it has been reported that a (dihydroxyethyl)glycinate moiety acts as a surfactant (U.S. Pat. No. 6,831,108), and that the (carboxymethyl)carbamoyl moiety can produce micelles (Shamsi, Electrophoresis, 2005, 26, 4138-52). In one embodiment, the prodrug moiety contains both a nitrogen and an terminal oxygen and forms a zwitterion.

Therefore, in accordance with the present invention, there is provided a formulation comprising a micellar curcumin prodrug.

The (carboxymethyl)carbamoyl moiety (Mullholland) is of particular interest because is has a high solubility (>20 mg/ml). Its rapid hydrolysis in blood ($t_{1/2}$=0.39 hr) may indicate that it is also rapidly hydrolyzed by brain esterases as well. Lastly, it appears to be relatively stable in water ($t_{1/2}$=16.9 hr) and so likely is very stable in acidic aqueous solutions.

It has been reported that converting the prodrug into a salt likewise increases its solubility in water. For example, WO90/08128, which relates to glycine-like ester prodrugs, reports that conversion of such prodrugs into salts produce water solubilities of up to 15 w/v %. Jensen, Acta Pharm. Nord., 3,(1) 31-40 (1991) reports that a dichloride salt of one aminoalkylbenzoate ester was found to have a water solubility of greater than 40% v/v at 20° C. Lastly, U.S. Pat. No. 4,482,722 reports an addition salt of metrazole glycinate to have a water solubility of about 30%.

Stability

Because the formulations of the present invention are desirably used in the form of aqueous-based nasal sprays, the ester prodrugs of the present invention should remain stable in water for an appreciable time. It appears that glycinate esters are much more stable in acidic aqueous solutions than in neutral aqueous solutions. Al-Ghananeem, AAPS PharmSciTech, 2002, 3,1, article 5, reports that the stability of phenol esters is influenced by pH, that at slightly acidic pHs (pH 3-5), one phenol ester (17-DMABE$_2$HCl) would have sufficient shelf life to be formulated in a solution dosage form, and that a pharmaceutical nasal spray solution of the prodrug at pH 4 would have a shelf life of approximately 19 months at 25° C. Similarly, Kao, Pharm. Res., 17, 8, 2000, 978-984 reports a maximum stability for the L-dopa butyl ester at a pH of 4.4, that the estimated time for 10% decomposition at pH 4.4, (0.05M phosphate buffer) and 10° C. is calculated to be 2.7 years, and that at slightly acidic pHs (pH 3-5), the ester would have sufficient shelf-life stability to be formulated in a solution dosage form. Lastly, PCT Published Patent Application WO90/08128, which relates to benzoate-containing glycine-like ester prodrugs, reports that one hydrocortisone-based prodrug possessed a shelf-life in aqueous solutions of pH 4.0 of 6.0 and 10.2 years at 25° C. and 20° C., respectively.

Therefore, in some embodiments of the present invention, the curcumin formulation contains a buffer setting a pH of between about 3.0 and 5.5, preferably a pH of between about 3.5 and 5, preferably a pH of between about 4 and 5. In some embodiments of the present invention, the curcumin formulation contains a buffer setting a pH of between about 3 and 4. It is believed that setting the pH of the formulation in these ranges would allow the formulations to have a commercially satisfactory shelf life.

Also in some embodiments of the present invention, there is provided an intranasal spray device comprising a formulation comprising:
 a) an effective amount of curcumin, and
 b) a buffering agent setting a pH of between 3 and 5.5.

Conversion Rate

Once the prodrug has reached the brain, it is desirable for the esterified prodrug to be converted to its parent compound in a very rapid fashion. Simply, the prodrug should be converted to the parent compound by brain esterases before it is drained from the brain. In order to understand whether a prodrug converts sufficiently rapidly to the parent compound, it is important to know the residence time of the prodrug in the brain or CSF.

Review of concentration versus time profiles of intranasally instilled compounds reveals behaviors characterized by a two phase model. In the first phase, the drug rapidly attains a peak concentration and then rapidly decreases to about 10-25% of the peak concentration within about 1-2 hours. The second phase is characterized by a very slow decrease in the concentration of the drug over the next 24 hours.

Therefore, if the concentration of the drug is approximated as that which is present in the 1-2 hour range (i.e., about 10-25% of the peak concentration), it can be assumed that the drug is present in the brain for about 24 hours. Accordingly, in order to be useful, the conversion rate of the prodrug to the parent compound in the brain should be characterized by a half-life $t_{1/2}$ of no more than about 12 hours.

In at least three instances, the literature has reported conversion rates of a glycinate-containing phenolic ester to the parent compound by brain homogenate. Two of these papers report very rapid conversion. Al-Ghananeem, AAPS PharmSciTech, 2002, 3, 1, article 5, reports that the rapid conversion of estradiol glycinate esters to the parent estradiol in about 1-2 minutes. Kao, Pharm. Res., 17, 8, 2000, 978-984 reports the rapid conversion of a benzyl L-dopa ester (wherein the L-dopa parent contains the glycinate moiety) in about 1 minute.

Since it is desirable to have a prodrug-to-parent conversion rate characterized by a half life $t_{1/2}$ of no more than about 12 hours, and the literature reports half-lives the rapid conversion of glycinate esters to the parent phenolic compound in about 1-2 minutes, it is clear that glycinate prodrugs should be assumed to be fully converted in the brain to the parent prodrug. It should be noted that one investigator (Trapani, Intl. J. Pharm., 175(1998) 195-204) reports a much slower conversion of propofol glycinate ester to the parent propofol. However, review of the pertinent structure-activity relationships indicates that the hydroxyl moiety of the propofol is severely sterically hindered by adjacent isopropyl groups of the propofol. Without wishing to be tied to a theory, it is believed that the severe steric hinderance of the etheric oxygen of these propofol glycinates is the reason for its slow conversion from the glycinate ester to propofol.

In contrast, the etheric oxygen of both benzyl L-dopa ester and the estradiol glycinate ester experiences much less streric hinderence, and so the brain esterase has an opportunity to freely approach the etheric oxygen from at least one side of the molecule. As a result, the hydrolysis reaction by brain esterases can occur much more quickly.

Undertaking a similar analysis with curcumin glycinate esters reveals that, like L-dopa and estradiol, the curcumin glycinate ester experiences much less streric hinderence, and so the brain esterases have the opportunity to freely approach the etheric oxygen of the curcumin glycinate ester from at least one side of the molecule.

Moreover, it appears that another research group reports a much faster conversion of the propofol dimethyl glycinate ester to the parent and that the Trapani group has acknowledged this difference. See Altomare, *Eur. J. Pharm. Sci.*, 20, 2003 17-26.

Lastly, the Kao paper is noteworthy in that it reports highly similar half-lives for the conversion of L-dopa esters to L-dopa in brain homogenate and plasma. A high coincidence of half-lives for the conversion of propofol glycinate esters to propofol in brain homogenate and plasma is also reported in Trapani. If conversion in plasma is used to reasonably estimate the conversion of glycinate esters in brain homogenate, then the literature may be further consulted for the conversion of glycinate-containing phenolic esters to the parent phenolic compound in plasma. The literature, reported below in Table III, reports the following:

TABLE III

| Parent Compound | Half-life Of glycinate ester In plasma (min) | Reference |
|---|---|---|
| Dexanabinol | 0-26 | (a) |
| Phenol (+L-dopa) | 0.36 | (b) |
| Acyclovir | 0.8 | (c) |
| Estradiol | 1-2 | (d) |
| Propofol | 24 hrs | (e) |
| Menahydroquinone | 13 | (f) |

(a) Pop, J. Pharm. Sci., 88, 11, 1999, 1156
(b) Kao, Pharm. Res., 17, 8, 2000, 978-984
(c) Bundgaard, Pharm. Res., 8, 9, (1991) 1087-1093
(d) Al-Ghananeem, AAPS PharmSciTech, 2002, 3, 1, article 5
(e) Trapani, Intl. J. Pharm., 175(1998) 195-204
(f) Takata, Pharm. Res., 21, 1, 1995, 18-23

Thus, using literature reports of conversion in plasma to reasonably estimate the likely conversion window of glycinate esters in brain homogenate, it appears that the conversion of glycinate-containing phenolic esters to the parent phenolic compound in brain is again quite rapid.

Therefore, because unhindered phenolic glycinate esters rapidly convert to the parent phenol in brain homogenate, and because dimethylglycinate phenolic esters convert rapidly in plasma, it is believed that the conversion rates of glycinate-containing curcumin esters to the parent curcumin compound will be rapid in a brain environment.

How to Make Prodrugs

Al-Ghananeem, *AAPS PharmSciTech*, 2002, 3, 1, article 5, teaches how to make an ester comprising the following amino-alkane-carboxylic acid moieties: 3-N,N dimethylamino butyl ester HCl (3-DMABE$_2$HCl); 3-N,N-diethylamino propionyl ester hydrochloride (DEAPE$_2$HCl); 3-N,N,N-trimethylamino butyl ester iodide (3-TMABE$_2$ iodide) and 17-N,N dimethylamino butyl ester HCl (17-DMABE$_2$HCl);

In some embodiments, the water-soluble ester prodrug is created by reacting the phenolic parent compound with dimethylglycine. The literature reports rendering lipophilic phenolic compounds water soluble by reacting the phenolic parent compound with dimethylglycine. For example, Al-Ghananeem, *AAPS PharmSciTech*, 2002, 3, 1, article 5, reports increasing the water solubility of 17B-estradiol from 0.008 mg/ml to 0.8 mg/ml (a 100-fold increase) by creating a dimethylglycine ester of the parent compound. Al-Ghananeem further found that this ester was readily hydrolyzed by rat brain homogenate to provide the parent compound, and that intranasal administration of the prodrug provided a 5-8 fold higher CSF concentration of 17B-estradiol when compared with a comparable intravenous dose of the prodrug. Al-Ghananeem concluded that the prodrug provides for targeted intranasal delivery of 17B-estradiol to the brain.

In some embodiments, creation of the water soluble ester prodrug from the parent phenolic compound is carried in substantial accordance with the method described in Hussain, *J. Pharm. Sci.*, 91, 3, March 2002, 785-789. In particular, dimethylglycine HCl and oxalyl chloride are gently warmed at 40° C. until evolution of HCl gas ceases. Nitrogen gas is then bubbled through the solution to remove unreacted oxalyl chloride. The resulting acid chloride is dissolved in dimethylformamide and added dropwise with stirring to a solution of the parent phenolic compound in methylene chloride. The reaction mixture is refluxed for 3 hours. The ester is then isolated, and converted to an HCl salt.

In some embodiments, creation of the water soluble ester prodrug from the parent compound is carried in substantial accordance with the method described in Al-Ghananeem, *AAPS PharmSciTech*, 2002, 3, 1, article 5. In particular, 4-(dimethylamine)butyric acid hydrochloride (2.0 g, 0.012 mol) or 3-(dimethylamine)proprionic acid hydrochloride (2.2 g, 0.012 mol) is used as a starting material. The amino acid is refluxed gently with oxalyl chloride (1.6 mL, 0.018 mol) for a short period of time until a clear yellow solution is formed. The solution mixture is then flushed very gently with a stream of nitrogen to remove excess oxalyl chloride leaving a solid behind (the acid chloride).

The phenolic esters having 3-N,N-dimethylamino butyl ester hydrochloride (3-DMABE$_2$HCl); 3-N,N-dimethylamino propionyl ester hydrochloride (3-DEAPE$_2$HCl); and 3-N,N,N-trimethylamino butyl ester iodide (3-TMABE$_2$ iodide) as moieties are synthesized after the appropriate acid chloride following the procedure reported in Hussian, *Pharm. Res.*, 1988, 5, 1, 44-47. The alcoholic ester, 17-N,N-dimethylamino butyl ester hydrochloride (17-DMABE$_2$HCl) is prepared by dissolving the acid chloride slowly in 10 mL N,N, dimethylformamide (DMF) while in an ice bath since the reaction is exothermic. The parent phenolic compound is then dissolved in methylene chloride, and the DMF solution of acid chloride was added dropwise to the solution of the parent phenolic compound with stirring; The reaction mixture is refluxed gently for 45 minutes, then filtered. The filtrate is evaporated using a Buchi model rotavaporator (Westbury, N.Y.) then redissolved in a small volume of 80 CHCl$_3$:20 MeOH. The content of the mixture is separated and purified using a silica gel column. The solvent mixture is evaporated and the product redissolved in a small volume of methylene chloride, then hydrogen chloride gas is carefully bubbles through the solution with stirring. The ester hydrochloride is precipitated by adding enough diethyl ether to make the solution turbid and then the mixture is placed in a refrigerator at 4° C. overnight. The final product is collected by solvent evaporation in a vacuum dessicator using a Precision Scientific model D75 pump (Chicago, Ill.) at room temperature and stored in a desiccator until used.

In some embodiments, creation of the water soluble ester prodrug from the parent compound is carried in substantial accordance with the method described in Takata, *J. Lipid Res.*, 2002, 43, 2196-2204. In particular, to a dry pyridine solution of the parent phenolic compound (4.8 mmol), 5.7 mol of N,N,-dimethylglycine HCl and 5.7 mmol of dicyclohexylcarbodiimide are added. The reaction mixture is stirred at room temperature for 20 hours and the dicyclohexylurea formed is removed by filtration. After the solvent is evaporated, the residue is treated with 100 ml of water and made alkaline by sodium bicarbonate. The solution is then extracted with ethyl acetate (100 ml×3). The organic layer is dried over anhydrous sodium sulfate with ethyl acetate and evaporated. The residue is fractionated with a flash column packed Wakogel LP40, 60A using n-hexane ethyl acetate (8:2, v/v) as the eluent. The isolated ester is directly collected in isopropyl ether containing 3% HCl dioxane solution, and the precipitate and recrystallized from acetone to give the HCl salt of the parent phenolic compound.

Brain Levels

Evidence that the intranasal installation of a water soluble prodrug of curcumin can deliver high levels of curcumin to the brain is found in the estradiol-based work of Al-Ghananeem, *AAPS PharmSciTech,* 2002, 3, 1, article 5. 17β-Estradiol is a 272 dalton phenol having a octanol/water partition coefficient of about log P=3.1-4.0. Therefore, estradiol is similar to curcumin in that each is a lipophilic, phenolic small molecule. Also, like curcumin, 17β-estradiol also suffers from poor bioavailability. Moreover, Al-Ghananeem reports that estradiol is not very soluble in water, thereby making impractical the nasal administration of an effective dose (0.1 mg in 0.1 ml). Al-Ghananeem reports modifying estradiol with a dimethylglycinate moiety to increase the water solubility of estradiol from 0.008 mg/ml to about 0.8 mg/ml—a 100-fold increase, and modifying estradiol with a 3-DEAPE$_2$HCl moiety to increase the water solubility of estradiol from 0.008 mg/ml to about 20 mg/ml—over a 1000 fold increase. Thus, the solubility of a lipophilic, phenolic small molecule like curcumin, which has a solubility in water of only about 0.004 mg/ml, can be greatly increased.

Because the typical volume of an intranasal dose for a human can be up to 0.2 ml, and Table I above reports increases in solubility in the range of 20 mg/ml, nasal administration can be expected to achieve a payload of up to about 20 mg/ml×0.2 ml=4 mg/dose. Because providing two doses per nostril twice a day provides 8 doses per day, it is believed that up to about 32 mg/day of estradiol can be intranasally administered. This amount provides a whole body concentration of nearly about 0.5 mg/kg.

Further, Al-Ghananeem reports that the nasal installation of 0 1 mg/kg of water soluble prodrugs of 17β-Estradiol results in peak cerebrospinal fluid (CSF) concentrations of estradiol of between about 30 ng/ml (for 17-DMABE$_2$-HCl) to about 66 ng/ml (for 3-DMABE$_2$-HCl), which provides a molar concentration of the compound of between about 0.075 μM and 0.15 μM. The pharmacokinetic results of Al-Ghananeem correspond quite well with those of Kao, who reported that nasal installation of 20 mg/kg of water soluble ester prodrug of L-dopa results in peak cerebrospinal fluid (CSF) concentration of about 10-20 ug/ml. Accordingly, a 0.5 mg/kg nasal instillation of a water soluble prodrug of a lipophilic, small molecule phenolic compound such as estradiol or curcumin can likely provide CSF concentrations of up to about 0.75 μM. Since it has been reported that 0.1-1.0 μM curcumin inhibits the in vitro formation of amyloid beta oligomers, and blocks the in vitro toxicity of Aβ$_{1-42}$ oligomers in differentiated neuroblastoma cells (Yang, *J. Biol. Chem.,* 280, 7, Feb. 18, 2005, 5892-5901), it appears that the intranasal installation of a water soluble prodrug of curcumin will likely allow an attainable dosing schedule to attain a brain concentrations of curcumin that will provide a therapeutic benefit against Alzheimer's Disease.

Dual Phase Curcumin

In some embodiments, curcumin is present within two separate phases of the formulation. The first phase is preferably a quick release phase that quickly delivers curcumin to the olfactory mucosa. The quick delivery of curcumin will have the effect of transiently disabling enzymes systems such as UGTs and P450s that metabolize curcumin. The second phase is a slow release phase that slowly delivers curcumin to the olfactory mucosa. Once these enzyme systems are transiently disabled, the slow release phase slowly releases curcumin in an environment that is substantially free of enzymatic metabolic interference.

Therefore, in accordance with the present invention, there is provide a formulation comprising:

a) a first, quick release phase comprising an effective amount of curcumin for transiently disabling enzyme systems, and b) a second slow release phase comprising an effective amount of curcumin for treating a neurodegenerative disease.

In some embodiments, the first quick release phase can be selected from the group consisting of a mucoadhesive and an oil, such as peppermint oil. Peppermint oil has the quality of independently inhibiting UGT and P450 enzymes.

In some embodiments, the second slow release phase can be selected from the group consisting of liposomes and thermoplastic polymers (such as PLGA).

In accordance with the present invention, there is provided a formulation comprising:

a) a polymeric particulate depot comprising curcumin, and b) a mucoadhesive.

In some embodiments, the mucoadhesive is present as a coating upon the polymeric particulate depot.

In some embodiments, the mucoadhesive is present as a separate particulate.

In some embodiments, the mucoadhesive comprises a compound selected from the group consisting of a chitosan and a cellulose.

In some embodiments, the mucoadhesive further contains curcumin.

In some embodiments, the polymeric particulate depot is a liposome.

In some embodiments, the polymeric particulate depot is a thermoplastic bioresorbable polymer.

In some embodiments, the curcumin is housed in microspheres. Kumar, *Indian J. Physiol. Pharmacol.,* 2002 April 46(2) 209-17 reports that when curcumin was loaded into either albumin or chitosan microspheres, a biphasic release pattern occurred, characterize by a burst effect followed by a slow release. This biphasic effect corresponds well with the stated desire to have a first dose of curcumin released in order to inhibit enzyme activity in the olfactory mucosa followed by a second dose that is slowly released, taken up by the olfactory neurons and transported to the brain. In some embodiments, the curcumin is housed in microspheres that display a biphasic release effect.

Enzyme Inhibition by Curcumin

Although curcumin is susceptible to metabolism by enzymes, curcumin is also known as an inhibitor of those very enzymes. For example, Hong, *Biochem. Biophys. Res.*

Comm., 2003 Oct. 10, 310(1) 222-7, reports that co-treatment by curcumin of EGCG in cells transfected with hPgP, hMRP1 and hMRP2 genes increased the accumulation of EGCG in those cells.

It has been reported that curcumin influence both multi-drug resistance protein 1 (MRP1) multidrug resistance protein 2 (MRP2). It appears that curcumin inhibited both MRP-1 and MRP-2-mediated transport with $IC_{50}$ values of 15 uM and 5 uM. Wortelboer, *Chem. Res. Toxicol.*, 2003 December 16: 12, 1642-51. Wortelboer also recognized the "complex interplay between MRP inhibition and metabolism of MRP inhibitors. Chearwae, *Cancer Chemother. Pharmacol.*, 2006, February 57(3) 376-88 reports curcumin to inhibit MRP1, with an IC50 of about 14.5 uM.

Of note, Hong, *Biochem. Biophys. Res. Comm.* 2003 Oct. 10, 310(1) 222-7 reports that the inhibition of MRPs by curcumin led to a significant increase in the amount of green tea catechin EGCG in MDCKII/MRP1 and HT-29 cells. Therefore, there is a special advantage in providing both curcumin and EGCG in the same formulation, as curcumin can provide therapeutic benefits and increase the bioavailability of EGCG.

It appears that curcumin is metabolized mainly through glucuronidation. Pan, *Drug Metab. Dispos.*, 1999, 27, 1, 486-494. However, it has been repeatedly demonstrated that curcumin also inhibits glucuronidation. Basu, *Drug. Metab. Dispos.*, 2004, July 32(7) 768-73 reports that curcumin transiently inhibits MPA glucuronidation in both human LS180 colon cells and mouse duodenum. Basu, *PNAS*, May 3, 2005, 102(18) 6285-90 reports the inhibition of cellular UGT1a7 and UGT1A10 activities after exposure to curcumin. Basu, *J. Biol. Chem.*, 279, Jan. 9, 2004, 1429-1441 reports that curcumin reversible targets UGTs causing inhibition. In general, curcumin appears to provide its maximum inhibition of UGT activity about 1-2 hours after exposure. Basu, *Biochem. Biophys. Res. Comm.*, 303(2003) 98-104 (FIG. 1) reports that the inhibition of UGT1A1 by curcumin can reach about 95% after about one hour after exposure, returning to about 80% of the control value after about 10 hours. Naganuma, *Biol. Pharm. Bull.*, 2006 Jul. 29 (7) 1476-9 reports the moderate inhibition of UGT activity in the conjugation of 1-naphthol in Caco-2 cells by curcumin.

Because of the strong inhibition of UGTs by curcumin, curcumin has been proposed as a pre-treatment for cancer chemotherapy, and it has been reported that transient inhibition of glucuronidation by oral pretreatment with curcumin before MPA administration caused a six-fold increase in immunosuppression of antigen-stimulated spleen cytotoxic T-lymphocyte proliferation in mice. See (http://nichd-dirsage.nichd.nih.gov:8080/ar2004/pages/hdb/sgddm.htm).

There is, however, one investigator (van der Logt, *Carcinogenesis*, 24, 10, 1651-56, 2003) that reports enhancement of UGT activity by curcumin.

Because the glucuronidation inhibition by curcumin is reversible, it appears that curcumin could be used for a pretreatment of the olfactory mucosa in order to inhibition enzymatic activity upon the later therapeutic dose of curcumin without a concern for drug-drug interactions.

Therefore, in some embodiments, a first dose of curcumin is intranasally administered to the patient (to inhibit enzyme activity in the olfactory mucosa), and then a second dose of curcumin is intranasally administered to the patient at least about 15 minutes after the first dose (to travel to the brain).

It is well known that that the cytochrome p450 enzymes are significant in the olfactory mucosa. Oetari, *Biochem. Pharmacol.*, 1996, Jan. 12, 51(1) 39-45 reports that curcumin strongly inhibits P450s in rat liver. Thapliyal, *Food Chem. Toxicol.* 2001, June 39(6) 541-7 reported the inhibition of cytochrome P450 isoenzymes by curcumins both in vitro and in vivo.

Zhou, *Drug Metab. Rev.*, 2004 February 36(1) 57-104 reports curcumin to be an inhibitor of Pgp.

In some embodiments, piperine is used as a glucuronidation inhibitor. Reen, Biochem. Pharmacol., 1993, Jul. 20, 46(2) 229-38 reports piperine to be a potent inhibitor of glucuronidation. Shoba, *Planta Med.*, 1998 May 64(4) 353-6 reports that pre-administration of piperine led to a 2000% increase in the bioavailability of curcumin in humans.

In some embodiments, the glucuronidation inhibitor is an analog of piperine. Preferably, the piperine analog is antiepilepsirine. Administration of antiepilepsirine is also effective in raising serotonin synthesis (Liu, Biochem. Pharmacol., 1984 Dec. 1, 33(23) 3883-6), and has been studied as an antiepilepsy drug (Wang, *Brain Dev.* 1999 Jan. 21 (1) 36-40). Accordingly, its intranasal administration should not lead to significant problems.

In some embodiments, the glucuronidation inhibitor is a surfactant. Kurkela, *J. Biol. Chem.*, 2003 Feb. 7; 278(6) 3536-44 reports that several UGT enzymes were nearly fully inhibited by a surfactant, namely Triton X-100. Preferably, the surfactant is a non-ionic surfactant.

In some embodiments, the glucuronidation inhibitor is a mucolytic agent, such as N-acetylcysteine (NAC). Takatsuka, *Int. J. Pharm.*, 2006 Jun. 19, 316(1-2) 124-30, reports that co-administration of a mucolytic agent (NAC) and a surfactant (Triton TX-100) led to enhanced intestinal absorption in a synergistic manner. It was further reported that the damage to the mucosa was reversible.

In some embodiments, the glucuronidation inhibitor is an NSAID. In preferred embodiments, the NSAID is niflumic acid. Mano, *Biopharm. Drug Dispos.*, 2006 Jan. 27 (1) 1-6 reports the inhibitory effect of NSAIDs, and niflumic acid in particular, on UGT activity.

Enzyme Inhibition by Buffer

In some embodiments, low pH buffers are used as glucuronidation inhibitors. Basu, *PNAS*, May 3, 2005, 102, 18, 6285-90 reports maximum glucuronidation of lipophiles by UGT1A7 in the pH range of 6-9, and nearly zero glucuronidation activity by UGT1A7 at pH 5. Similarly, Basu, *J. Biol. Chem.*, 279, Jan. 9, 2004, 1429-1441 reports that pH can drastically alter the level of UGT activity, and that a pH of 5 inhibits nearly all glucuronidation activity for each of UGT1A7 and UGT1A10. Therefore, it appears that low pH formulations are effective in completely inhibiting glucuronidation activity. In some embodiments of the present invention, the curcumin formulation contains a buffer setting a pH of between about 3.0 and 5.5, preferably a pH of between about 3.5 and 5, preferably a pH of between about 4 and 5. In some embodiments of the present invention, the curcumin formulation contains a buffer setting a pH of between about 3 and 4. Below these cited ranges, there is a chance that the acidic nature of the formulation will be irritating to the nasal cavity. Above this range, there may be minimal inhibition of glucuronidation. U.S. Pat. No. 6,187,332 ("Gem") discloses a buffered flowable nasal spray formulation having a pH of between 4 and 5 which is able to maintain its pH for prolonged periods in the human nose. Gem discloses formulation comprising citrate and phosphate buffering agents.

Therefore, in accordance with the present invention, there is provided an intranasal spray device comprising a formulation comprising:

a) an effective amount of curcumin, and b) a buffering agent (preferably, a citrate or phosphate) having a pH of between 4 and 5 which is able to maintain the pH of the formulation between 4 and 5 in the human nose for prolonged periods.

Absorption Enhancers

In some embodiments, the absorption enhancer is a bile salt. Chavanpatil, *Pharmazie,* 2005 May, 60(5) 347-9. In preferred embodiments, the bile salt is selected from the group consisting of sodium deoxycholate, sodium caprate, and sodium tauroglycocholate and EDTA.

In some embodiments, magnesium$^{+2}$ is used as a glucuronidation inhibitor. Wong, *Biochem. J.*, (1968) 110, 99 reports that Mg$^{+2}$ concentrations in excess of about 10 mM were effective in inhibiting about 85% of enzymatic glucuronidation activity.

Cooling

It is appreciated by the inventors that the UGT enzyme is likely very sensitive to temperature. Therefore, it is reasonable to expect that a decrease in the temperature of the mucosal lining will result in a decrease in the enzymatic glucuronidation of curcumin by the UGTs. Indeed, it has been reported by Castuma, *Biochem. J.*, (1989) 258, 723-731 that the enzymatic activity of UDP-glucuronyltransferase in normal liver microsomes of guinea pigs decreased about 3-fold when the temperature of the microsomes was reduced from about 37° C. to about 10° C.

Therefore, the present inventors have devised inventions based upon the temporary cooling of the nasal mucosa in order to inhibit the glucuronidation of curcumin.

In one embodiment, the formulation of the present invention contains a cooling agent such as menthol.

In one embodiment, the formulation of the present invention contains an endothermic solute. In preferred embodiments, the endothermic solute is a strong salt, acid or base that dissolves in water by an endothermic process. More preferably, the endothermic solute is a salt.

In some embodiments, the endothermic solute may be selected from the group consisting of sodium bicarbonate ($\Delta H=+19.1$ kJ/mol); potassium bicarbonate ($\Delta H=+5.3$ kcal/mol); potassium sulfate ($\Delta H=+23.7$ kJ/mol); potassium chloride ($\Delta H=+17.2$ kJ/mol); sodium chloride ($\Delta H=+3.9$ kJ/mol); and potassium dihydrogenphosphate ($\Delta H=+19.6$ kJ/mol).

In some embodiments, the endothermic solute may be magnesium sulfate, which would both promote cooling and inhibition glucuronidation.

Therefore, in accordance with the present invention, there is provided an intranasal spray device comprising a formulation comprising:

a) an effective amount of curcumin, and
b) an endothermic solute (preferably magnesium sulfate)

It is well known that curcumin is poorly soluble in water. Because the olfactory mucosa is aqueous-based, the transport of curcumin from the formulation across the olfactory mucosa is problematic.

Therefore, in order to increase the transport of curcumin across the olfactory mucosa, in some embodiments, the curcumin is delivered in a formulation comprising an effective amount of a curcumin-miscible solvent. Preferably, the solvent is selected from the group consisting of DMSO and ethanol. It is well known that curcumin is highly soluble in DMSO and ethanol. When this formulation is applied to the nasal mucosa, the solvent mixes with the water in the olfactory mucosa and renders curcumin soluble in that mixture.

In preferred embodiments, the solvent is DMSO. DMSO is non-toxic and also can temporarily open the blood brain barrier. Kleindienst, *Acta Neurochir. Suppl.* 2006; 96, 258-62, and Scheld, *Rev. Infect. Dis.,* 1989 November-December; 11 Suppl 7; S1669-90.

Therefore, in accordance with the present invention, there is provided an intranasal spray device comprising a formulation comprising:

a) an effective amount of curcumin, and
b) a solvent selected from the group consisting of DMSO and ethanol.

Increasing Solubility

Some embodiments increase the solubility of curcumin in water by employing a solid dispersion, such as those made with polyethylene glycol 6000 (PEG 6000) or polyvinylpyrrolidone K-30 (PVP K30). Ruan, *J. Pharm Biomed. Anal.* 2005 Jul. 1; 38(3):457-64. Paradkar, *Int. J. Pharm.* 2004 Mar. 1; 271(1-2):281-6

Some embodiments increase the solubility of curcumin in water by employing inclusion complexes, such as those made with beta-cyclodextrin (BCD) and hydroxypropyl-beta-cyclodextrin (HPBCD). Ruan, *J. Pharm Biomed. Anal.* 2005 Jul. 1; 38(3):457-64.

In some embodiments, the curcumin may be delivered in the form of a curcumin-PEG conjugate made in accordance with PCT Published Patent Application WO2008051474 and U.S. Provisional Application No. 60/862,057, filed Oct. 19, 2006, (collectively "Safavy") the specifications of which are incorporated by reference in their entireties. Safavy reports that the water solubility of one of these curcumin-PEG conjugates is about 1.5 g/ml.

Other Curcumin Analogs

Modifications of curcumin and its functional fragments that either enhance or do not greatly affect the ability to treat AD are also included within the term "curcumin." Such modifications include, for example, additions, deletions or replacements of one or more functional groups. These modifications will either enhance or not significantly alter the structure, conformation or functional activity of curcumin or a functional fragment thereof. Additionally, curcumin or its functional fragments can be modified by the addition of epitope tags or other sequences that aid in its purification and which do not greatly affect its activity. As used herein, the term "functional fragment," in connection with an curcumin, is intended to mean any portion of curcumin that maintains its to inhibit oxidation, or to prevent beta amyloid oligomer formation. If desired, a functional fragment can include regions of the curcumin with activities that beneficially cooperate with the ability to inhibit oxidation or oligomer formation.

Also in accordance with the present invention, publicly known analogs of curcumin may be used.

In some embodiments, the curcumin analogs are those found in U.S. Published patent application U.S. 2006/0067998.

Curcumin is soluble in ethanol, alkalis, ketones, acetic acid and chloroform. It is insoluble in water. Curcumin is therefore lipophilic, and generally readily associates with lipids, e.g. many of those used in the colloidal drug-delivery systems of the present invention. In certain embodiments, curcumin can also be formulated as a metal chelate.

As used herein, curcumin analogues are those compounds which due to their structural similarity to curcumin, exhibit anti-proliferative or pro-apoptotic effects on cancer cells similar to that of curcumin. Curcumin analogues which may have anti-cancer effects similar to curcumin include Ar-tumerone, methylcurcumin, demethoxy curcumin, bis-demethoxycurcumin, sodium curcuminate, dibenzoyl-methane, acetylcurcumin, feruloyl methane, tetrahydrocurcumin, 1,7-bis(4-hydroxy-3-methoxyphenyl)-1,6-heptadiene-3,5-dione (curcumin1), 1,7-bis(piperonyl)-1,6- heptadiene-3,5-dione(piperonyl curcumin)1,7-bis(2-hydroxy naphthyl)-1,6-heptadiene-2,5-dione(2-hydroxyl naphthyl curcumin), 1,1-bis(phenyl)-1,3,8,10-undecatetraene-5,7-dione (cinnamyl curcumin) and the like (Araujo and Leon, 2001; Lin et al., 2001; John et al., 2002; see also Ishida et al., 2002). Curcumin analogues may also include isomers of curcumin, such as the (Z,E) and (Z,Z) isomers of curcumin. In a related embodiment, curcumin metabolites which have anti-cancer effects similar to curcumin can also be used in the present invention. Known curcumin metabolites include glucoronides of tetrahydrocurcumin and hexahydrocurcumin, and dihydroferulic acid. In certain embodiments, curcumin analogues or metabolites can be formulated as metal chelates, especially copper chelates. Other appropriate derivatives of curcumin, curcumin analogues and curcumin metabolites appropriate for use in the present invention will be apparent to one of skill in the art.

In some embodiments, the curcumin analogs are those found in U.S. Published patent application U.S. 2005/0181036.

Commercial curcumin includes three major components: curcumin (77%), demethoxycurcumin (17%), and bisdemethoxycurcumin (3%), which are often referred to as "curcuminoids." As used herein, "curcumin" is defined to include any one or more of these three major components of commercial curcumin, and any active derivative of these agents. This includes natural and synthetic derivatives of curcumin and curcuminoids, and includes any combination of more than one curcumenoid or derivative of curcumin. Derivatives of curcumin and curcumenoids include those derivatives disclosed in U.S. Patent Application Publication 20020019382, which is herein specifically incorporated by reference.

In some embodiments, the curcumin analogs are those found in U.S. Published patent application U.S. 2005/0267221:

In certain aspects, 1,7,-bis(4-hydroxy-3-methoxyphenyl)-1,6-heptadi-ene-3,5-dione is the curcumin that may be used in the present invention. Other curcumin analogues (curcuminoids) that may be used include, for example, demethoxycurcumin, bisdemethoxycurcumin, dihydrocurcumin, tetrahydrocurcumin, hexahydrocurcumin, dihydroxytetrahydrocurcumin, Yakuchinone A and Yakuchinone B, and their salts, oxidants, reductants, glycosides and esters thereof. Such analogues are described in U.S. Patent Application 20030147979; and U.S. Pat. No. 5,891,924 both of which are incorporated in their entirety herein by reference.

Other curcumin analogues (curcuminoids) that may be used include dihydroxycurcumin and NDGA.

Further examples of curcumin analogues include but are not limited to (a) ferulic acid, (i.e., 4-hydroxy-3-methoxycinnamic acid; 3,4-methylenedioxy cinnamic acid; and 3,4-dimethoxycinnamic acid); (b) aromatic ketones (i.e., 4-(4-hydroxy-3-methoxyphenyl)-3-buten-2-one; zingerone; -4-(3,4-methylenedioxyphenyly-2-butanone; 4-(p-hydroxyphenyl)-3-buten-2-one; 4-hydroxyvalerophenone; 4-hydroxybenzylactone; 4-hydroxybenzophenone; 1,5-bis (4-dimethylaminophen-yl)-1,4-pentadien-3-one); (c) aromatic diketones (i.e., 6-hydroxydibenzoylmethane) (d) caffeic acid compounds (i.e., 3,4-dihydroxycinnamic acid); (e) cinnamic acid; (f) aromatic carboxylic acids (i.e., 3,4-dihydroxyhydrocinnainic acid; 2-hydroxycinnamic acid; 3-hydroxycinnamic acid and 4-hydroxycinnamic acid); (g) aromatic ketocarboxylic acids (i.e., 4-hydroxyphenylpyruvic acid); and (h) aromatic alcohols (i.e., 4-hydroxyphenethyl alcohol). These analogues and other representative analogues that can be used in the present invention are further described in WO9518606 and WO01040188, which are incorporated herein by reference in their entirety.

Curcumin or analogues thereof may be purified from plants or chemically synthesized using methods well known and used by those of skill in the art. Plant-derived curcumin and/or its analogues can be obtained by extraction from plants including Zingiberaceae Curcuma, such as Curcuma longa (turmeric), Curcuma aromatica (wild turmeric), Curcuma zedoaria (zedoary), Curcuma xanthorrhiza, mango ginger, Indonesian arrowroot, yellow zedoary, black zedoary and galangal. Methods for isolating curcuminoids from turmeric are well known in the art (Janaki and Bose, 1967). Still further, curcumin may be obtained from commercial sources, for example, curcumin can be obtained from Sigma Chemicals Co (St. Louis, Mo.).

Any conventional method can be used to prepare curcumin and its analogues to be used in the present invention. For example, turmericoleoresin, a food additive, which essentially contains curcumin, can be produced by extracting from a dry product of rhizome of turmeric with ethanol at an elevated temperature, with hot oil and fat or propylene glycol, or with hexane or acetone at from room temperature to a high temperature. Alternatively, those can be produced by the methods disclosed in Japanese Patent Applications 2000-236843, H-11-235192 and H-6-9479, and U.S. Patent Application No. 20030147979, which is incorporated by reference herein in its entirety.

In certain embodiments, a purified product of at least one curcumin and/or its analogue may be used. Alternatively, a semi-purified or crude product thereof may be used, provided that it does not contain impurities which may not be acceptable as a pharmaceutical or food product.

Preferred Analogues

There has been limited testing of the potency of curcumin analogs against beta amyloid. Park, *J. Nat. Prod.*, 65, 9, September 2002, reports testing the following curcumin analogs for the ability to provide in vitro protection for PC12 cells against beta amyloid insult:

4"-(3'"-methoxy-4'"-hydroxyphenyl)-2"-oxo-3"-enebutanyl3-(3'-methoxy-4'hydroxyphenyl)propenoate (31);

1-(4-hydroxy-3-methoxyphenyl)-7-(4-hydroxyphenyl)-1,6-heptadiene-3,5-dione (demethoxycurcumin)(32);

1,7-bis(4-hydroxyphenyl)-1,6-heptadiene-3,5-dione (bis-demethoxycurcumin), (33); and 1,7-bis(4-hydroxyphenyl)-1-heptene-3,5-dione (34).

Figure 1D:
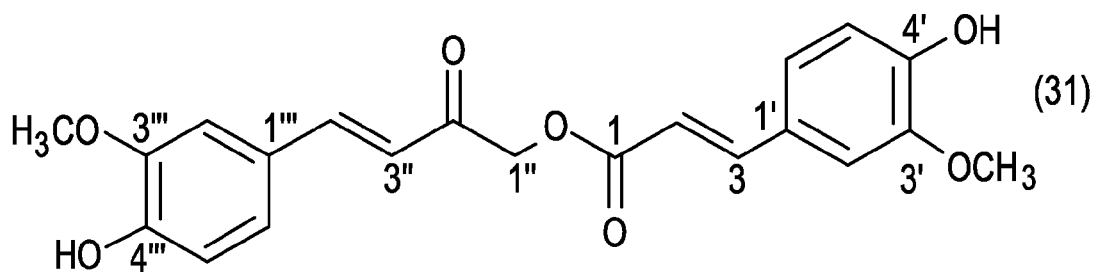
FIG. 1d discloses preferred curcumin analogs (31)-(34) that are candidate parent compounds for making prodrugs thereof.
Figure 1D:
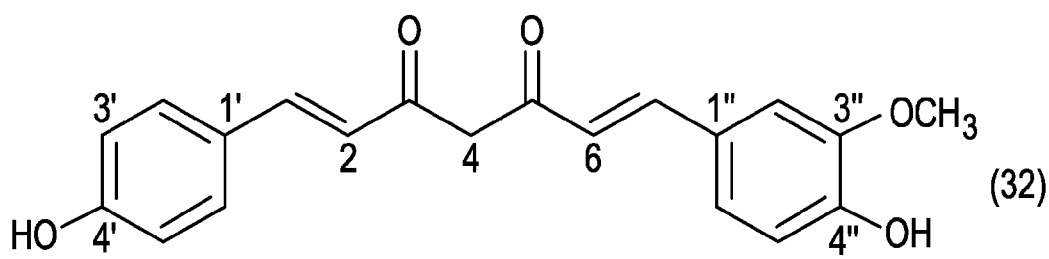
Figure 1D:
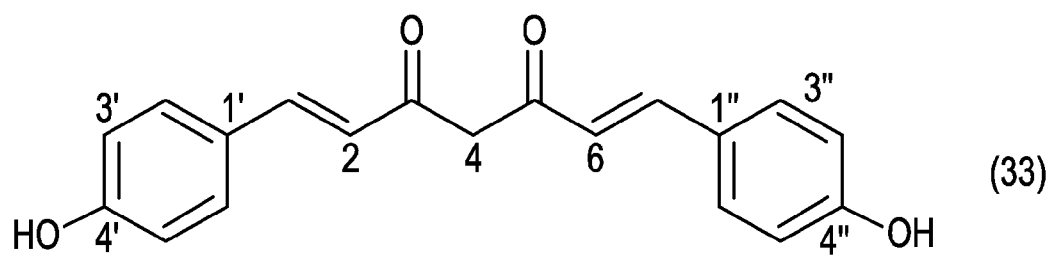
Figure 1D:
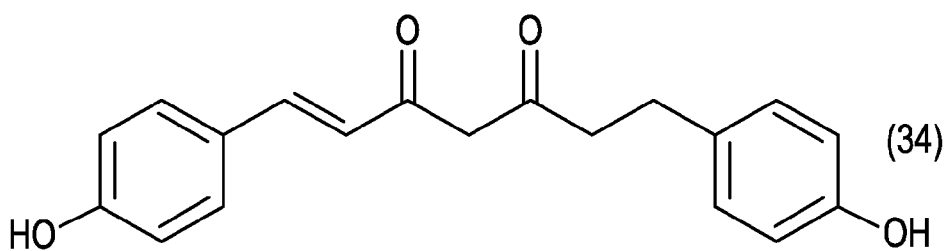

Each of these compounds is shown in FIG. 1d. Park reports the following results, as shown in Table IV:

TABLE IV

| Analog | anti-βA (25-35) ED50$^a$ (µg/ml) | anti-βA (1-42) ED50 (µg/ml) |
|---|---|---|
| curcumin | 7.0 +/− 1.1 | 10.0 +/− 0.9 |
| 31 | 1.0 +/− 0.3 | 2.0 +/− 0.4 |
| 32 | 4.0 +/− 0.5 | 5.0 +/− 0.5 |
| 33 | 2.0 +/− 0.6 | 3.5 +/− 0.7 |
| 34 | 0.5 +/− 0.2 | 1.0 +/− 0.3 |

$^a$ED50 represents the sample concentration that is required to achieve 50% cell viability.

Analysis of the Park data reveals that each of compounds (31)-(34) is a more potent neuroprotectant against beta amyloid than curcumin, with compounds (31) and (34) being on the order of 5 and 10 fold more potent. Therefore, in preferred embodiments, each of compounds (31)-(34) is used by itself or in combination as the parent compound for the manufacturing and use of a curcumin prodrug. Each of the parent compounds may be obtained by the methods disclosed in Park.

Kim, *Neuroscience Lett.* 303 (2001) 57-61 similarly reports testing the following curcumin analogs for the ability to provide in vitro protection for PC12 cells against beta amyloid insult as shown in Table V:

TABLE V

| Analog | anti-BA (25-35) ED50 (µg/ml) | anti-BA (1-42) ED50 (µg/ml) |
|---|---|---|
| Curcumin | 7.1 +/− 0.3 | 6.8 +/− 0.4 |
| Demethoxycurcumin | 4.7 +/− 0.1 | 4.2 +/− 0.3 |
| Bisdemethoxycurcumin | 3.5 +/− 0.2 | 3.0 +/− 0.3 |

Analysis of the Kim data reveals that each of the demethoxycurcumin and bisdemethoxycurcumin compounds is a more potent neuroprotectant against beta amyloid than curcumin, with the demethoxycurcumin and bisdemethoxycurcumin compounds being on the order of 1.5 and 2 fold more potent. This data is in substantial agreement with the relative potencies of demethoxycurcumin and bisdemethoxycurcumin reported by Park above.

From Chen, *Free Rad. Biol. Med.*, 2006 Feb. 1; 40(3):526-35, the compounds hydroxycurcumin and dihydroxycurcumin can be obtained by demethylation of curcumin with $AlCl_3$-pyridine as described in Mazumder, "Curcumin analogs with altered potencies against HIV-1 integrase as probes for biochemical mechanism of drug action, *J. Med. Chem.* 40 (1997), pp. 3057-3063.

Phenyl ring-substituted analogues of curcumin can be synthesized by condensation of 2,4-pentanedione with two equivalents of the substituted benzaldehyde based on the available methods, such as those described in Mazumder, "Curcumin analogs with altered potencies against HIV-1 integrase as probes for biochemical mechanism of drug action", *J. Med. Chem.* 40 (1997), pp. 3057-3063; U.S. Pat. No. 6,900,356 (Gokaraju), the specification of which is incorporated by reference in its entirety; and Roughley, "Experiments in biosynthesis of curcumin", *J. Chem. Soc. Perkin Trans.* 1 (1973), pp. 2379-2388.

Generally, as described in Chen, *Free Rad. Biol. Med.*, 2006 Feb. 1; 40(3):526-35, 2,4-pentanedione (1.0 g, 0.01 mol) and boron oxide (0.49 g, 0.007 mol) can be dissolved in EtOAc (10 ml) and stirred for 0.5 h at 40° C. followed by addition of the corresponding benzaldehyde (0.02 mol) and tributyl borate (4.6 g, 0.02 mol) and stirred for additional 0.5 h. Then n-butylamine (1 ml) in EtOAc (10 ml) can be added dropwise during 30 min. After further stirring for 4 h at 40° C. the mixture can be allowed to stand overnight to complete the reaction. The mixture can then be hydrolyzed by HCl (0.4 N, 15 ml) and the aqueous layer can be extracted three times with EtOAc. The combined organic layers can be washed with water and dried over $Na_2SO_4$. After removal of the solvent under reduced pressure the residual paste can be purified by column chromatography (silica gel, cyclohexane-EtOAc) and recrystallized from EtOH to give pure curcumin analogs.

Other Diseases

In other embodiments, the present invention relates to the intranasal administration of a formulation comprising an effective amount of curcumin across the cribriform plate and into the brain in order to treat a stroke.

In other embodiments, the present invention relates to the intranasal administration of a formulation comprising an effective amount of curcumin across the cribriform plate and into the brain in order to treat multiple sclerosis.

Other Polyphenolic Prodrugs

In some embodiments, the curcumin is combined with a second lipophilic therapeutic agent, preferably another polyphenol, such as resveratrol. In some embodiments, the curcumin is provided in a formulation with another compound selected from the group consisting of gingko biloba extract, resveratrol, and a green tea catechin, and then is intranasally administered.

Also in accordance with the present invention, there is provided a method for transporting a gingko biloba extract to a brain of a mammal, comprising: a) applying a pharmaceutical composition comprising a gingko biloba extract to an upper third of a nasal cavity of the mammal, wherein the gingko biloba extract is absorbed through an olfactory mucosa and transported to the brain of the mammal.

Also in accordance with the present invention, there is provided a method for transporting resveratrol to a brain of a mammal, comprising:
a) applying a pharmaceutical composition comprising resveratrol to an upper third of a nasal cavity of the mammal, wherein the resveratrol is absorbed through an olfactory mucosa and transported to the brain of the mammal.

Also in accordance with the present invention, there is provided a method for transporting a green tea catechin to a brain of a mammal, comprising:
a) applying a pharmaceutical composition comprising the catechin to an upper third of a nasal cavity of the mammal, wherein the catechin is absorbed through an olfactory mucosa and transported to the brain of the mammal.

The prodrug rationale provided above for curcumin can also be applied to other therapeutic phenolic compounds (preferably, therapeutic polyphenolic compounds), such as those of the flavonoid class. In preferred embodiments, this compound is selected from the group consisting of resveratrol, hispidin, genistein, ellagic acid, 1,25 dihydroxyvitamin D3, the green tea catechin EGCG, and docosahexaenoic acid (DHA). In another embodiment, this compound is docosahexaenoic acid (DHA). Also in accordance with the present invention, there is provided a method for transporting a flavonoid prodrug to a brain of a mammal, comprising:
a) applying a pharmaceutical composition comprising a flavonoid prodrug (such as a resveratrol prodrug) to an upper third of a nasal cavity of the mammal, wherein the flavonoid prodrug is absorbed through an olfactory mucosa and transported to the brain of the mammal.

Resveratrol

In especially preferred embodiments, the flavonoid prodrug is resveratrol.

Resveratrol, a polyphenolic compound commonly found in red wine, has been promoted as a possible treatment for Alzheimer's Disease because it appears to affect multiple mechanisms of AD pathology. Anekonda, *Brain Research Reviews*, 52, 2006, 316-26.

First, resveratrol has been shown to reduce the amount of beta amyloid in brain tissue. The mechanism by which resveratrol accomplishes this has been subject to debate. One recent paper concludes that resveratrol is a specific inhibitor of BACE1 enzyme, with an $IC_{50}$ of about 15 uM. Jeon, *Phyomedicine*, 2006 Nov. 2 (E-pub). Another recent paper reports that resveratrol reduces beta amyloid content by promoting intracellular degradation of beta amyloid via a mechanism that involves the proteosome. Marambaud, *J. Biol. Chem.*, 280(45), 37377-82.

Second, it is believed that resveratrol inhibits the formation of beta amyloid fibrils. Riviere, *Bioorg. Med. Chem.*, 2006 Oct. 1 (E-pub).

Third, 20 μM resveratrol has a neuroprotective effect against beta amyloid-induced neurotoxicity in rat hippocampal neurons, and is believed to provide this neuroprotection through activation of protein kinase C (PKC). Han, *Br. J. Pharmacology*, 2004, 141, 997-1005. Han, *J. Pharmacol. Exp. Ther.*, 2006 July 318(1)238-45 (Epub 2006 March 30), reports the existence of specific plasma membrane binding sites for resveratrol in the rat brain (Ki=102 nM), and notes that the potency of resveratrol analogs in protecting rat hippocampal cells against beta amyloid-induced neurotoxicity correlates well with their apparent affinity.

The hypothesis that resveratrol acts through PKC is of special interest because it is believed that nonamyloidogenic processing of amyloid precursor protein (APP) also acts through activation of PKC.

Fourth, some hypotheses of Alzheimer's Disease involve oxidation via enhanced brain concentrations of heavy metals. Respecting resveratrol, it has been reported that resveratrol is a highly potent chelator of copper. Belguendouz, *Biochemical Pharmacology*, 53, 1347-1355, 1997.

Fifth, Anekonda, *Brain Research Reviews*, 52, 2006, 316-26 reports that mechanisms of aging and AD are intricately linked and that these mechanisms can be modulated by both calorie restriction regimens and calories restriction mimetics, the prime mediator of which is the SIRT1 protein. Howitz, *Nature*, 2003, 425, 191-196 reports that resveratrol has been found to exhibit the highest level of SIRT1 activation amongst the small molecules tested. Chen, *J. Biol. Chem.*, 280, 48, 40364-74 found that resveratrol markedly reduced NF-KB signaling in microglia, and ascribed this benefit to the induction of SIRT1 by resveratrol. Similarly, Kim, *Int. J. Mol. Med.*, 2006 Jun. 17, 6, 1069-75 reports that modulation of NF-KB activity is involved in the neuroprotective action of resveratrol against beta amyloid induced neurotoxicity.

Sixth, resveratrol is a well known anti-oxidant, and 5-25 uM resveratrol has displayed an ability to protect cultured hippocampal cells against nitric oxide related neurotoxicity. Bastianetto, *Br. J. Pharm.*, 2000, 131, 711-720. Similarly, Savaskan, *Gerontology*, 2003 November-December, 49(6) 380-3 reports that resveratrol maintains cell viability against beta amyloid-related oxidative stress, and exerts its antioxidative action by enhancing the intracellular free radical scavenger glutathione.

The bioavailability of resveratrol has been well studied. Since resveratrol appears to be highly susceptible to glucuronidation in the intestine and liver, it has been concluded that the oral bioavailability of resveratrol is "about zero". Wenzel, *Mol. Nutr. Food Res.*, 2005, 49, 472-481. Accordingly, because of the finding that trans-resveratrol in present in human serum in its glucuronide form rather than in its free form, Vitaglione, *Mol. Nutr. Food Res.*, 2005 May 49(5), 495-504, raises some doubts about the heath effect of dietary consumption of resveratrol. Thus, the intranasal rationale for trans-resveratrol appears warranted.

Nonetheless, it appears that when resveratrol reaches the brain, it has a fairly significant residence time. El-Mohsen, *British J. Nutrition*, 2006, 96, 62-70, reports that the resveratrol concentration in the brain about 18 hours after gastric administration was still 43% of that measured at 2 hours. Wang, *Brain Research*, 958 (2002), 439-447, reports that intraperitoneal administration of resveratrol provides a peak concentration in the brain 4 hours after its administration.

Trans-resveratrol has a molecular weight of about 228, and is very lipophilic (having an octanol-water partition coefficient Log P of about 3.14). However, its solubility in water is very low (<0.01 mol/L). Thus, the prodrug rationale for trans-resveratrol appears warranted.

Hybrids

This section discloses other curcminoid drugs of the present invention that represent hybrids between curcumin and other polyphenols.

FIGS. 2-16 disclose various curcumin derivatives that are hybrids of curcumin and various other natural polyphenols. Each of these derivatives is a triphenolic compound, wherein the intermediate diketone structure of curcumin is replaced with a phenolic group. The resulting compound retains the spacing between the two phenols of curcumin, and also possesses the biphenolic spacing of the additional polyphenol.

Figure 2:
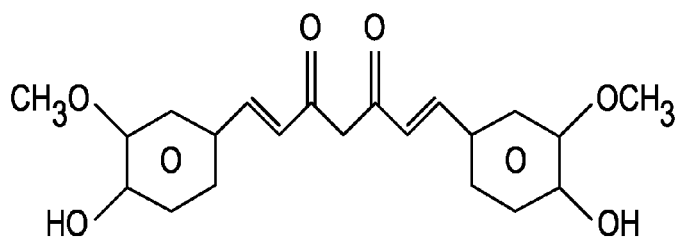
FIGS. 2-16 disclose various curcumin derivatives that are hybrids of curcumin and various other natural polyphenols. Each of these derivatives is a triphenolic compound, wherein the intermediate diketone structure of curcumin is replaced with a phenolic group. The resulting compound retains the spacing between the two phenols of curcumin, and also possesses the biphenolic spacing of the additional polyphenol.
Figure 2:
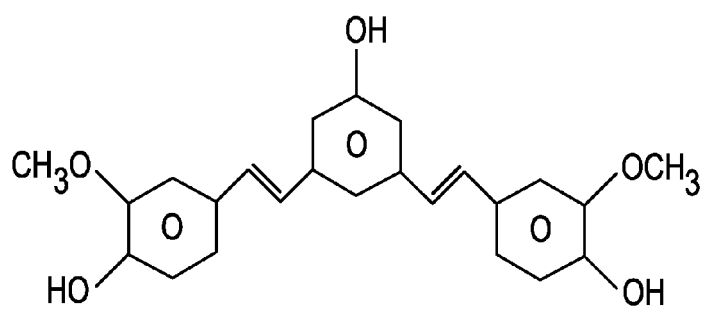
Figure 2:
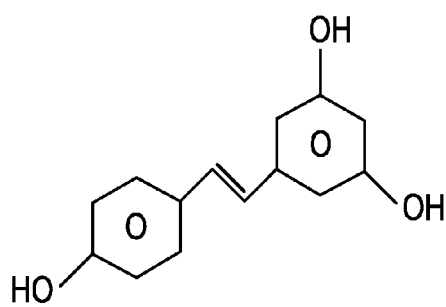
Figure 2:
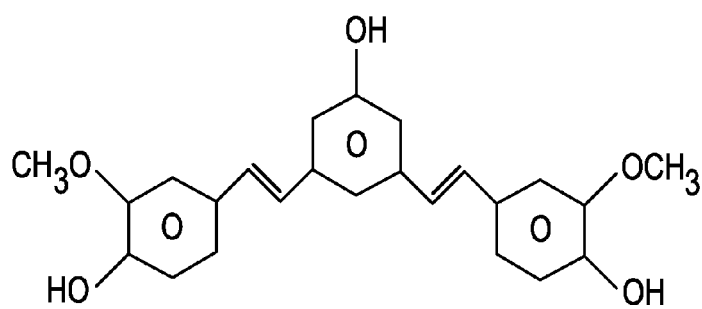

FIG. 2 discloses the structures of curcumin, resveratrol, and two curcumin-resveratrol hybrids. Note how each of the hybrids retains the interphenolic spacing of each of curcumin and reveratrol.

Figure 3:
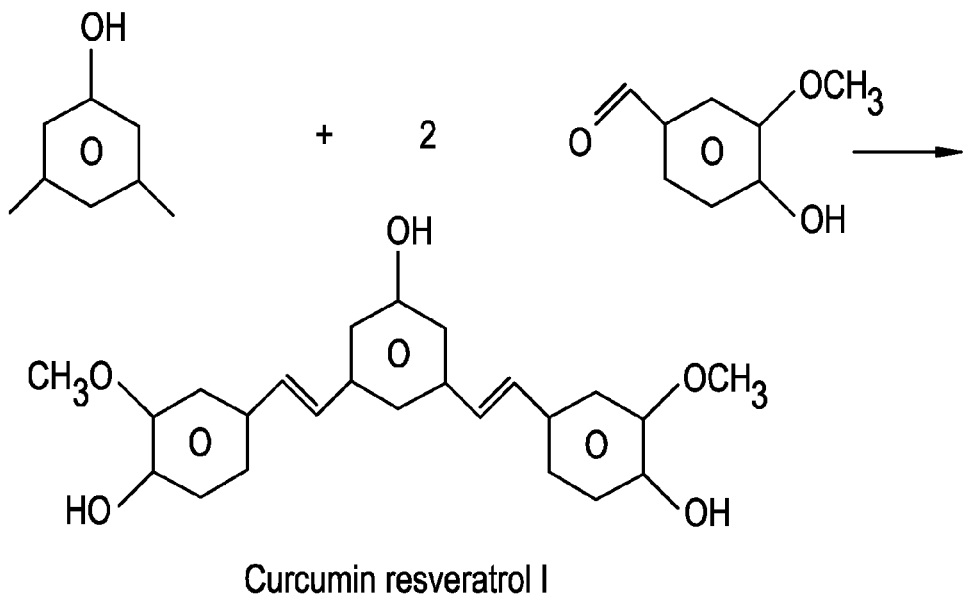

FIG. 3 discloses a method of making the curcumin-resveratrol I hybrid.

Figure 4:
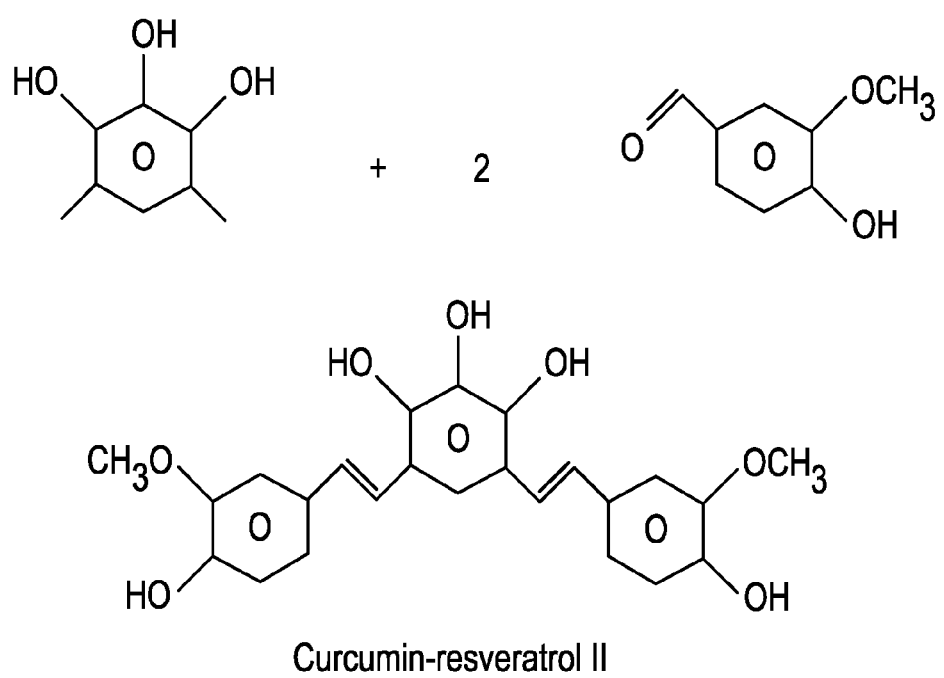

FIG. 4 discloses a method of making the curcumin-resveratrol II hybrid.

Figure 5:
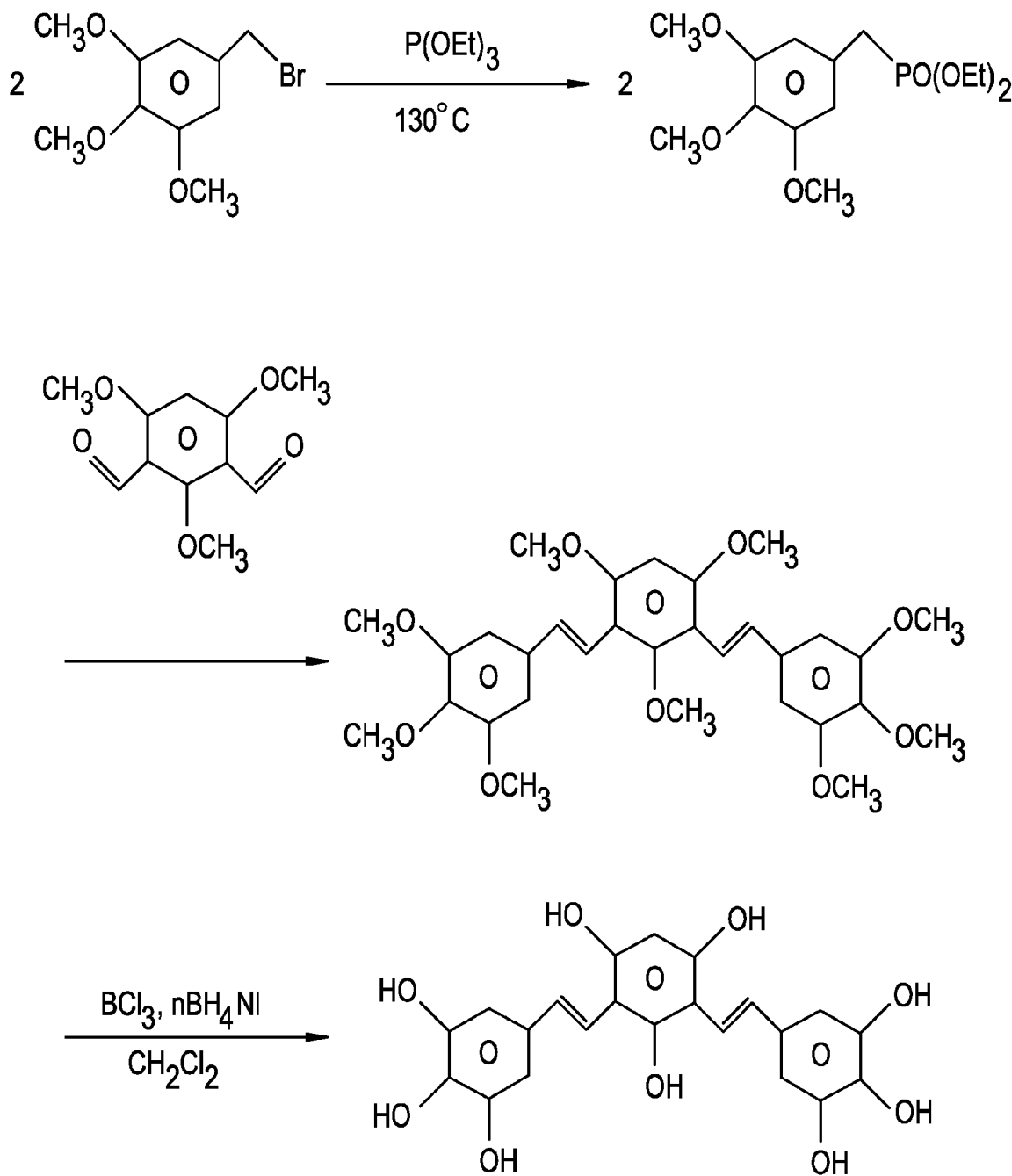

FIG. 5 discloses a method of making a curcumin-resveratrol hybrid having three hydroxyl groups in each of the central phenolic group and lateral phenolic groups.

Figure 6:
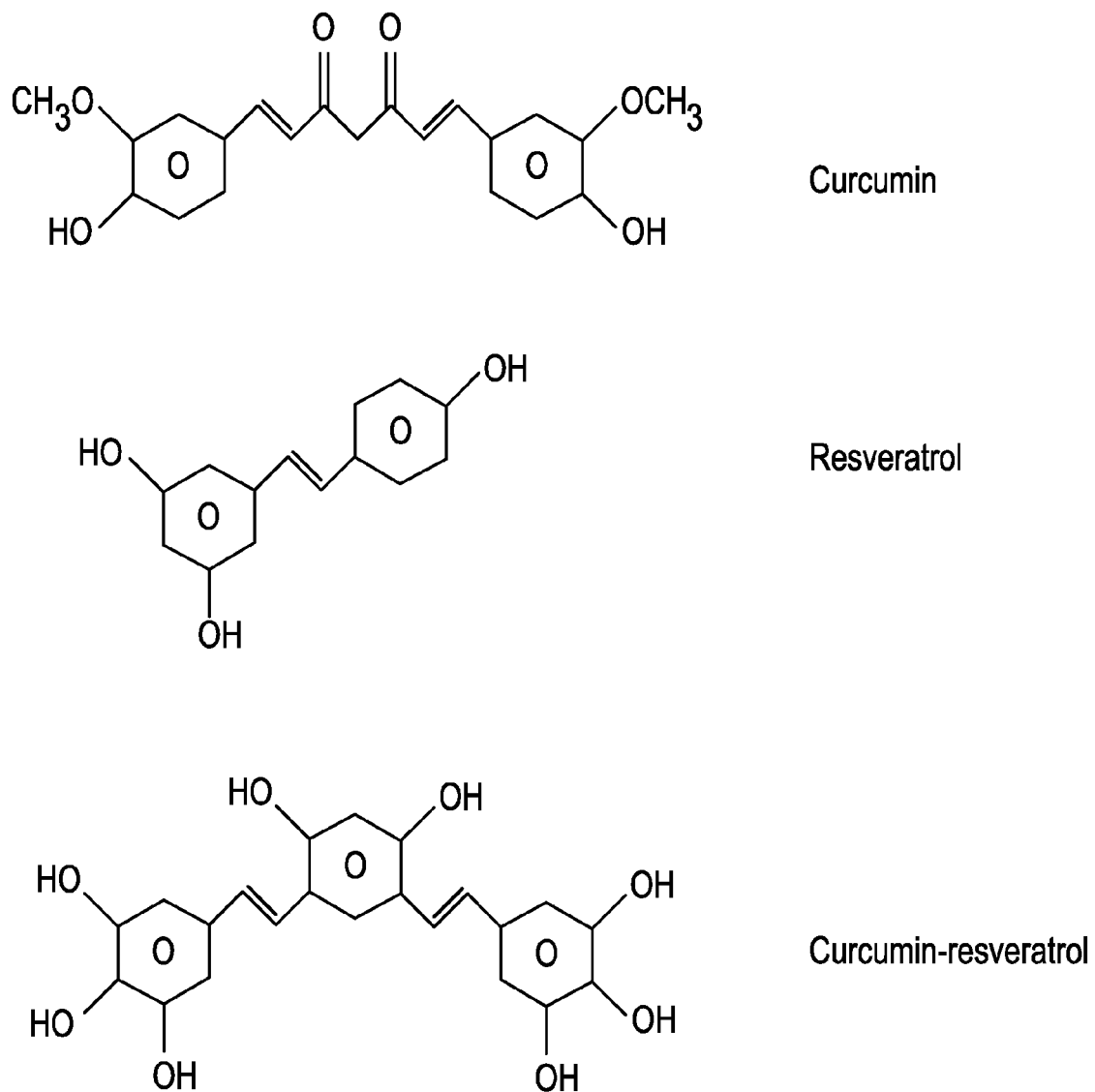

FIG. 6 discloses curcumin, resveratrol and a hybrid thereof, wherein all of the phenolics of the natural compounds are represented in the hybrid, providing trihydroxyl lateral phenolic groups and a dihydroxyl central phenolic group.

Figure 7:
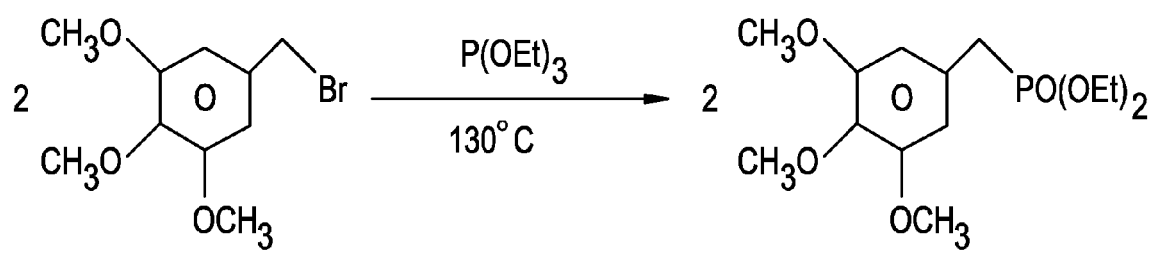
Figure 7:
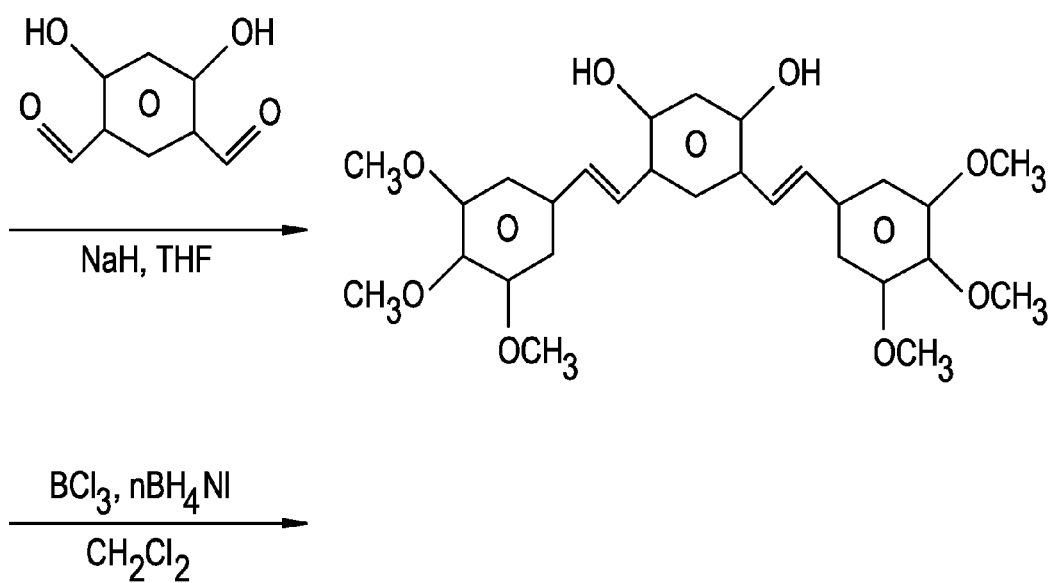
Figure 7:
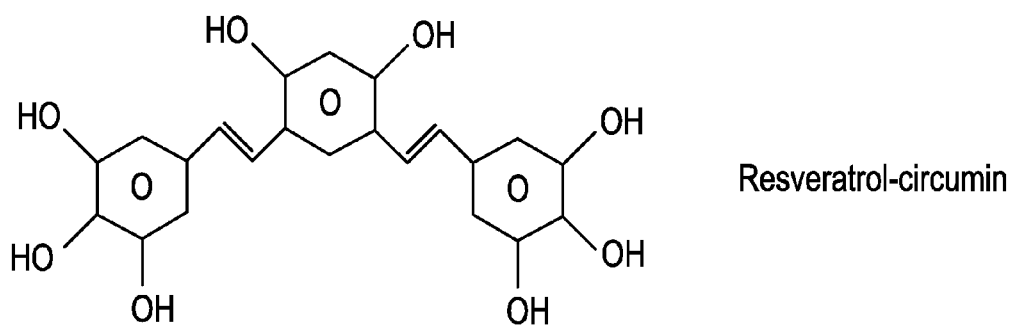

FIG. 7 discloses a method of making the curcumin-resveratrol hybrid of FIG. 6.

Figure 8:
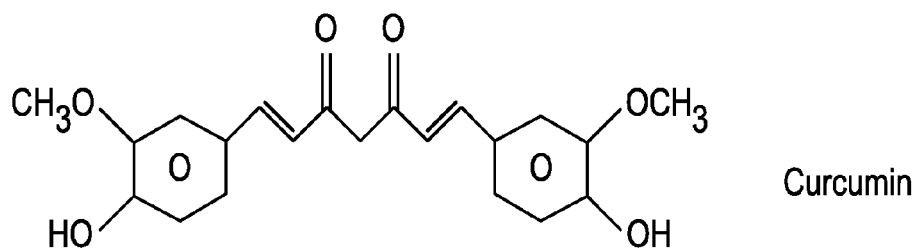
Figure 8:
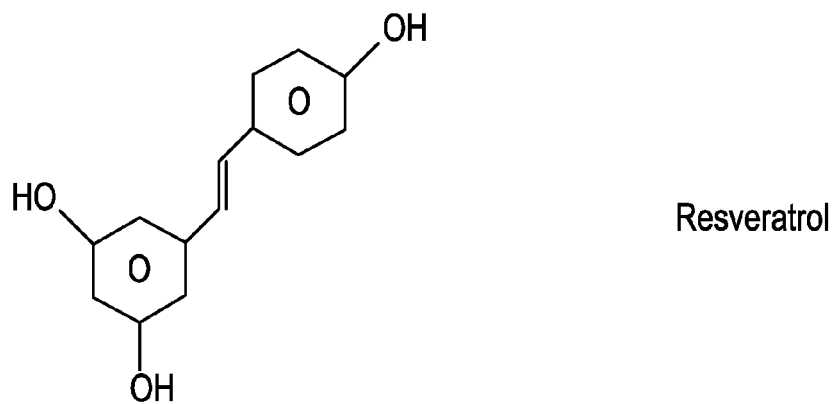
Figure 8:
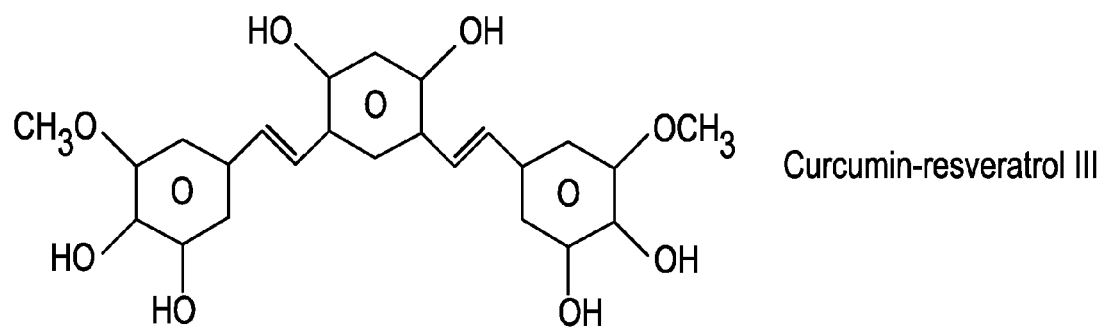

FIG. 8 is similar to the hybrid of FIG. 6, but wherein the methoxy groups of the base curcumin molecule are retained.

Figure 9:
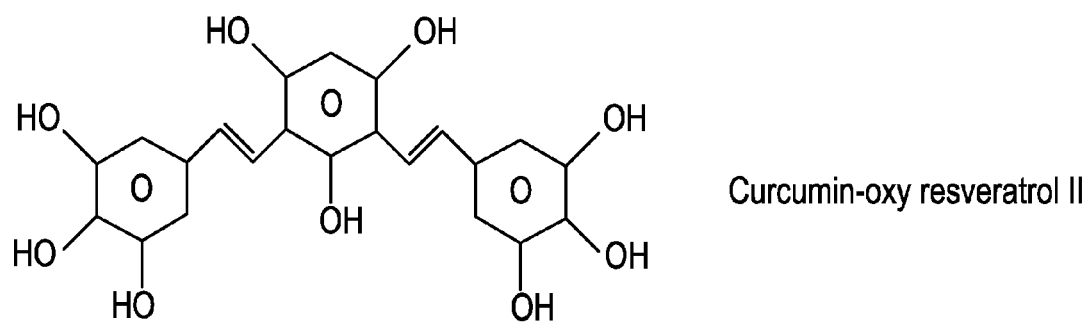
Figure 9:
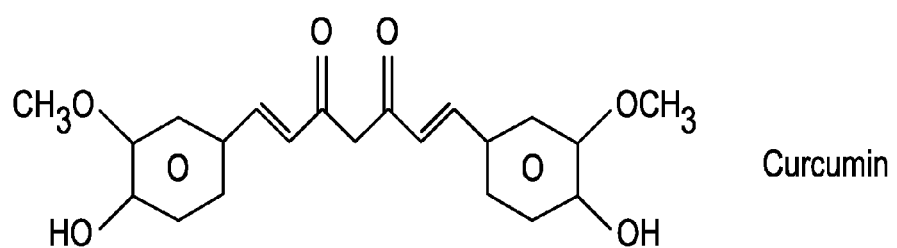
Figure 9:
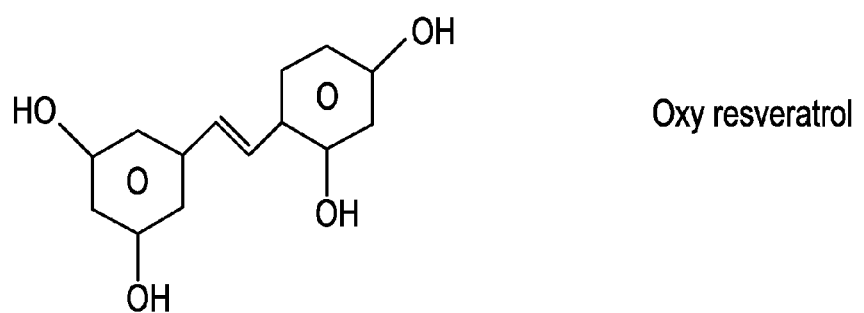

FIG. 9 discloses curcumin, oxyresveratrol and a hybrid thereof, wherein all of the hydroxyls/phenolics of the natural compounds are represented in the hybrid, providing trihydroxyl lateral phenolic groups and a trihydroxyl central phenolic group.

Figure 10:
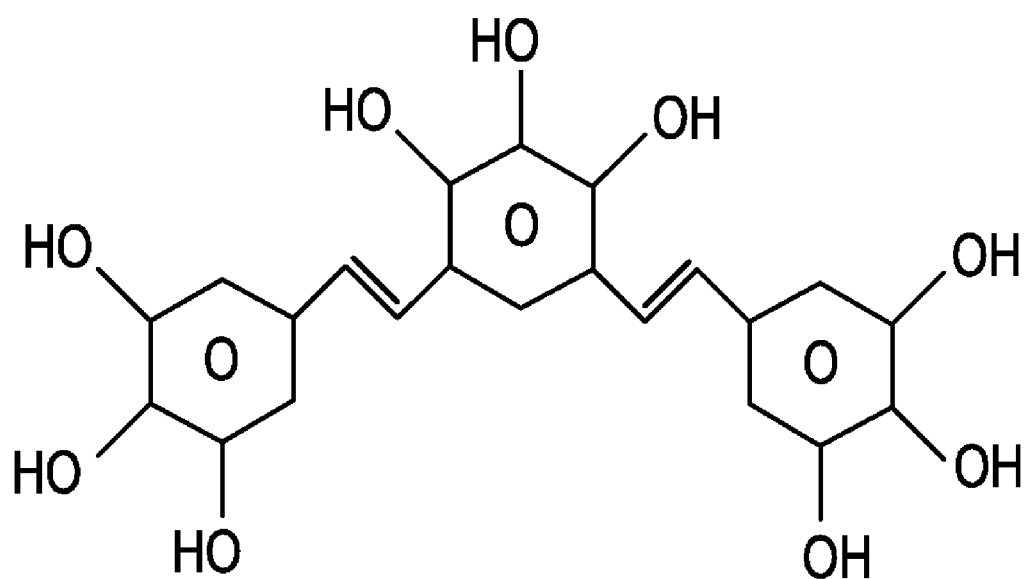

FIG. 10 discloses curcumin, piceatannol and a hybrid thereof, wherein all of the hydroxyls/phenolics of the natural compounds are represented in the hybrid, providing trihydroxyl lateral phenolic groups and a trihydroxyl central phenolic group.

Figure 11:
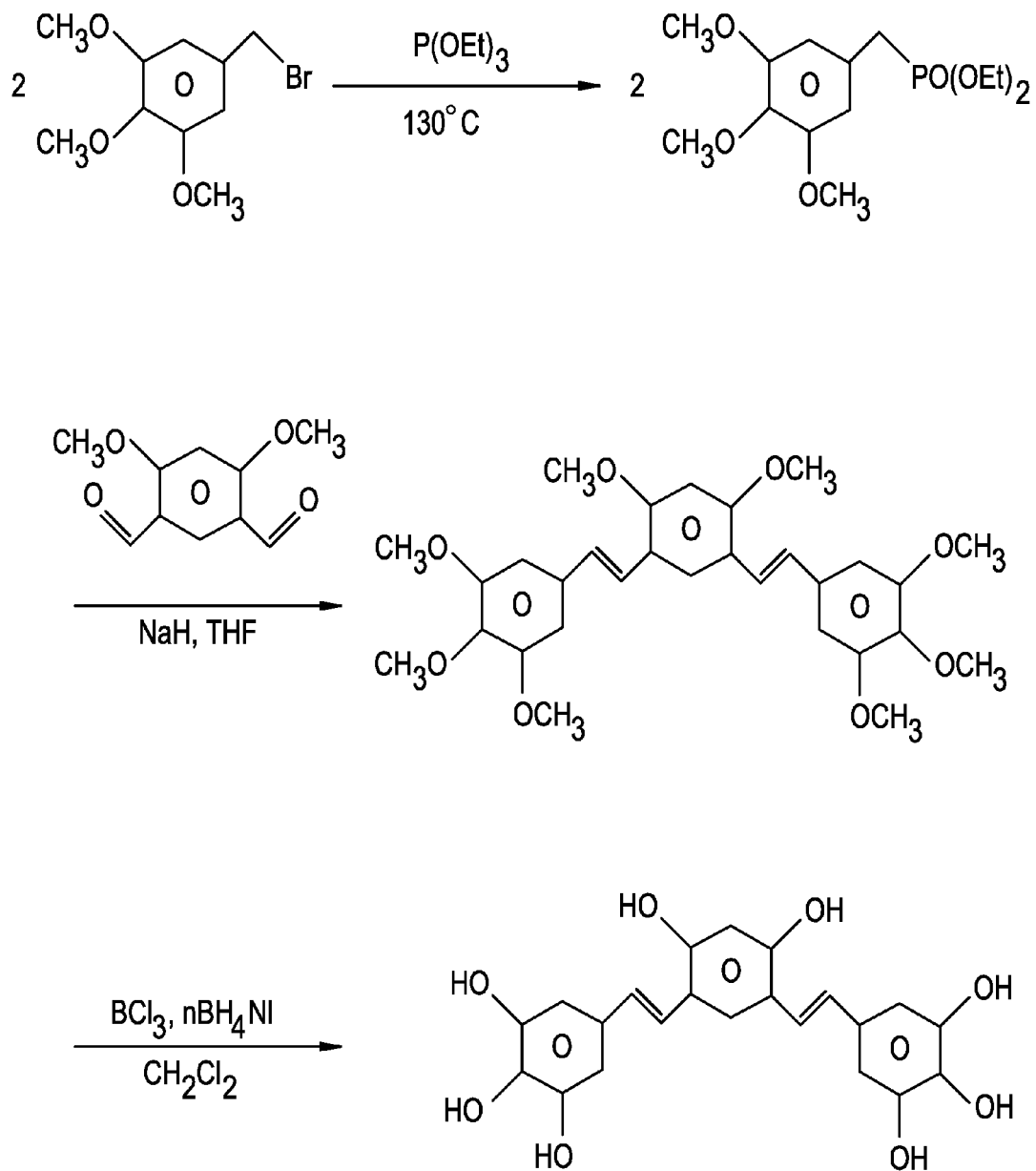

FIG. 11 discloses a method of making a curcumin-resveratrol hybrid, wherein all of the hydroxyls/phenolics of the natural compounds are represented in the hybrid, providing trihydroxyl lateral phenolic groups and a dihydroxyl central phenolic group.

Figure 12:
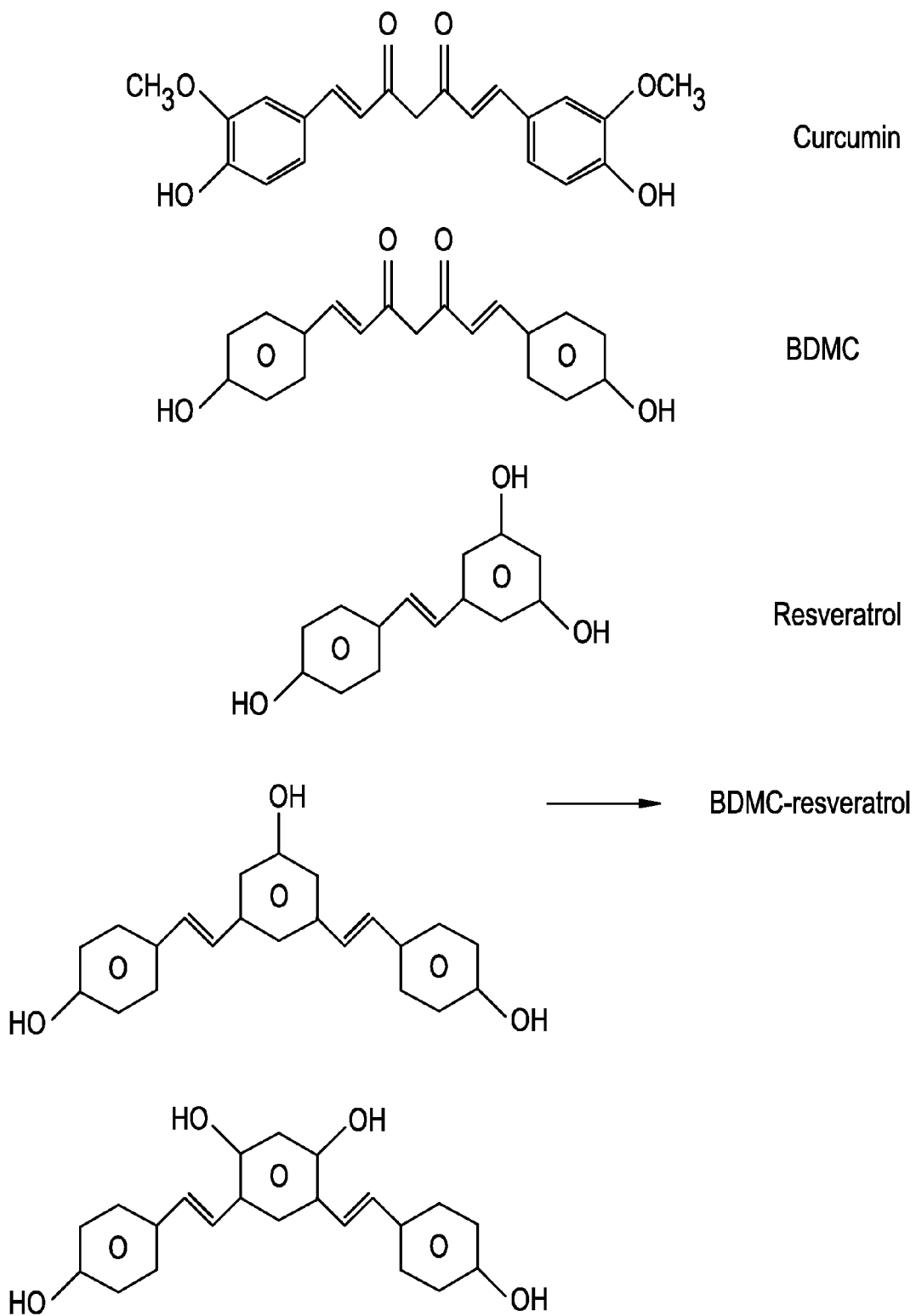

FIG. 12 discloses curcumin, BDMC, resveratrol and curcumin hybrids thereof, wherein all of the phenolics of the natural compounds are represented in the hybrid, providing hydroxyl demethoxy lateral phenolic groups and a hydroxy or dihydroxyl central phenolic group.

Narlawar, *Neurodegen. Dis.*, 2007, 4(2-3) 88-93, reports that certain oxazole and pyrazole analogs of curcumin act as inhibitors of gamma-secretase in the low micromolar range. Of interest, it has been reported that these oxazole and pyrazole analogs have substantially the same anti-oxidant activity as natural curcumin. Selvam, *Bioorg. & Medic. Chem. Letters* 15 (2005) 1793-1797. Therefore, these molecules may be very valuable as therapeutic agents for Alzheimer's Disease. The generalized feature of these oxazole and pyrazole analogs of curcumin is that they replace the 2,4 diketone entity of natural curcumin with a cyclic N-containing heterocycle. This cyclic entity is believed to reduce the rotational freedom of the molecule.

Another such molecule that possesses a cyclic entity in the place of the 2,4 diketone entity is shown in FIG. 12. There are at least four reasons for believing that the FIG. 12 curcuminoid will have superior performance (as compared to natural curcumin) against Alzheimer's Disease:

First, elimination of the original methoxy substituents of the curcuminoid means that this curcuminoid will behave more like BDMC, shown in (33) above. As reported above by Park and Chen, BDMC is about twice as potent as natural curcumin in surviving toxic insult by β amyloid. Therefore, this FIG. 12 curcuminoid should be about twice as potent as natural curcumin in surviving toxic insult by β amyloid.

Second, the BDMC-like nature of the FIG. 12 curcuminoid should correct defects in the innate immune response of peripheral macrophages of the AD patient, as reported by Fiala, *Proc Natl Acad Sci USA*. 2007 Jul. 31; 104(31):12849-54. According to Fiala, activated peripheral macrophages of the innate immune response are thought to be responsible for the beneficial clearance of amyloid plaques in the brain. However, in many AD patients, these macrophages possess defects in internalizing β-amyloid which render them unable to clear deposited amyloid plaques, and so plaques build up in the brain and cause microglia-induced neuroinflammation. The resulting inflammation then upregulates β amyloid production, thereby provoking a vicious cycle. Fiala reports that BDMC is the curcuminoid responsible for correcting this defect in peripheral macrophages, and works optimally at a concentration of 0.1 uM.

Third, the center cyclic entity of the FIG. 12 curcuminoid is believed to reduce the rotational freedom of the molecule, thereby locking in a conformation in which the hydroxyls of the outer phenyl groups are far apart from each other. As the structural similarity between curcumin and Congo red has been reported to be the reason for the potent amyloid binding of each molecule, it appears that the conformation of curcumin that is the most potent amyloid binder is that in which the hydroxyls of the outer phenyl groups are far apart from each other. Therefore, FIG. 12 curcuminoid should have amyloid binding qualities that are superior to natural curcumin.

Fourth, inspection of this molecule reveals that it possesses virtually all of the structural characteristics of resveratrol in general, as shown in FIG. 12. Therefore, it is believed that this FIG. 12 molecule will possess the therapeutic qualities of both curcumin and resveratrol. Micromolar amounts of resveratrol significantly upregulates sirtuin expression Howtiz, *Nature*. 2003 Sep. 11; 425(6954):191-6, and sirtuins have been known to increase the alpha-amyloidogenic pathway of amyloid processing. Qin, *J Biol Chem*. 2006 Aug. 4; 281(31): 21745-54. This is advantageous because it is believed that production of the neurotoxic β-amyloid protein occurs through the β-amyloid pathway.

Therefore, it is believed this molecule of FIG. 12 will not only possess all the benefits of traditional curcumin, it will also possess:
  i) better survival (due to BDMC features)
  ii) better macrophage activation (due to BDMC)
  iii) better binding to amyloid (reduced rotational freedom)
  iv) non-amyloidogenic processing (due to resveratrol-induced sirtuin expression).

Of note, Narlawar, *Neurodegen. Dis.*, 2007, 4(2-3) 88-93, expects that, due to their reduced rotational freedom, the oxazole and pyrazole analogs of curcumin would not possess the metal chelation abilities of natural curcumin. While it may be that the oxazole and pyrazole analogs of curcumin may not possess the chelation abilities of natural curcumin, it is expected that the FIG. 12 molecule would retain the chelation abilities of resveratrol. Because resveratrol is a potent chelator, it is expected that the FIG. 12 molecule would possess potent chelation abilities.

Figure 13:
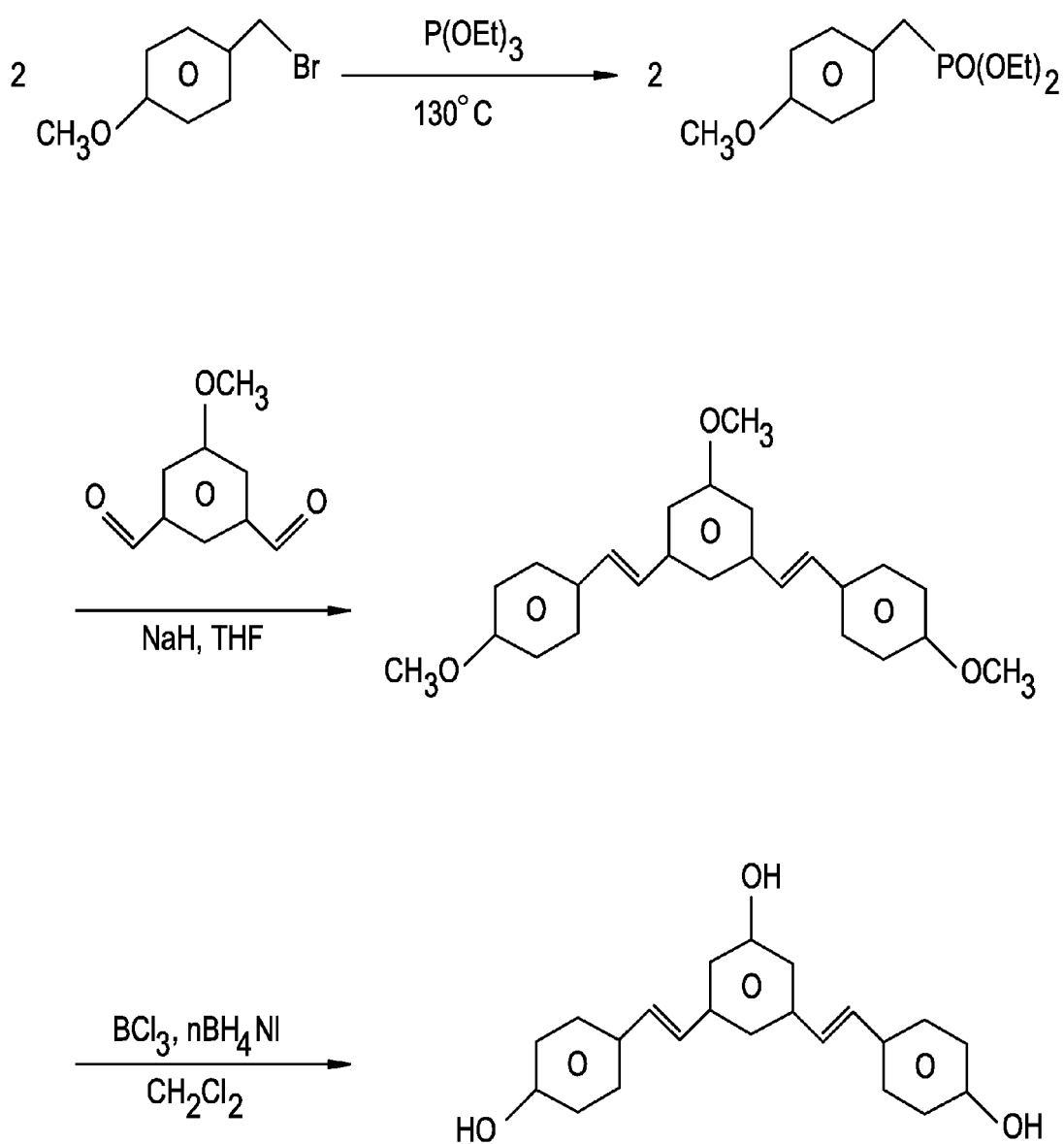

FIG. 13 provides a method of making the compound of FIG. 12 that has hydroxyl demethoxy lateral phenolic groups and a hydroxy central phenolic group.

Figure 14:
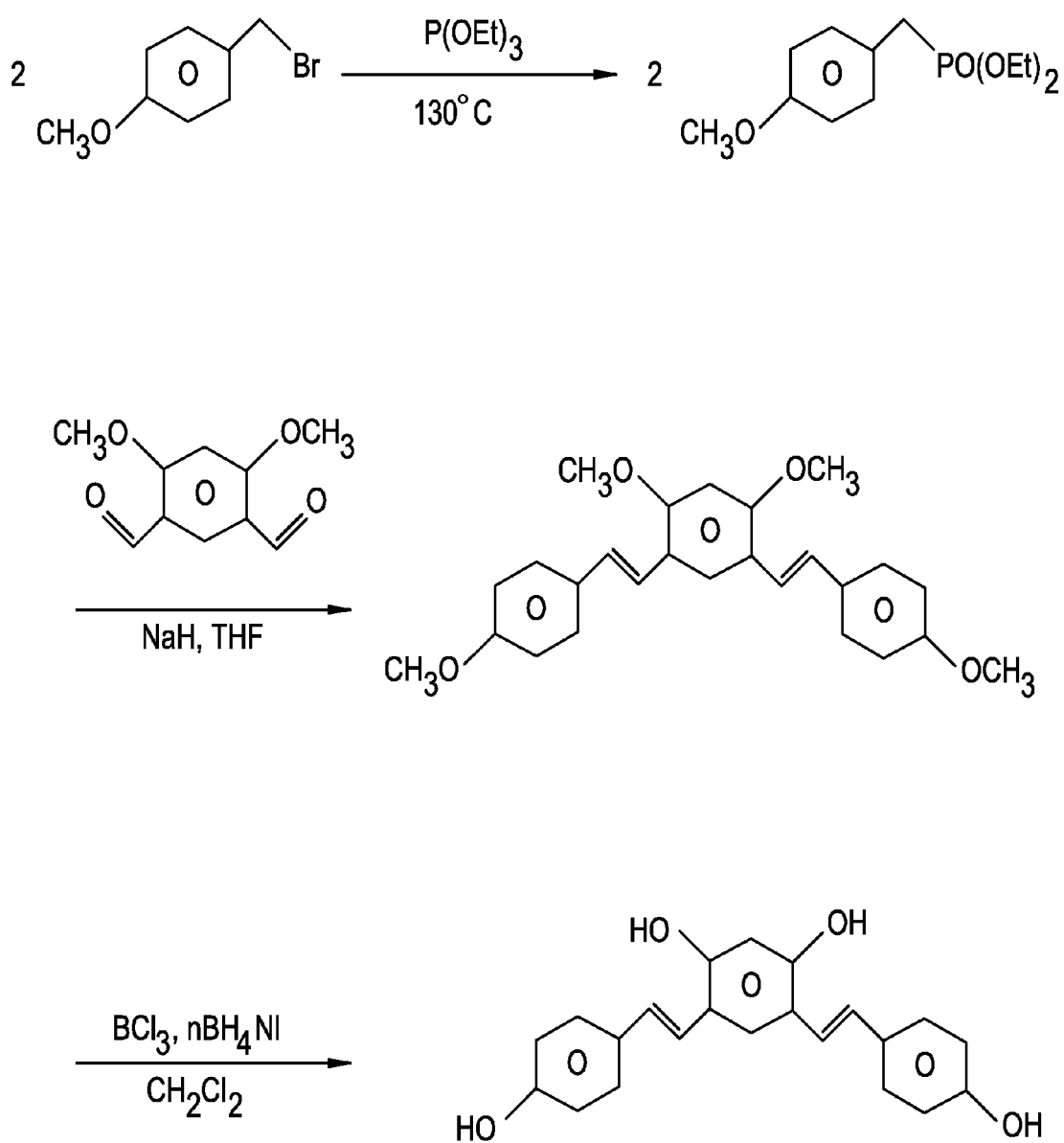

FIG. 14 provides a method of making the compound of FIG. 12 that has hydroxyl demethoxy lateral phenolic groups and a dihydroxy central phenolic group.

Figure 15:
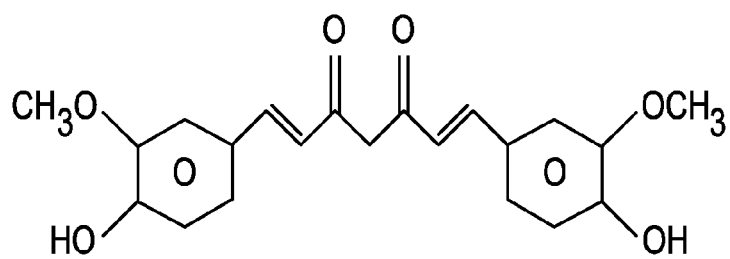
Figure 15:
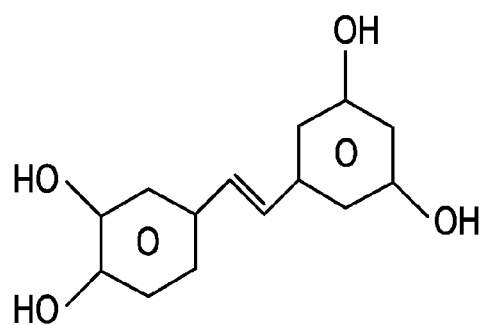
Figure 15:
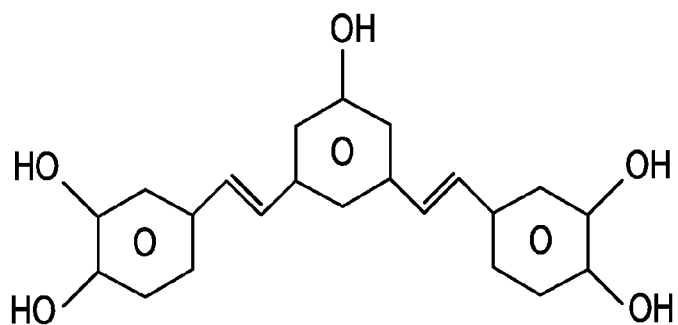

FIG. 15 discloses curcumin, piceatannol and a hybrid thereof, wherein most of the hydroxyls of the natural compounds are represented in the hybrid, providing dihydroxyls in the end phenolic groups and a single hydroxyl in the central phenolic group in the positions common with the two natural compounds. Kim, *Ann N Y Acad Sci.*, 2007 January; 1095: 473-82 reports that piceatannol treatment attenuates the intracellular accumulation of ROS induced by treatment of PC12 cells with Aβ, and inhibited Aβ-induced apoptotic features including internucleosomal DNA fragmentation, nucleus condensation, cleavage of poly(ADP-ribose) polymerase (PARP), and activation of caspase-3.

Figure 16:
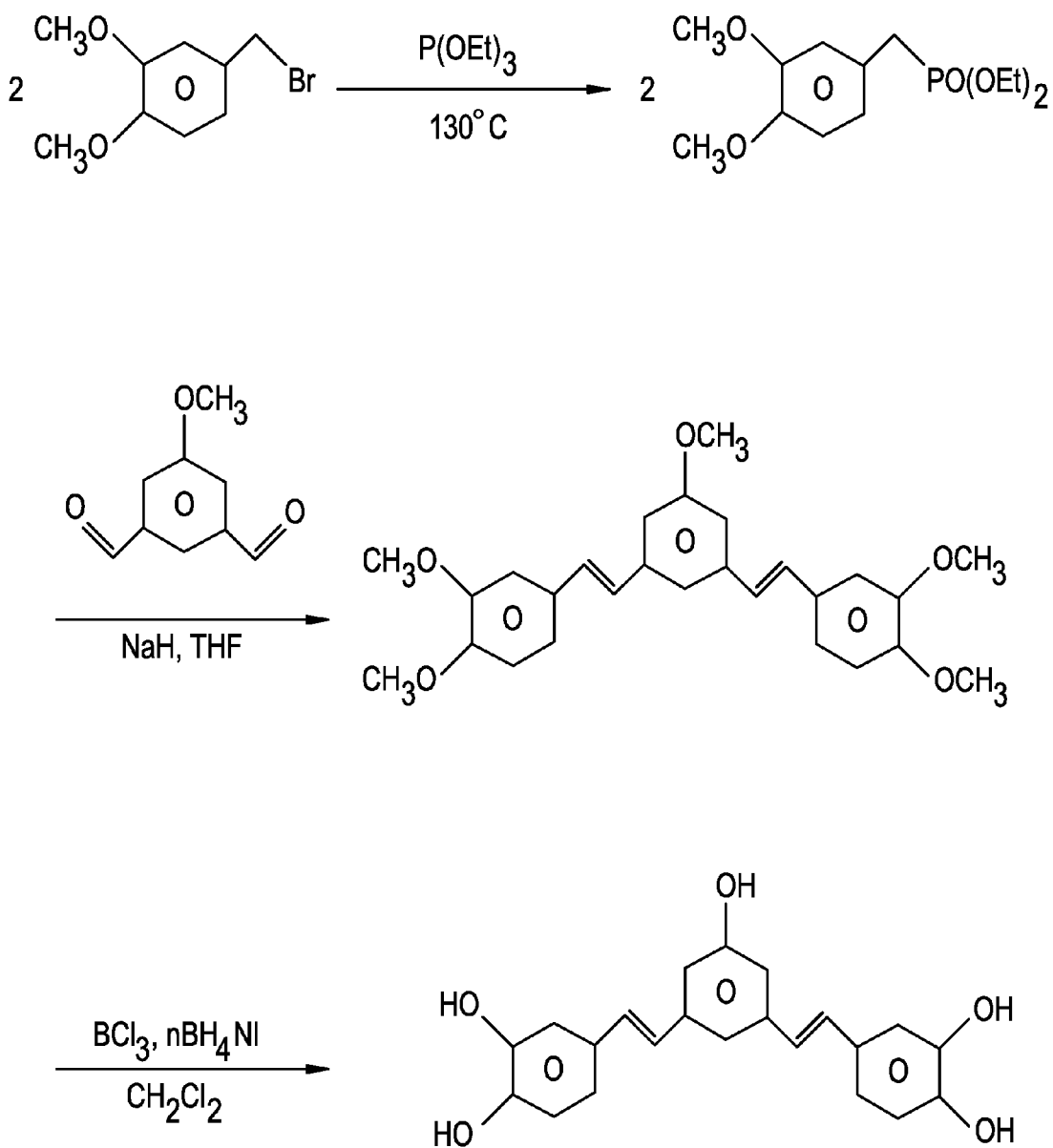

FIG. 16 provides a method of making the compound of FIG. 15.

Figure 17:
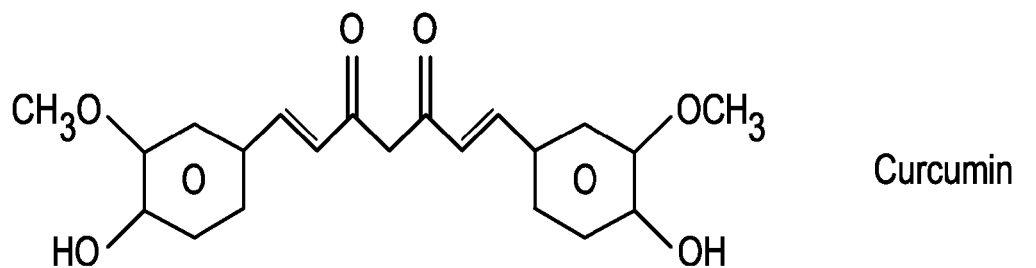
FIG. 17 discloses the structures of curcumin, 3,3',4' fisetin and a curcumin-3,3',4' fisetin hybrid, wherein all of the hydroxyls of the curcumin and 3,3',4' fisetin compounds are represented in the hybrid, providing dihydroxyls in the end phenolic groups and a hydroxyl in the place of each double bond.
Figure 17:
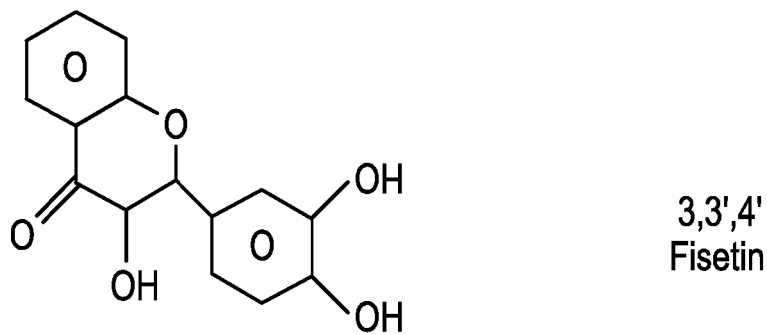
Figure 17:
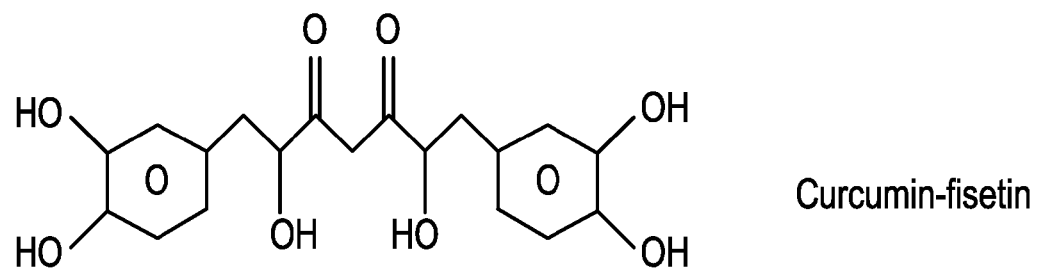

FIG. 17 discloses the structures of curcumin, 3,3',4' fisetin and a curcumin-3,3',4' fisetin hybrid, wherein all of the hydroxyls of the curcumin and 3,3',4' fisetin compounds are represented in the hybrid, providing dihydroxyls in the end phenolic groups and a hydroxyl in the place of each double bond. Maher, *Free Radic Res*. 2006 October; 40(10):1105-11 reports that fisetins in general and 3,3',4' fisetin in particular have potent (low micromolar) neurotrophic properties.

Figure 18:
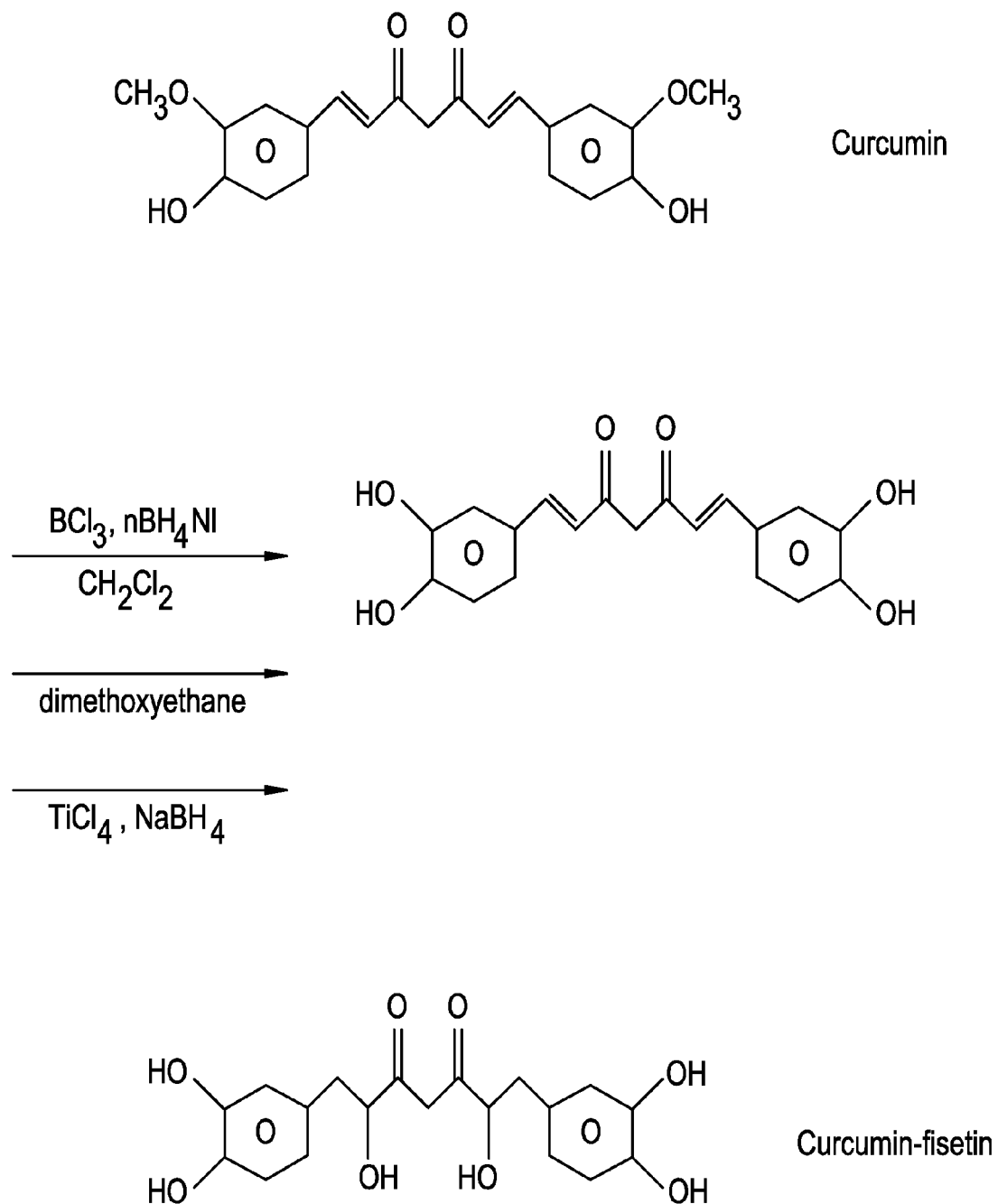
FIG. 18 discloses a method of making the curcumin-3,3',4' fisetin hybrid of FIG. 17.

FIG. 18 discloses a method of making the curcumin-3,3',4' fisetin hybrid of FIG. 17.

Figure 19:
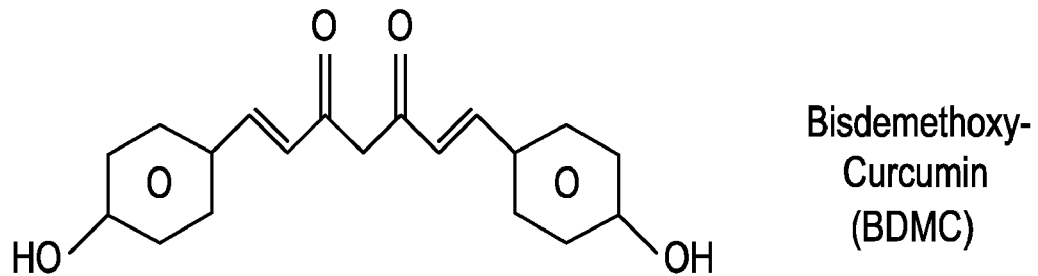
FIG. 19 discloses the structures of curcumin, honokiol and a curcumin-honokiol hybrid, wherein all of the hydroxyls of the curcumin and honokiol compounds are represented in the hybrid, providing a single hydroxyl in the end phenolic groups and a hydroxyl in the place of each double bond.
Figure 19:
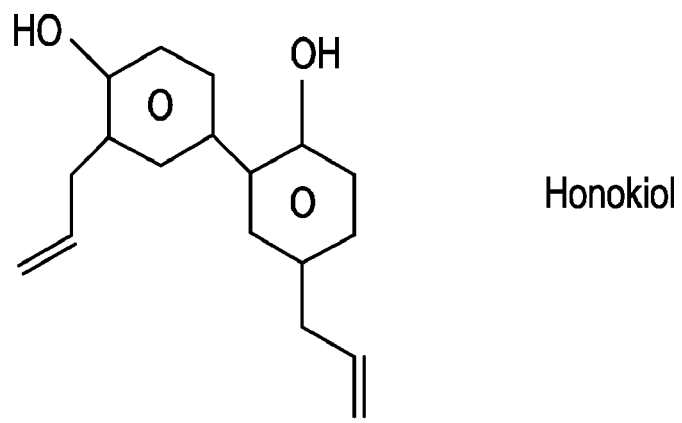
Figure 19:
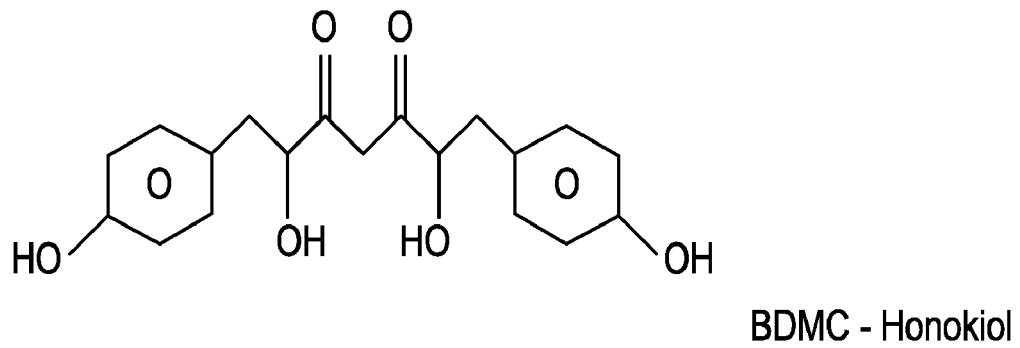

FIG. 19 discloses the structures of curcumin, honokiol and a curcumin-honokiol hybrid, wherein all of the hydroxyls of the curcumin and honokiol compounds are represented in the hybrid, providing a single hydroxyl in the end phenolic groups and a hydroxyl in the place of each double bond. Fukuyama, *Bioorg Med Chem Lett*. 2002 Apr. 22; 12(8): 1163-6 reports that honokiol has potent neurotrophic properties.

Figure 20:
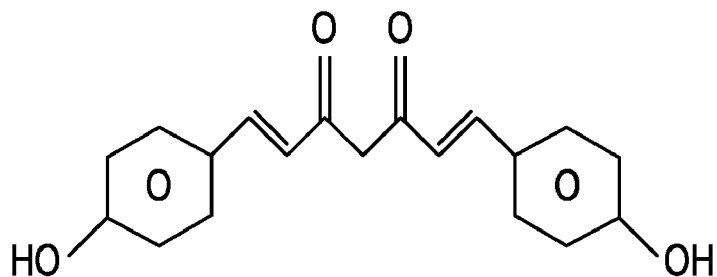
FIG. 20 discloses a method of making the curcumin-honokiol hybrid of FIG. 19.
Figure 20:
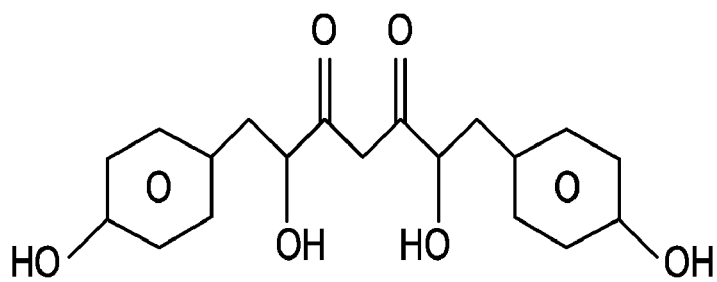

FIG. 20 discloses a method of making the curcumin-honokiol hybrid of FIG. 19.

Figure 21:
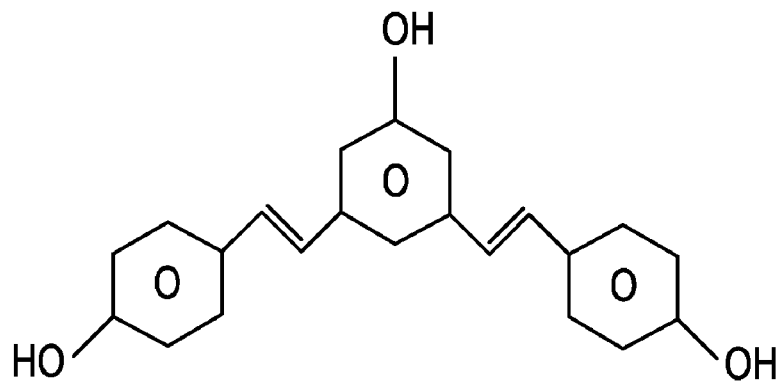
FIG. 21 discloses a method of making a FIG. 13—honokiol hybrid, wherein all of the hydroxyls of the natural compounds are represented in the hybrid, providing single hydroxyl in the end phenolic groups in the positions common with the two natural compounds, a hydroxyl in the central phenolic group, and a hydroxyl in the place of each curcumin double bond.
Figure 21:
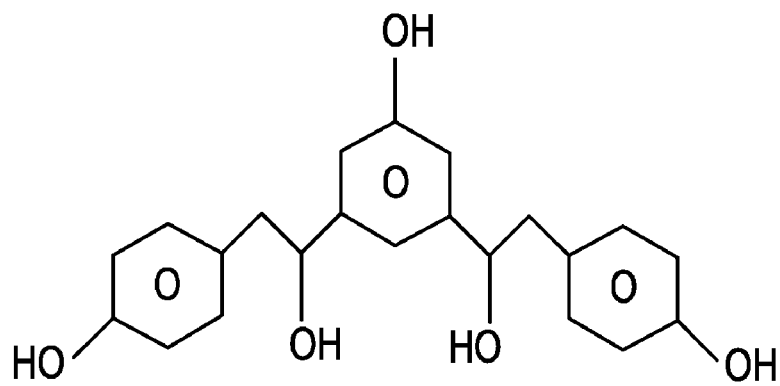

FIG. 21 discloses a method of making a FIG. 13—honokiol hybrid, wherein all of the hydroxyls of the natural compounds are represented in the hybrid, providing single hydroxyl in the end phenolic groups in the positions common with the two natural compounds, a hydroxyl in the central phenolic group, and a hydroxyl in the place of each curcumin double bond.

Figure 22:
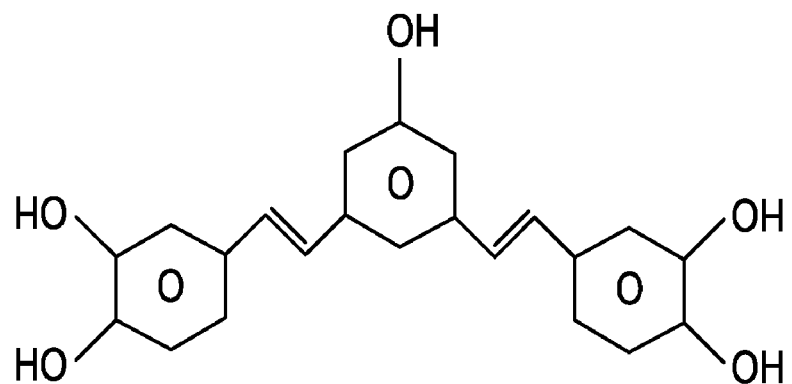
FIG. 22 discloses a method of making a FIG. 15—3,3',4' fisetin hybrid, wherein all of the phenolics of the natural compounds are represented in the hybrid, providing single hydroxyl in the end phenolic groups and a hydroxy central phenolic group in the positions common with the two natural compounds, and an additional hydroxyl in the place of each curcumin double bond.
Figure 22:
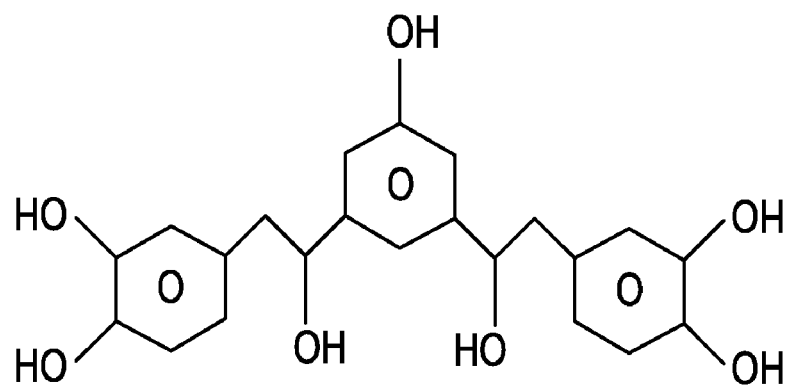

FIG. 22 discloses a method of making a FIG. 15—3,3',4' fisetin hybrid, wherein all of the phenolics of the natural compounds are represented in the hybrid, providing single hydroxyl in the end phenolic groups and a hydroxy central phenolic group in the positions common with the two natural compounds, and an additional hydroxyl in the place of each curcumin double bond.

Transdermal Iontophoresis

In some embodiments, the curcuminoid drug is delivered to the bloodstream of the patient via transdermal iontophoresis. Iontophoresis refers to the introduction, by means of an electric current, of ions of soluble salts into the tissues of the body. In iontophoretic delivery systems, an applied electric potential gradient is employed to enhance the transdermal delivery of ionized drug molecules.

In a preferred embodiment, a charged curcuminoid prodrug is administered transdermally by iontophoresis. Preferably, the ionized or ionizable drug molecule is preferably a charged curcumin glycinate ester, which exhibits enhanced iontophoretic transdermal flux over that of the unmodified parent compound.

The literature reports the transdermal iontophoresis of ionically charged prodrugs. In particular, Laneri, *Pharm. Res.*, 16, 12, 1999, 1818-1824 investigated the benefits of iontophoretically transporting a prodrug of DHEA, which is a lipophilic polycyclic alcohol like curcumin. Laneri reports the iontophoretic flux of PRO2 (an ionic prodrug of DHEA having a trimethylglycinate prodrug moiety) as being 0.0714 $\mu$mol cm$^{-2}$ h$^{-1}$, or about 20 $\mu$g/(cm$^2$·h). Likewise, U.S. Pat. No. 5,622,944 (ALZA) reports the iontophoretically transporting an ionic prodrug of testosterone, which is a lipophilic polycyclic alcohol like curcumin. U.S. Pat. No. 5,622,944 reports an iontophoretic flux of testosterone-17$\beta$-stachydrine ester, chloride salt (testosterone having a heterocyclic amine prodrug moiety) as being about 40 $\mu$g/(cm$^2$·h). In each case, the investigator found a virtual absence of the prodrug in the receiving reservoir, indicating that the skin-based esterases cleaved the ester moiety of the prodrug, thereby allowing the base drug to enter the receiving reservoir. Accordingly, it is believed that skin-based esterases will cleave the ester moiety of the curcumin prodrug, thereby allowing the base curcumin drug to enter the receiving blood stream.

Therefore, it is believed that curcumin may be safely delivered into the blood stream in pharmaceutically significant quantities by the transdermal iontophoresis of ionically charged curcumin prodrugs or analogs.

The predicted concentration of a drug delivered through transdermal iontophoresis can be found via the equation:

$$\text{Concentration} = \frac{\text{Flux} \times \text{Surface Area}}{\text{Clearance}} = \frac{J \times SA}{Cl}$$

where
Concentration is provided in ($\mu$g/l),
Flux is provided in $\mu$g/(cm$^2$·h),
Surface Area is provided in (cm$^2$), and
Clearance is provided in (l/hr).

In general, the literature has reported the transdermal iontophoresis of charged small molecules produces fluxes in the following approximate ranges provided in Table VI:

TABLE VI

| Drug | Reservoir Conc. (mM) | Reservoir Volume (ml) | Flux $\mu$g/(cm$^2$ · h) | Source |
|---|---|---|---|---|
| Testosterone | 4 mg/ml | 1 ml | 40 | a |
| DHEA (PRO2) | 0.85 mg/ml | 1 | 20 | b |
| Salicylic Acid | 2 mg/ml | 0.5 | 41.17 | c. |
| SNA | 0.2 mg/ml | 8 ml | 23.02 | d. |
| 5-OH-DPAT | 2.3 mg/ml | NA | 90 | e |
| Timolol | 10 mg/ml | 2 ml | 200 | f |
| Timolol | 20 mg/ml | 2 ml | 250 | f |
| Atenolol | 40 mg/ml | 2 ml | 400 | f | a U.S. Pat. No. 5,622,944 (ALZA) (reported as 4 mM)
b Laneri, Pharm. Res., 16, 12, 1999, 1818-1824
c. Murthy, J Pharm Sci. 2007 Feb; 96(2): 305-11
d. Fang, Int J Pharm. 2002 Mar 20; 235(1-2): 95-105
e Nugroho, J. Controlled Release, 103, 2, 21 March 2005, 393-403
f Denet, Pharm Res. 2003 Dec; 20(12): 1946-51.

As demonstrated above, it is reasonable to conclude that glycinate-based curcumin prodrugs can achieve aqueous solubilities in the range of 25-50 mg/ml, which is far above the range of drug concentrations used in the upper portion of the above Table. Therefore, it is very reasonable to conclude that transdermal iontophoresis of charged curcumin can, in a worst case, produce fluxes at least similar to those reported in the upper portion of Table VI, that is, in the range of about 35 $\mu$g/(cm$^2$·h).

In general, the literature has reported that electrodes associated with the transdermal iontophoresis of charged small molecules are found in the following size ranges in Table VII:

TABLE VII

| Drug | Range of Surface Areas (cm$^2$) | Preferred Surface Area (cm$^2$) | Source |
|---|---|---|---|
| Testosterone | 5-50 | 25 | a |
| DHEA | 50 | 50 | b | a U.S. Pat. No. 5,622,944 (ALZA)
b Laneri, Pharm. Res., 16, 12, 1999, 1818-18-24

Therefore, it is reasonable to conclude that transdermal iontophoresis of charged curcumin can be accomplished with electrodes having a 50 cm$^2$ surface area (about a three inch square).

Vareed, *Cancer Epidiol. Biomarkers Prev.*, 2008 June 17 (6) 1441-7 reported on the pharmacokinetics of curcumin conjugate metabolites in healthy human volunteers, and found that for a dose (D) of about 11 g, the area-under-the-curve (AUC) was estimated to be about 30 $\mu$g/ml·hr. However, such values appear to relate to conjugated curcumin, not free curcumin. Nonetheless, the data from Vareed are useful because it is believed that the transdermal transfer of curcumin will avoid the precise metabolism by the gut and liver that caused Vareed to find substantially conjugated curcumin in their human subjects and not free curcumin.

Therefore, since Clearance (Cl) is found by:

$$Cl=D/AUC,$$

we can reasonably estimate the clearance (Cl) of curcumin in humans as being about 11 g/(30 $\mu$g/ml·hr), or about 350 L/hr. A clearance value of Cl=350 L/hr is substantially equivalent to the 495 L/hr and 713 L/hr values reported by Shoba, *Planta Med.* 1998 May; 64(4):353-6 in the oral dosing of rats with either curcumin alone or curcumin with piperine.

Therefore, the following analysis will use a clearance value of 350 L/hr. It is likely that the 350 L/hr value is a conservative estimate for iontophoresis in that it reflects the significant amount of metabolism that occurs during oral dosing of curcumin which would be absent in the dermal transfer setting. Rather, it is likely that the clearance value of 7.33 L/hr reported by Shoba for the oral dosing of curcumin plus piperine would be more predictive in the iontophoresis setting because piperine disables the drug enzymes systems of the gut and liver and so provides a transfer substantially absent of metabolic interference, as is anticipated for iontophoresis. Nonetheless, the following analysis will use a clearance value of 350 L/hr.

Now that each of flux, surface area and clearance values have been provided, the predicted plasma concentration of curcumin reasonably achievable by transdermal iontophoresis can be calculated:

$$\begin{aligned}
\text{Concen.} &= \frac{\text{Flux} \times \text{Surface Area}}{\text{Clearance}} \\
&= \frac{J \times SA}{Cl} \\
&= \frac{35 \times 50}{350} \\
&= 5 \text{ } \mu\text{g/l} \sim 0.012 \text{ } \mu\text{M}.
\end{aligned}$$

Thus, a worst case plasma concentration of curcumin achievable by transdermal iontophoresis can be predicted as 0.012 µM, or about 5 ng/ml.

Since curcumin crosses the blood brain barrier fairly easily, it is believed that curcumin will achieve at least substantially the same concentration in the brain as the blood. This assumption is supported by the curcumin literature. For example, Yang. *J. Biol. Chem.*, 280(7), 5892-5901 (2005) reports that mouse brain curcumin levels of about 1.1 µM were measured one hour after dosing that produced a 1.6 µM concentration in the plasma. Likewise, Begum, *J. Pharmacol Exp Ther.* 2008 Apr. 16, reports that, for i.p. and i.m. administration of curcumin in mice, the curcumin concentration is about 5 fold higher in brain than in plasma. Therefore, it is reasonable to conclude that the iontophoresis of curcumin prodrugs or analogs that can produce 0.012 µM plasma levels will also produce brain levels of at least about 0.012 µM. Thus, the AD patient may expect to gain valuable benefits from iontophoretic transfer.

Therefore, in some embodiments, there is provided a method of delivering a curcuminoid to a patient (preferably, an AD patient), comprising the steps of:
  a) iontophoretically delivering a charged curcuminoid (preferably, a charged curcuminoid prodrug) across a skin of the patient.

Although it has been predicted that transdermal iontophoresis can produce a 0.012 µM plasma concentration in Alzheimer's patient, it is believed that simple modifications can lead to substantial increases in the resultant plasma and brain concentrations. These involve changes to the valence of the ionic prodrug, the magnitude of the iontophoresis current, and the drug reservoir concentration. Each of these will now be described below:

In general, increasing the concentration of drug in the iontophoretic reservoir leads to a linear increase in the drug's flux. For example, increasing the concentration of 5-OH-DPAT from 0.25 to 0.5, 1.3 and 2.3 mg/ml resulted in a linear increase in flux from 39.1 to 78.4, 187.6 and 318.2 nmol/(cm·h), respectively. Nugroho, *J. Controlled Release,* 103, 2, 21 March 2005, 393-403. As demonstrated above, it is reasonable to conclude that glycinate-based curcmin prodrugs can achieve aqueous solubilities in the range of 25-50 mg/ml. This higher range is about 10-fold greater the reservoir concentrations of the drugs reported in the upper portion of Table VI. Therefore, it is reasonable to believe that the reservoir concentration of curcumin prodrug used to produce the iontophoresis can be increased to about 25-50 mg/ml, and the resultant flux and plasma concentration of curcumin can be respectively increased to about 400 µg/(cm²·h) and about 60 ng/ml, or about 0.14 µM. Thus, a brain curcumin concentration of about 0.14 µM may be realized by iontophoresis.

Comparison of this 0.14 µM plasma value with the reported activity of curcumin in plasma reveals that the AD patient may expect to gain valuable benefits from iontophoretic transfer. For example, Fiala, *Proc Natl Acad Sci USA.* 2007 Jul. 31; 104(31):12849-54 reports that 0.1 uM is the optimum level of BDMC that stimulates AD patients' macrophages to clear β amyloid. Thus, the 0.14 µM plasma concentration slightly exceeds the 0.1 µM optimum level of BDMC reported by Fiala to stimulate AD patients' macrophages to clear β amyloid.

The 60 ng/ml estimate of curcumin plasma concentration is also in line with some iontophoresis-driven drug plasma values reported in the art. Indeed, the literature has reported that transdermal iontophoresis of charged molecules can produce serum concentrations that approach the 0.5 µM range (~200 ng/ml). For example, Bender, *Arzneimittelforschung.* 2001; 51(6):489-92 reports that iontophoresis of 100 mg of etofenamate for 20 minutes in humans produces a serum concentration of about 200 ng/ml. Conjeevaram *Pharm Res.* 2003 September; 20(9):1496-501 reports that iontophoresis via a 10 mg/ml patch of propranolol in rats with a 0.1 mA/cm² current density produces a Cmax serum concentration of about 200 ng/ml.

Abla, *Pharm. Res,* 2005 December; 22(12):2069-78, reports that higher valence ions display greater iontophoretic flux. Because higher valence molecules are more easily transported by iontophoresis, it is advantageous to replace not just one but both of the hydroxy groups of the curcumin molecule with charged glycinate moieties.

Therefore, in some embodiments, there is provided curcumin analogs (1')-(30') particularly suited for iontophoretic delivery, wherein each of the hydroxyl groups of the curcumin base molecule is replaced with polar or charged moieties (i.e., each of the two OH groups of the parent curcumin molecule is replaced with an OR group). In embodiments used in iontophoresis, each of the hydroxyl groups of the parent curcumin molecule is replaced with charged moieties, preferably ammonium glycinate. In some embodiments, each of the hydroxyl groups of the curcumin molecule are replaced with a trimethylglycinate moiety to make curcumin di(trimethylglycinate) dichloride.

Therefore, solely through the use of a divalent curcumin salt, it is reasonable to believe that the resultant flux and plasma concentration of curcumin can be respectively doubled to about 800 µg/(cm²·h) and about 0.3 µM.

U.S. Pat. No. 5,622,944 reports that, in iontophoretic administration, the drug or prodrug delivery rate is proportional to the amount of current applied. The literature has reported that doubling the amperage of the current used to produce the iontophoresis can lead to a doubling of the drug flux. Since it is reasonable to believe that the current used to produce the iontophoresis can be increased to about 0.5 mA/cm², and the resultant flux and plasma concentration of curcumin can be respectively increased to about 800 µg/(cm²·h) and 0.3 µM.

Curcumin is highly lipophilic and therefore would be expected to bioaccumulate in fatty tissues such as brain tissue. Accordingly, it is reasonable to expect the curcumin concentration in a patient's brain to be higher than the curcumin concentration in that patient's plasma. As reported above, Yang. *J. Biol. Chem.,* 280(7), 5892-5901 (2005) reports that mouse brain curcumin levels (1.1 µM) were about the same as its plasma levels (1.6 µM) when measured one hour after dosing, while Begum, *J. Pharmacol Exp Ther.* 2008 Apr. 16, reports that, for i.p. and i.m. administration of curcumin in mice, the curcumin concentration in mice is about 5-13 fold higher in brain than in plasma. Without wishing to be tied to a theory, it is believed that the numbers reported by Begum would be more reflective of bioaccumulation, particularly Begum's chronic dosing, which produced brain/plasma ratios of between 3:1 and 13:1. Therefore, if an 8-fold bioaccumulation factor is taken into account, it is reasonable to conclude that the iontophoresis of curcumin prodrugs or analogs that can produce:
  a) 0.012 µM plasma curcumin levels will also produce brain levels of about 0.1 µM (assuming a worst case prodrug solubility of about 2-5 mg/ml), and
  b) 0.14 µM plasma curcumin levels will also produce a brain curcumin concentration of about 1.1 µM (assuming a prodrug solubility of about 25-50 mg/ml).

As explained above, the iontophoretic delivery of curcumin will provide, in a worst case, a serum/plasma concentration of about 0.012 µM (5 µg/l), and may likely be able to achieve a serum/plasma concentration of about 0.3 µM (150 µg/l). These values are essentially equivalent to the 0.006 µg/ml and 0.18 µg/ml serum Cmax values for oral curcumin reported by Shoba, *Planta Med.* 1998 May; 64(4):353-6, who provided volunteers with 2 g/day of oral curcumin supplemented with piperine. Therefore, on the basis of Cmax values alone, iontophoresis may be considered to be substantially equivalent to oral dosing.

Moreover, iontophoretic delivery appears to be superior to oral curcumin-piperine in two major respects. The first major advantage of delivering curcumin iontophoretically is that the iontophoretic delivery into the blood stream occurs not via a bolus, but rather occurs steadily 24 hours a day. In contrast, oral delivery of curcumin as per Shoba often produces a spiked delivery lasting less than about an hour in the bloodstream. Therefore, iontophoresis may provide a 24-fold advantage over oral delivery in terms of area-under-the-curve (AUC) bioavailability. Indeed, the 24 hour AUCs can be compared in Table VIII:

TABLE VIII

| Investigator | Technology | AUC (hr · ug/l) |
|---|---|---|
| Present invention | Iontophoresis | |
| worst case | | 5 ug/l × 24 = 120 |
| likely | | 150 ug/l × 24 = 3600 |
| Vareed | Oral Dosing | ~30 |
| Shoba | Oral Dosing | 4 |
| Shoba | Oral + piperine | 80 |

Therefore, on the basis of AUC values alone, curcumin iontophoresis may be considered to be substantially superior to oral curcumin dosing.

The second major advantage of iontophoresis over oral dosing with piperine lies in the fact that piperine is a non-specific inhibitor of metabolic enzyme systems in the digestive tract and liver. Accordingly, patients taking other pharmaceuticals in addition to a curcumin-piperine tablet may find that, due to piperine disabling their native enzyme systems, all of the other pharmaceuticals they have ingested are also becoming much more bioavailable and therefore much more potent. Thus, iontophoretic curcumin may be much safer than oral dosing of curcumin plus piperine.

Therefore, iontophoretic curcumin may be able to deliver a much greater amount of curcumin than that reported by Shoba, but without disabling the delicate drug-metabolizing enzyme systems in the gut and liver of the patient.

According to U.S. Published Patent Application 2003/0157155, transdermal formulations are preferably used for administration of active ingredients which, because of their physicochemical properties, are easily able to overcome the barrier of the skin. To do this, the active ingredients must have sufficient solubility both in the lipophilic stratum corneum and in the underlying hydrophilic living epidermis. Flynn G., Stewart B. *Drug Dev. Res.* 13:169-185 (1988) describe a good correlation between the in vitro octanol/water (O/W) partition coefficient and skin permeability and recommend those active ingredients whose partition coefficient is about 100 (log P=2) as candidates for transdermal administration. Likewise, Guy, *Fundam. Appl. Toxicol.* 17: 575-583(1991) shows a parabola-like dependence between the logarithm of the maximum penetration rate and the logarithm of the octanol/water partition coefficient with an apex maximum at log P=2. Therefore, it appears that molecules with an O/W PC log P of about 2 should be good candidates for transdermal delivery.

Without wishing to be tied to a theory, it is believed that the partition coefficient of the charged curcumin prodrug will be within a range that is highly favorable for transdermal delivery. It is noted that native curcumin has an O/W partition coefficient of about log P=3, and that converting DHEA into its PRO2 prodrug reduced the O/W partition coefficient of DHEA from log P=1.54 to log P=0.79 (i.e., a reduction in log P of about 0.75). If modifying curcumin with the trimethylglycinate moiety has the same effect upon curcumin lipophilicity as it had for DHEA, then the log P O/W partition coefficient of the trimethylglycinate curcumin should be about log P=2.5. Since this value is close to the transdermal delivery optimum of about log P=2, it appears that curcumin glycinate prodrugs with an O/W partition coefficient log P of about 2.5 should be good candidates for transdermal delivery.

Therefore, in some embodiments of the present invention the curcuminoid prodrug has a log P O/W partition coefficient of between about 1 and 3, preferably between about 1.5 and 2.5, more preferably between 1.7 and 2.3.

Figure 23:
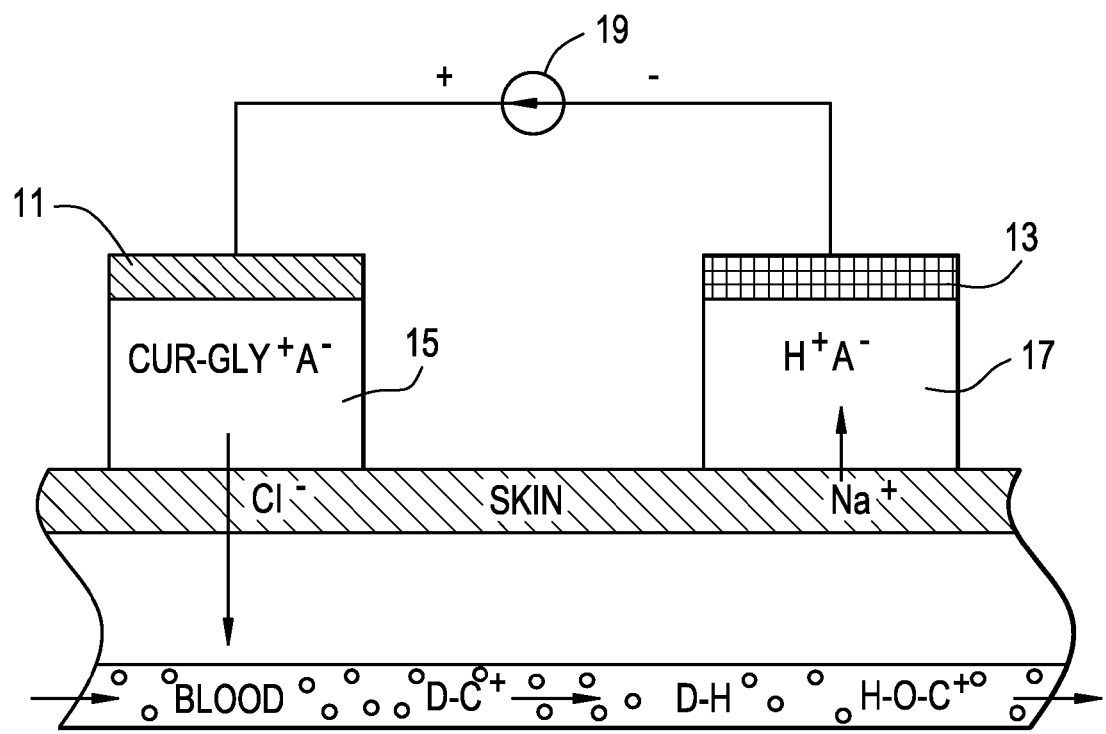
FIG. 23 discloses a typical iontophoresis system for delivering the charged curcumin prodrugs of the present invention to an AD patient.

A typical iontophoretic device for administering the prodrug of the present invention is provided in FIG. 23. An iontophoretic drug delivery system is generally composed of four basic components: a power source (typically batteries), control circuitry, electrodes, and two electrolyte-containing reservoirs. Using FIG. 23 as an example, in a conventional arrangement, two electrodes are disposed so as to be in intimate contact with the skin of a subject, as illustrated by 11 and 13, the anode and cathode, respectively. Both electrodes are placed within a given skin region of the subject. One electrode is in contact with a reservoir containing the prodrug or donor reservoir 15, and the other is contained within a ground reservoir 17 containing a biocompatible electrolyte solution, such as sodium chloride. In the figure, the charged curcumin prodrug is designated as "CUR-GLY$^+$ A$^-$", with "CUR-GLY$^+$" representing the charged curcumin ester portion of the complex. In the figure, "A$^-$" is the complex counterion.

The electrode in contact with the prodrug is generally referred to as the "active" electrode 11. The active electrode is the one from which the prodrug is driven into the body by application of an electric gradient. In a preferred embodiment of the present invention, the prodrug is a positively charged quaternary ammonium derivative of curcumin and the active electrode is the anode. For iontophoretic delivery of curcumin prodrugs which are negatively charged, the active electrode is the cathode.

The other electrode, contained within a second reservoir, is often referred to as the ground electrode 13, and serves to close the electrical circuit through the body. In some instances, delivery of the same drug out of both reservoirs in an alternating fashion can be carried out by periodically reversing the polarity of the electrodes.

A variety of electrode materials may be used in the iontophoretic delivery device, and range from materials such as platinum to silver-silver chloride. The choice of electrode will depend on the nature of the prodrug to be administered, among other considerations.

The active reservoir 15 will typically contain a solution of the prodrug species to be driven transdermally into the subject (including both the active species and accompanying counterions). The prodrug may be contained within an aqueous solution, or within a hydrophilic gel or gel matrix. In some instances, the active reservoir will contain the prodrug as a semi-solid, foam, or formulated with an absorbent material. The ground reservoir may similarly contain salt ions in an aqueous solution, or within a polymeric matrix.

Typically, the active reservoir will also contain buffers to maintain the reservoir environment at the same charge as the electrode. In most cases, a buffer possessing an opposite charge to the active prodrug will be employed. In some instances, depending on the counterion of the prodrug salt, the prodrug salt may act as its own buffer. In general, to achieve the highest transport efficiency, the concentration of all ionic species, with the exception of the curcumin prodrug, is minimized.

In some embodiments of the invention, the iontophoretic device will optionally contain a selectively permeable membrane. The membrane may be located in a region separating the two reservoirs, or alternatively, may separate the contents of the active reservoir from the skin surface. Suitable materials for providing such membranes include natural and synthetic polymers.

In iontophoretically administering a curcumin/chemical modifier complex to a subject, the circuit is completed by connection of the two electrodes to a source of electrical energy 19, such as a battery. An electronic control module is utilized to control the applied current, and in some cases, may comprise an integrated circuit, which would allow for varying time intervals or feedback-controlled drug delivery.

Transdermal iontophoretic delivery is accomplished by application of an electric current. In iontophoretic administration, the drug or prodrug delivery rate is proportional to the amount of current applied.

In iontophoretically administering a charged curcumin prodrug of the present invention, an appropriate current intensity is selected which is below the pain threshold of the subject. The current should be within comfortable toleration of the patient, with a current density which is typically less than 0.5 $mA/cm^2$ of the electrode surface. The current is then applied for an appropriate length of time.

In a preferred embodiment of the invention, upon application of electric potential, positively charged prodrug ions at the active electrode (in this case, the anode) are driven from the donor reservoir, through the skin, and into the body. Simultaneously, negatively charged ions in the body of the subject will migrate from the body and into the donor reservoir. At the ground electrode (cathode in this case), negatively charged ions are driven into the skin, while positively charged ions from the body of the subject migrate into the ground reservoir. In order to maintain charge neutrality, oxidation occurs at the positive electrode and reduction at the negative electrode, as ions migrate from one side of skin to the other. Upon transport of the complex across the skin and into the bloodstream, cleavage occurs to release the parent curcumin in its active form.

The invention claimed is:

1. A method of delivering a curcuminoid to a patient, comprising the steps of:
   a) iontophoretically delivering a charged curcuminoid prodrug across a skin of the patient.

2. The method of claim 1 wherein the patient has Alzheimer's Disease.

3. The method of claim 1 wherein the charged curcuminoid prodrug comprises a glycinate moiety.

4. The method of claim 1 wherein the curcuminoid comprises bisdemethoxycurcumin.

5. The method of claim 1 wherein the curcuminoid is a hybrid of curcumin and resveratrol.

6. The method of claim 1 wherein the curcuminoid is a hybrid of bisdemethoxycurcumin and resveratrol.

7. The method of claim 1 wherein the curcuminoid is a hybrid of curcumin and 3,3',4' fisetin.

8. The method of claim 1 wherein the curcuminoid is a hybrid of bisdemethoxycurcumin and 3,3',4' fisetin.

9. The method of claim 1 wherein the curcuminoid is a hybrid of curcumin and honokiol.

10. The method of claim 1 wherein the curcuminoid is a hybrid of bisdemethoxycurcumin and honokiol.

* * * * *